US006287788B1

(12) United States Patent
Bard et al.

(10) Patent No.: US 6,287,788 B1
(45) Date of Patent: Sep. 11, 2001

(54) DNA ENCODING GALANIN GALR3 RECEPTORS AND USES THEREOF

(75) Inventors: Jonathan A. Bard, Doylestown, PA (US); Beth Borowsky, Montclair, NJ (US); Kelli E. Smith, Wayne, NJ (US); Theresa A. Branchek, Teaneck, NJ (US); Christophe P. G. Gerald, Ridgewood, NJ (US); Kenneth A. Jones, Bergenfield, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/199,737

(22) Filed: Nov. 25, 1998

Related U.S. Application Data

(63) Continuation of application No. PCT/US97/18222, filed on Oct. 9, 1997, and a continuation-in-part of application No. 08/900,230, filed on Jul. 23, 1997, which is a continuation-in-part of application No. 08/787,261, filed on Jan. 24, 1997, now abandoned, which is a continuation-in-part of application No. 08/767,964, filed on Dec. 17, 1996, now abandoned, which is a continuation-in-part of application No. 08/728,139, filed on Oct. 9, 1996, now abandoned.

(51) Int. Cl.[7] .......................... G01N 33/53; G01N 33/50; G01N 33/566

(52) U.S. Cl. .......................... 435/7.21; 435/7.1; 435/7.2; 435/69.1

(58) Field of Search .................................... 435/7.2, 69.1, 435/7.1, 7.21

(56) References Cited

U.S. PATENT DOCUMENTS

| | | | |
|---|---|---|---|
| 5,290,808 | 3/1994 | Sofia et al. | 514/483 |
| 5,436,128 | 7/1995 | Harpold et al. | 435/6 |
| 5,436,155 | 7/1995 | Bell et al. | 435/252.3 |
| 5,462,856 | 10/1995 | Lerner et al. | 435/7.21 |
| 5,508,164 | 4/1996 | Kausch et al. | 514/324 |
| 5,567,714 | 10/1996 | Bruns et al. | 514/13 |
| 5,576,296 | 11/1996 | Bartfai et al. | 514/13 |

FOREIGN PATENT DOCUMENTS

| | | |
|---|---|---|
| 5143611 | 11/1992 | (EP) . |
| 7118302 | 5/1996 | (EP) . |
| 9212997 | 8/1992 | (WO) . |
| 9215015 | 9/1992 | (WO) . |
| 9215681 | 9/1992 | (WO) . |
| 9522608 | 8/1995 | (WO) . |
| 9746681 | 12/1997 | (WO) . |
| 9803059 | 1/1998 | (WO) . |
| 9803548 | 1/1998 | (WO) . |
| 9931130 | 6/1999 | (WO) . |

OTHER PUBLICATIONS

Ahmad, A., et al., "Identification And Molecular Cloning Of A Novel Galanin Receptor (GALR–2) In Rat Sensory Neurons", *Soc. Neurosci. Abstr.* (1996) 22(3): 1682, Abstract No. 661.10.

Ahmad, S., et al., "Molecular Cloning Of A Novel Widely Distributed Galanin Receptor Subtype (GALR–2)" *International Association for the Study of Pain* (IASP Press) (1996) Abstract No. 81: 134.

Ahmad, S., et al., Astra Pain Control (1996), poster.

Bartfai, T., et al., "Galanin Receptor Ligand M40 Peptide Distinguishes Between Putative Galanin–Receptor Subtypes" *PNAS* (USA) (1993) 90: 11287–11291.

Bouvier, M., et al., "Dynamic Palmitoylation of G–Protein–Coupled Receptors in Eukaryotic Cells" *Methods in Enzymology* (1995) 250: 300–314.

Bowie, et al., Deciphering the message in protein sequences: tolerance to amino–acid substitutions. Science (1990) 247: 1306–1310.

Burgevin, M.C., et al., "Cloning, Pharmacological Characterization, and Anatomical Distribution of a Rat cDNA Encoding for a Galanin Receptor" *J. Molec. Neurosci.* (1995) 6: 33–41.

Chen, Y., et al., "Purification of a Galanin Receptor From Pig Brain" *PNAS* (USA) (1993) 90: 3845–3849.

Deecher, D.C., et al., "Galanin Receptors in Human Basal Forebrain Differ From Receptors in the Hypothalamus: Characterization Using [$^{125}$I]Galanin (Procine) and [$^{125}$I ]Galantide" *J. Pharmocol. Exp. Ther.* (1995) 275: 371–378.

Gu, Z.F., et al., "Interaction of Galanin Fragments With Galanin Receptors on Isolated Smooth Muscle Cells Guinea Pig Stomach: Identification of a Novel Galanin Receptor Subtype" *J. Pharmacol. Exp. Ther.* (1995) 272: 371–378.

Gustafon, E., et al., "Distribution of a Rat Galanin Receptor mRNA in Rat Brain" *Neuroreport* (1996) 7: 953–957.

Habert–Ortoli, E., et al., "Molecular Cloning of a Functional Human Galanin Receptor" *PNAS* (USA) (1994) 91: 9780–9783.

Heuillet, E., et al., The Human Galanin Receptor: Ligand Binding and Functional Characteristics in the Bowes Human Melanoma Cell Line: *Eur. J. Pharmacol.* (1994) 269: 139–147.

(List continued on next page.)

*Primary Examiner*—Michael Pak
(74) *Attorney, Agent, or Firm*—John P. White; Cooper & Dunham LLP

(57) ABSTRACT

This invention provides an isolated nucleic acid encoding a mammalian galanin receptor, an isolated galanin receptor protein, vectors comprising isolated nucleic acid encoding a mammalian galanin receptor, cells comprising such vectors, antibodies directed to a mammalian galanin receptor, nucleic acid probes useful for detecting nucleic acid encoding a mammalian galanin receptor, antisense oligonucleotides complementary to unique sequences of nucleic acid encoding a mammalian galanin receptor, nonhuman transgenic animals which express DNA encoding a normal or a mutant mammalian galanin receptor, as well as methods of determining binding of compounds to mammalian galanin receptors.

16 Claims, 16 Drawing Sheets

OTHER PUBLICATIONS

Kahl, U., et al., "Galanin Receptors" *DN& P* (1995) 8(7): 404–410.

Kask, K., et al., "Delineation of the Peptide Binding Site of the Human Galanin Receptor" *EMBO Journal* (1996) 15(2): 236–244.

Lorimer, D., et al., "Cloning and Quantification of Galanin–l Receptor Expression by Mucosal Cells Lining the Human Gastrointestinal Tract" *Biochem. Biophys. Res. Comm.* (1996) 222: 379–385.

Lorinet, A.M., et al., "Galanin REceptors in Human Hypothalamus: Biochemical and Structural Analysis" *Eur. J. Pharmacol.* (1994) 269: 59–64.

Marieb, E.N., (1992) *Human Anatomy And Physiology*, 2nd Edition, Redwood City, California, pp. 547–551.

O'Donnell, D., et al., "Neuroanatomical Distribution Of A Novel Rat Galanin Receptor Subtype" *Soc. Neurosci. Abstr.* (1996) 22(2): 1304, Abstract No. 517.9.

Parker, et al., "Cloning and Characterization of the Rat GALR1 Galanin Receptor From Rin14B Insulinoma Cells" *Molecular Brain Research* (1995) 34(2): 179–189.

Reeck, et al., "Homology In Porteins and Nucleic Acids: A Terminology Muddle And a Way Out Of It" *Cell* (1987) 50: 667.

Valkna, A., et al., "Differential Regulation of Adenylate Cyclase Activity in Rat Ventral and Dorasal Hippocampus by Rat Galanin" *Neurosci. Lett.* (1995) 187: 75–78.

Genbank Accession #Z82241, submitted Nov. 6, 1996, published Nov. 10, 1996.

Walli, R., et al., "Identification and Biochemical Characterization of the Human Brain Galanin Receptor" *J. Mil. Endocrinol.* (1994) 13: 347–356.

Watson, et al., *The G–Protein Linked Receptor Factbook*, Academic Press Limited (1994) San Diego, CA., pp. 2–6.

Wynick, D., et al., "Characterization of a High–Affinity Galanin Receptor in the Rat Anterior Pituitary: Absence of Biological Effect and Reduced Membrance Binding of the Antagonist M15 Differentiate it From the Brain/Gut Receptor" *PNAS* (USA) (1993) 90: 4231–4235; and.

Xu, et al., "New High Affinity Peptide Antagonists to the Spinal Galanin Receptor" *Br. J. Pharmacol.* (1995) 116: 2076–2080.

Wallace, et al., "Oligonucleotide probes for the screening of recombinant DNA libraries," Methods In Enzymology, Guide to Molecular Cloning Techniques, Berger et al. Eds, Academic Press (1987) 152:432–442.

Selve et al., "Galanin receptor antagonists attenuate spinal antinociceptive effects of DAMGO, tramadol and non–opioid drugs in rats," Brain Res. (Oct. 7, 1996) 735(2): 177–187; and.

Xu et al., "Expression of galanin and a galanin receptor in several sensory systems and bone anlage of rat embryos," Proc. Natl. Acad. Sci. (Dec. 1996) 93: 14901–14905.

Wang et al., "Molecular cloning and pharmacological characterization of a new galanin receptor subtype" *Mol. Pharm.* 52: 337–343 (Sep. 1997) (Exhibit B).

Wang et al., "Cloning and expressional characterization of a novel galanin receptor" *J. Biol. Chem. 272 (51)*: 31949–31952 (Dec. 19, 1997) (Exhibit C).

Genbank Accession No. AFO10318, published Sep. 30, 1997 (Exhibit D).

Genbank Accession No. AF031522, published Jul. 14, 1998 (Exhibit E).

Genbank Accession No. RNU94322, published Apr. 30, 1997.

Genbank Accession No. AFO08548, published Jul. 8, 1997.

FIGURE 1

1 AGCTCCAGCCTAGGCGTTCTACCTGGAAGAATGCAGGGGCCCAGTACCTAGGACTGAGGA 60
61 AGATGGCTGACATCCAGAACATTTCGCTGGACAGCCCAGGGAGCGTAGGGGCTGTGGCAG 120
121 TGCCTGTGATCTTTGCCCTCATCTTCCTGTTGGGCATGGTGGGCAATGGGCTGGTGTTGG 180
181 CTGTGCTACTGCAGCCTGGCCCAAGTGCCTGGCAGGAGCCAAGCAGTACCACAGATCTCT 240
241 TCATCCTCAACTTGGCCGTGGCCGACCTTTGCTTCATCCTGTGCTGCGTGCCCTTCCAGG 300
301 CAGCCATCTACACACTGGATGCCTGGCTCTTTGGGGCTTTCGTGTGCAAGACGGTACATC 360
361 TGCTCATCTACCTCACCATGTATGCCAGCAGCTTCACCCTGGCGGCCGTCTCCCTGGACA 420
421 GGTACCTGGCTGTGCGGCACCCACTGCGCTCCAGAGCCCTGCGCACCCCGCGCAACGCGC 480
481 GCGCCGCCGTGGGGCTCGTGTGGCTGCTGGCGGCTCTCTTTTCCGCGCCCTACCTAAGCT 540
541 ATTACGGCACGGTGCGCTACGGCGCGCTCGAGCTCTGCGTGCCCGCTTGGGAGGACGCGC 600
601 GGCGGCGCGCGCTGGACGTGGCCACCTTCGCCGCGGGCTACCTGCTGCCGGTGGCCGTGG 660
661 TGAGCCTGGCCTACGGACGCACGCTATGTTTCCTATGGGCCGCCGTGGGTCCCGCGGGCG 720
721 CGGCGGCAGCAGAGGCGCGCAGACGGGCGACCGGCCGGGCGGGACGCGCCATGCTGGCAG 780
781 TGGCCGCGCTCTACGCGCTTTGCTGGGGCCCGCACCACGCGCTCATCCTCTGCTTCTGGT 840
841 ACGGCCGCTTCGCCTTCAGCCCGGCCACCTACGCCTGTCGCCTGGCCTCGCACTGCCTCG 900
901 CCTACGCCAACTCCTGCCTTAACCCGCTCGTCTACTCGCTCGCCTCGCGCCACTTCCGCG 960
961 CGCGCTTCCGCCGCCTGTGGCCCTGCGGCCGTCGCCGCCACCGCCACCACCACCGCGCTC 1020
1021 ATCGAGCCCTCCGTCGTGTCCAGCCGGCGTCTTCGGGCCCCGCCGGTTATCCCGGCGACG 1080
1081 CCAGGCCTCGTGGTTGGAGTATGGAGCCCAGAGGGGATGCTCTGCGTGGTGGTGGAGAGA 1140
1141 CTAGACTAACCCTGTCCCCCAGGGGACCTCAATAACCCTGCCCGCTTGGACTCTGACGTC 1200
1201 TGTCAGAATGCCACCAAGGAACATCTAGGGAACGGCAGTCTCGCCAGGCTCCACCAAAAA 1260
1261 GCAGAAGCAAAGTTGCAGGG 1280

FIGURE 2

| | | | | | | | | | | | | | | | | | | | | | |
|---|---|---|---|---|---|---|---|---|---|---|---|---|---|---|---|---|---|---|---|---|---|
| 1 | M | A | D | I | Q | N | I | S | L | D | S | P | G | S | V | G | A | V | A | V | 20 |
| 21 | P | V | I | F | A | L | I | F | L | L | G | M | V | G | N | G | L | V | L | A | 40 |
| 41 | V | L | L | Q | P | G | P | S | A | W | Q | E | P | S | S | T | T | D | L | F | 60 |
| 61 | I | L | N | L | A | V | A | D | L | C | F | I | L | C | C | V | P | F | Q | A | 80 |
| 81 | A | I | Y | T | L | D | A | W | L | F | G | A | F | V | C | K | T | V | H | L | 100 |
| 101 | L | I | Y | L | T | M | Y | A | S | S | F | T | L | A | A | V | S | L | D | R | 120 |
| 121 | Y | L | A | V | R | H | P | L | R | S | R | A | L | R | T | P | R | N | A | R | 140 |
| 141 | A | A | V | G | L | V | W | L | L | A | A | L | F | S | A | P | Y | L | S | Y | 160 |
| 161 | Y | G | T | V | R | Y | G | A | L | E | L | C | V | P | A | W | E | D | A | R | 180 |
| 181 | R | R | A | L | D | V | A | T | F | A | A | G | Y | L | L | P | V | A | V | V | 200 |
| 201 | S | L | A | Y | G | R | T | L | C | F | L | W | A | A | V | G | P | A | G | A | 220 |
| 221 | A | A | A | E | A | R | R | R | A | T | G | R | A | G | R | A | M | L | A | V | 240 |
| 241 | A | A | L | Y | A | L | C | W | G | P | H | H | A | L | I | L | C | F | W | Y | 260 |
| 261 | G | R | F | A | F | S | P | A | T | Y | A | C | R | L | A | S | H | C | L | A | 280 |
| 281 | Y | A | N | S | C | L | N | P | L | V | Y | S | L | A | S | R | H | F | R | A | 300 |
| 301 | R | F | R | R | L | W | P | C | G | R | R | R | H | R | H | H | H | R | A | H | 320 |
| 312 | R | A | L | R | R | V | Q | P | A | S | S | G | P | A | G | Y | P | G | D | A | 340 |
| 341 | R | P | R | G | W | S | M | E | P | R | G | D | A | L | R | G | G | G | E | T | 360 |
| 361 | R | L | T | L | S | P | R | G | P | Q | | | | | | | | | | | 370 |

FIGURE 3

```
   1  CACTCAGCGATGACTTTGGCTCTGCTCTCCCCTCCTCCATCTCCCACGAGCTTCCAGCCC    60
  61  AGAACACCTGGCCAGACCCAGGTCGGGGGAGTTAGATCCCGGGGTCAAGCAACCAGAACT   120
 121  GGGGGCTCTTGCCTGAGGATTCCAGCTTCTCTTCCCAGGTGCCCGTCTGATGGGGAGATG   180
 181  GCTGATGCCCAGAACATTTCACTGGACAGCCCAGGGAGTGTGGGGGCCGTGGCAGTGCCT   240
 241  GTGGTCTTTGCCCTAATCTTCCTGCTGGGCACAGTGGGCAATGGGCTGGTGCTGGCAGTG   300
 301  CTCCTGCAGCCTGGCCCGAGTGCCTGGCAGGAGCCTGGCAGCACCACGGACCTGTTCATC   360
 361  CTCAACCTGGCGGTGGCTGACCTCTGCTTCATCCTGTGCTGCGTGCCCTTCCAGGCCACC   420
 421  ATCTACACGCTGGATGCCTGGCTCTTTGGGGCCCTCGTCTGCAAGGCCGTGCACCTGCTC   480
 481  ATCTACCTCACCATGTACGCCAGCAGCTTTACGCTGGCTGCTGTCTCCGTGGACAGGTAC   540
 541  CTGGCCGTGCGGCACCCGCTGCGCTCGCGCGCCCTGCGCACGCCGCGTAACGCCCGCGCC   600
 601  GCAGTGGGGCTGGTGTGGCTGCTGGCGGCGCTCTTCTCGGCGCCCTACCTCAGCTACTAC   660
 661  GGCACCGTGCGCTACGGCGCGCTGGAGCTCTGCGTGCCCGCCTGGGAGGACGCGCGCCGC   720
 721  CGCGCCCTGGACGTGGCCACCTTCGCTGCCGGCTACCTGCTGCCCGTGGCTGTGGTGAGC   780
 781  CTGGCCTACGGGCGCACGCTGCGCTTCCTGTGGGCCGCCGTGGGTCCCGCGGGCGCGGCG   840
 841  GCGGCCGAGGCGCGGCGGAGGGCGACGGGCCGCGCGGGGCGCGCCATGCTGGCGGTGGCC   900
 901  GCGCTCTACGCGCTCTGCTGGGGTCCGCACCACGCGCTCATCCTGTGCTTCTGGTACGGC   960
 961  CGCTTCGCCTTCAGCCCGGCCACCTACGCCTGCCGCCTGGCCTCACACTGCCTGGCCTAC  1020
1021  GCCAACTCCTGCCTCAACCCGCTCGTCTACGCGCTCGCCTCGCGCCACTTCCGCGCGCGC  1080
1081  TTCCGCCGCCTGTGGCCGTGCGGCCGCCGACGCCGCCACCGTGCCCGCCGCGCCTTGCGT  1140
1141  CGCGTCCGCCCCGCGTCCTCGGCCCACCCGGCTGCCCCGGAGACGCCCGGCCTAGCGGG  1200
1201  AGGCTGCTGGCTGGTGGCGGCCAGGGCCCGGAGCCCAGGGAGGGACCCGTCCACGGCGGA  1260
1261  GAGGCTGCCCGAGGACCGGAATAAACCCTGCCGCCTGGACTCCGCCTGTGTCCGTCTGTC  1320
1321  TCACTCCCGTTCTCCGAAGGCGGGACGCCACCGGGCCAGGGATGGGGCAATGCCACGAGC  1380
1381  TCTCTGAGGGGCGTTGAGTGGAGCGACTTGTCCCCGC                         1417
```

FIGURE 4

| | | | | | | | | | | | | | | | | | | | | | |
|---|---|---|---|---|---|---|---|---|---|---|---|---|---|---|---|---|---|---|---|---|---|
| 1 | H | S | A | M | T | L | A | L | L | S | P | P | P | S | P | T | S | F | Q | P | 20 |
| 21 | R | T | P | G | Q | T | Q | V | G | G | V | R | S | R | G | Q | A | T | R | T | 40 |
| 41 | G | G | S | C | L | R | I | P | A | S | L | P | R | C | P | S | D | G | E | M | 60 |
| 61 | A | D | A | Q | N | I | S | L | D | S | P | G | S | V | G | A | V | A | V | P | 80 |
| 81 | V | V | F | A | L | I | F | L | L | G | T | V | G | N | G | L | V | L | A | V | 100 |
| 101 | L | L | Q | P | G | P | S | A | W | Q | E | P | G | S | T | T | D | L | F | I | 120 |
| 121 | L | N | L | A | V | A | D | L | C | F | I | L | C | C | V | P | F | Q | A | T | 140 |
| 141 | I | Y | T | L | D | A | W | L | F | G | A | L | V | C | K | A | V | H | L | L | 160 |
| 161 | I | Y | L | T | M | Y | A | S | S | F | T | L | A | A | V | S | V | D | R | Y | 180 |
| 181 | L | A | V | R | H | P | L | R | S | R | A | L | R | T | P | R | N | A | R | A | 200 |
| 201 | A | V | G | L | V | W | L | L | A | A | L | F | S | A | P | Y | L | S | Y | Y | 220 |
| 221 | G | T | V | R | Y | G | A | L | E | L | C | V | P | A | W | E | D | A | R | R | 240 |
| 241 | R | A | L | D | V | A | T | F | A | A | G | Y | L | L | P | V | A | V | V | S | 260 |
| 261 | L | A | Y | G | R | T | L | R | F | L | W | A | A | V | G | P | A | G | A | A | 280 |
| 281 | A | A | E | A | R | R | R | A | T | G | R | A | G | R | A | M | L | A | V | A | 300 |
| 301 | A | L | Y | A | L | C | W | G | P | H | H | A | L | I | L | C | F | W | Y | G | 320 |
| 321 | R | F | A | F | S | P | A | T | Y | A | C | R | L | A | S | H | C | L | A | Y | 340 |
| 341 | A | N | S | C | L | N | P | L | V | Y | A | L | A | S | R | H | F | R | A | R | 360 |
| 361 | F | R | R | L | W | P | C | G | R | R | R | R | H | R | A | R | R | A | L | R | 380 |
| 381 | R | V | R | P | A | S | S | G | P | P | G | C | P | G | D | A | R | P | S | G | 400 |
| 401 | R | L | L | A | G | G | G | Q | G | P | E | P | R | E | G | P | V | H | G | G | 420 |
| 421 | E | A | A | R | G | P | E | | | | | | | | | | | | | | 440 |

FIGURE 5A

```
                                        I
                  ┌─────────────────────────────────────┐
hGALR3  . . . . . . . M A D A Q N I S L D S P G . . . . .  13
rGALR3  . . . . . . . M A D I Q N I S L D S P G . . . . .  13
rGALR1  M E L A P V N L S E G N G S D P E P P A E P R P L  25

hGALR3  . . . S V G A V A V P V V F A L I F L L G T V G N  35
rGALR3  . . . S V G A V A V P V I F A L I F L L G M V G N  35
rGALR1  F G I G V E N F I T L V V F G L I F A M G V L G N  50

hGALR3  G L V L A V L L Q P G P S A W Q E P G S T T D L F  60
rGALR3  G L V L A V L L Q P G P S A W Q E P S S T T D L F  60
rGALR1  S L V I T V L A R S K P G . . . K P R S T T N L F  72

                              II
hGALR3  I L N L A V A D L C F I L C C V P F Q A T I Y T L  85
rGALR3  I L N L A V A D L C F I L C C V P F Q A A I Y T L  85
rGALR1  I L N L S I A D L A Y L L F C I P F Q A T V Y A L  97
```

FIGURE 5B

```
                                                 III
hGALR3  D A W L F G A L V C K A V H L L I Y L T M Y A S S  110
rGALR3  D A W L F G A F V C K T V H L L I Y L T M Y A S S  110
rGALR1  P T W V L G A F I C K F I H Y F F T V S M L V S I  122

hGALR3  F T L A A V S V D R Y L A V R H P L R S R A L R T  135
rGALR3  F T L A A V S L D R Y L A V R H P L R S R A L R T  135
rGALR1  F T L A A M S V D R Y V A I V H S R R S S S L R V  147

                                    IV
hGALR3  P R N A R A A V G L V W L L A A L F S A P Y L S Y  160
rGALR3  P R N A R A A V G L V W L L A A L F S A P Y L S Y  160
rGALR1  S R N A L L G V G F I W A L S I A M A S P . V A Y  171

hGALR3  Y G T V . . R Y G A L E L C V P A W . E D A R R R  182
rGALR3  Y G T V . . R Y G A L E L C V P A W . E D A R R R  182
rGALR1  Y Q R L F H R D S N Q T F C W E H W P N Q L H K K  196
```

FIGURE 5C

```
                                   V
hGALR3  A L D V A T F A A G Y L L P V A V V S L A Y G R T   207
rGALR3  A L D V A T F A A G Y L L P V A V V S L A Y G R T   207
rGALR1  A Y V V C T F V F G Y L L P L L L I C F C Y A K V   221

hGALR3  L R F L W A A V G P A G A A A A E A R R R A T G R   232
rGALR3  L C F L W A A V G P A G A A A A E A R R R A T G R   232
rGALR1  L N H L H K K L K N M S K K S E A S K K . . . . K   242

                                      VI
hGALR3  A G R A M L A V A A L Y A L C W G P H H A L I L C   257
rGALR3  A G R A M L A V A A L Y A L C W G P H H A L I L C   257
rGALR1  T A Q T V L V V V V V F G I S W L P H H V I H L W   267

                                                VII
hGALR3  F W Y G R F A F S P A T Y A C R L A S H C L A Y A   282
rGALR3  F W Y G R F A F S P A T Y A C R L A S H C L A Y A   282
rGALR1  A E F G A F P L T P A S F F F R I T A H C L A Y S   292
```

FIGURE 5D

```
hGALR3  N S C L N P L V Y A L A S R H F R A R F R R L W P  307
rGALR3  N S C L N P L V Y S L A S R H F R A R F R R L W P  307
rGALR1  N S S V N P I I Y A F L S E N F R K A Y K Q V F K  317

hGALR3  C G R R R . . . R H R A R R A L R R V R P A S S G  329
rGALR3  C G R R R H R H H H R A H R A L R R V Q P A S S G  332
rGALR1  C R V C N E S P H G D A K E K N R I D T P P S T N  342

hGALR3  P P G C P G D A R P S G R L L A G G G Q G P E P R  354
rGALR3  P A G Y P G D A R P R G W S M . . . . . . . E P R  350
rGALR1  C T H V . . . . . . . . . . . . . . . . . . . . .  346

hGALR3  E G P V H G G E . . . . . . A A R G P E  368
rGALR3  G D A L R G G G E T R L T L S P R G P Q  370
```

DNA ENCODING GALANIN GALR3 RECEPTORS AND USES THEREOF

This application is a continuation of PCT International Application No. PCT/US97/18222, filed Oct. 9, 1997, which is a continuation-in-part of U.S. Ser. No. 08/900,230, filed Jul. 23, 1997, which is a continuation-in-part of U.S. Ser. No. 08/787,261, filed Jan. 24, 1997, now abandoned, which is a continuation-in-part of U.S. Ser. No. 08/767,964, filed Dec. 17, 1996 now abandoned, which is a continuation-in-part of U.S. Ser. No. 08/728,139, filed Oct. 9, 1996, now abandoned, the contents of all of which are hereby incorporated by reference into this application. Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the sequence listing and the claims.

BACKGROUND OF THE INVENTION

The neuropeptide galanin and its receptors hold great promise as targets for the development of novel therapeutic agents. Galanin is widely distributed throughout the peripheral and central nervous systems and is associated with the regulation of processes such as somatosensory transmission, smooth muscle contractility, hormone release, and feeding (for review, see Bartfai et al., 1993). In the periphery galanin is found in the adrenal medulla, uterus, gastrointestinal tract, dorsal root ganglia (DRG), and sympathetic neurons. Galanin released from sympathetic nerve terminals in the pancreas is a potent regulator of insulin release in several species (Ahrén and Lindskog, 1992; Boyle et al., 1994), suggesting a potential role for galanin in the etiology or treatment of diabetes. High levels of galanin are observed in human and rat anterior pituitary where galanin mRNA levels are potently upregulated by estrogen (Vrontakis et al., 1987; Kaplan et al., 1988). The presence of galanin in the hypothalamic-pituitary-adrenal axis coupled with its potent hormonal effects has led to the suggestion that galanin may play an integral role in the hormonal response to stress (Bartfai et al., 1993).

Within the CNS galanin-containing cell bodies are found in the hypothalamus, hippocampus, amygdala, basal forebrain, brainstem nuclei, and spinal cord, with highest concentrations of galanin in the hypothalamus and pituitary (Skofitsch and Jacobowitz, 1985; Bennet et al., 1991; Merchenthaler et al., 1993). The distribution of galanin receptors in the CNS generally complements that of galanin peptide, with high levels of galanin binding observed in the hypothalamus, amygdala, hippocampus, brainstem and dorsal spinal cord (Skofitsch et al., 1986; Merchenthaler et al., 1993; see Bartfai et al., 1993). Accordingly, agents modulating the activity of galanin receptors would have multiple potential therapeutic applications in the CNS. One of the most important of these is the regulation of food intake. Galanin injected into the paraventricular nucleus (PVN) of the hypothalamus stimulates feeding in satiated rats (Kyrkouli et al., 1990), an effect which is blocked by the peptide galanin antagonist M40 (Crawley et al., 1993). In freely feeding rats, PVN injection of galanin preferentially stimulates fat-preferring feeding (Tempel et al., 1988); importantly, the galanin antagonist M40 administered alone decreases overall fat intake (Leibowitz and Kim, 1992). These data indicate that specific receptors in the hypothalamus mediate the effects of galanin on feeding behavior, and further suggest that agents acting at hypothalamic galanin receptors may be therapeutically useful in the treatment of human eating disorders.

Galanin receptors elsewhere in the CNS may also serve as therapeutic targets. In the spinal cord galanin is released from the terminals of sensory neurons as well as spinal interneurons and appears to play a role in the regulation of pain threshold (Wiesenfeld-Hallin et al., 1992). Intrathecal galanin potentiates the anti-nociceptive effects of morphine in rats and produces analgesia when administered alone (Wiesenfeld-Hallin et al., 1993; Post et al., 1988); galanin receptor agonists may therefore be useful as analgesic agents in the spinal cord. Galanin may also play a role in the development of Alzheimer's disease. In the hippocampus galanin inhibits both the release (Fisone et al., 1987) and efficacy (Palazzi et al., 1988) of acetylcholine, causing an impairment of cognitive functions (Sundström et al., 1988). Autopsy samples from humans afflicted with Alzheimer's disease reveal a galaninergic hyperinnervation of the nucleus basalis (Chan-Palay, 1988), suggesting a role for galanin in the impaired cognition characterizing Alzheimer's disease. Together these data suggest that a galanin antagonist may be effective in ameliorating the symptoms of Alzheimer's disease (see Crawley, 1993). This hypothesis is supported by the report that intraventricular administration of the peptide galanin antagonist M35 improves cognitive performance in rats (Ögren et al., 1992). Human galanin receptors thus provide targets for therapeutic intervention in multiple CNS disorders.

High-affinity galanin binding sites have been characterized in brain, spinal cord, pancreatic islets and cell lines, and gastrointestinal smooth muscle in several mammalian species, and all show similar affinity for $^{125}$I-porcine galanin (~0.5–1 nM). Nevertheless, recent in vitro and in vivo pharmacological studies in which fragments and analogues of galanin were used suggest the existence of multiple galanin receptor subtypes. For example, a galanin binding site in guinea pig stomach has been reported that exhibits high affinity for porcine galanin (3–29) (Gu, et al. 1995), which is inactive at CNS galanin receptors. The chimeric galanin analogue M14 (galantide) acts as antagonist at CNS galanin receptors (Bartfai et al., 1991) but as a full agonist in gastrointestinal smooth muscle (Gu et al., 1993). Similarly, the galanin-receptor ligand M40 acts as a weak agonist in RINm5F insulinoma cells and a full antagonist in brain (Bartfai et al, 1993a). The pharmacological profile of galanin receptors in RINm5F cells can be further distinguished from those in brain by the differential affinities of [D-Tyr$^2$]- and [D-Phe$^2$]-galanin analogues (Lagny-Pourmir et al., 1989). The chimeric galanin analogue M35 displaces $^{125}$I-galanin binding to RINm5F membranes in a biphasic manner, suggesting the presence of multiple galanin receptor subtypes, in this cell line (Gregersen et al., 1993).

Multiple galanin receptor subtypes may also co-exist within the CNS. Galanin receptors in the dorsal hippocampus exhibit high affinity for Gal (1–15) but not for Gal (1–29) (Hedlund et al., 1992), suggesting that endogenous proteolytic processing may release bioactive fragments of galanin to act at distinct receptors. The rat pituitary exhibits high-affinity binding for $^{125}$I-Bolton and Hunter (N-terminus)-labeled galanin (1–29) but not for [$^{125}$I]Tyr$^{26}$-porcine galanin (Wynick et al., 1993), suggesting that the pituitary galanin receptor is a C-terminus-preferring subtype. Spinal cord galanin binding sites, while similar to those in brain, show an affinity for the chimeric peptide antagonist M35 intermediate between the brain and smooth muscle (Bartfai et al., 1991), raising the possibility of further heterogeneity.

A galanin receptor cDNA was recently isolated by expression cloning from a human Bowes melanoma cell line (Habert-Ortoli et al., 1994). The pharmacological profile exhibited by this receptor is similar to that observed in brain and pancreas, and on that basis the receptor has been termed GALR1. The cloned human GALR1 receptor ("hGALR1") binds native human, porcine and rat galanin with ~1 nM affinity ($K_i$ vs. $^{125}$I-galanin) and porcine galanin 1–16 at a slightly lower affinity (~5nM). Porcine galanin 3–29 does not bind to the receptor. The GALR1 receptor appears to couple to inhibition of adenylate cyclase, with half-maximal inhibition of forskolin-stimulated cAMP production by 1 nM galanin, and maximal inhibition occurring at about 1 $\mu$M.

Recently the rat homologue of GALR1 ("rGALR1") was cloned from the RIN14B pancreatic cell line (Burgevin, et al., (1995), Parker et al., 1995. The pharmacologic data reported to date do not suggest substantial differences between the pharmacologic properties of the rat and human GALR1 receptors. Localization studies reveal GALR1 mRNA in rat hypothalamus, ventral hippocampus, brainstem, and spinal cord (Gustafson et al., 1996), regions consistent with roles for galanin in feeding, cognition, and pain transmission. However, GALR1 appears to be distinct from the pituitary and hippocampal receptor subtypes described above.

The indication of multiple galanin receptor subtypes within the brain underscores the importance of defining galanin receptor heterogeneity at the molecular level in order to develop specific therapeutic agents for CNS disorders. Pharmacological tools capable of distinguishing galanin receptor subtypes in tissue preparations are only beginning to appear. Several high-affinity peptide-based galanin antagonists have been developed and are proving useful in probing the functions of galanin receptors (see Bartfai et al., 1993), but their peptide character precludes practical use as therapeutic agents. In light of galanin's multiple neuroendocrine roles, therapeutic agents targeting a specific disorder must be selective for the appropriate receptor subtype to minimize side effects.

Accordingly, applicants have endeavored to clone the entire family of galanin receptors for use in target-based drug design programs. The identification of non-peptide agents acting selectively only at specific galanin receptors will be greatly facilitated by the cloning, expression, and characterization of the galanin receptor family.

Applicants have recently isolated by expression cloning from a rat hypothalamic cDNA library a novel galanin receptor, termed "GALR2," not described herein, which is distinguishable from GALR1 both by its unique sequence and distinct pharmacologic properties. The GALR2 receptor is the subject of PCT International Application PCT/US97/01301, published on Jul. 31, 1997, as WO 97/26853.

Applicants now report the isolation of a novel galanin receptor subtype, referred to herein as "GALR3," from a rat hypothalamic cDNA library. This discovery provides a novel approach, through the use of heterologous expression systems, to develop subtype selective, high-affinity non-peptide compounds that could serve as therapeutic agents for eating disorders, diabetes, pain, depression, ischemia, Alzheimer's disease, neuroendocrine disorders. The distribution of mRNA encoding the rat GALR3 receptor in multiple CNS regions as well as other organs supports the notion that the rat GALR3 is involved in these disorders. Pathophysiological disorders proposed to be linked to galanin receptor activation include eating disorders, diabetes, pain, depression, ischemia, Alzheimer's disease and reproductive disorders. Accordingly, treatment of such disorders may be effected by the administration of GALR3 receptor-selective compounds. The presence of galanin binding sites in multiple CNS areas suggests that GALR3 receptors may also play a role in cognition, analgesia, sensory processing (olfactory, visual), processing of visceral information, motor coordination, modulation of dopaminergic activity, neuroendocrine function, sleep disorders, migraine, and anxiety.

SUMMARY OF THE INVENTION

This invention provides an isolated nucleic acid encoding a GALR3 galanin receptor. This invention also provides an isolated GALR3 receptor protein. This invention also provides a purified GALR3 receptor protein. This invention further provides DNA, cDNA, genomic DNA, RNA, and mRNA encoding the GALR3 receptor.

This invention further provides a vector comprising the GALR3 receptor. Such a vector may be adapted for expression of the GALR3 receptor in mammalian or non-mammalian cells. This invention also provides a plasmid which comprises the regulatory elements necessary for expression of GALR3 nucleic acid in a mammalian cell operatively linked to a nucleic acid encoding the GALR3 receptor so as to permit expression thereof, designated K1086 (ATCC Accession No. 97747). This invention also provides a plasmid which comprises the regulatory elements necessary for expression of GALR3 nucleic acid in a mammalian cell operatively linked to a nucleic acid encoding a human GALR3 receptor so as to permit expression thereof, designated pEXJ-hGalR3 (ATCC Accession No. 97827). This invention provides mammalian cells comprising the above-described plasmid or vector. This invention also provides a membrane preparation isolated from the cells.

This invention provides an isolated nucleic acid encoding a modified GALR3 receptor, which differs from a GALR3 receptor by having an amino acid(s) deletion, replacement or addition in the third intracellular domain.

This invention provides a nucleic acid probe comprising at least 15 nucleotides, which probe specifically hybridizes with a nucleic acid encoding a GALR3 receptor, wherein the probe has a unique sequence corresponding to a sequence present within one of the two strands of the nucleic acid encoding the GALR3 receptor contained in plasmid K1086. This invention still further provides a nucleic acid probe comprising at least 15 nucleotides, which probe specifically hybridizes with a nucleic acid encoding a GALR3 receptor, wherein the probe has a unique sequence corresponding to a sequence present within (a) the nucleic acid sequence described in FIG. 1 (Seq. ID No: 1) or (b) the reverse complement to the nucleic acid sequence shown in FIG. 1 (Seq. ID No: 1).

In yet another embodiment, the GALR3 receptor is the rat GALR3 receptor having substantially the same amino acid sequence as the amino acid sequence shown in FIG. 2. In another embodiment, the GALR3 receptor is the rat GALR3 receptor having the amino acid sequence shown in FIG. 2. In another embodiment, the GALR3 receptor is the human GALR3 receptor. In another embodiment, the GALR3 receptor is the human GALR3 receptor encoded by the coding sequence of plasmid pEXJ-hGalR3. This invention also provides a nucleic acid probe comprising at least 15 nucleotides, which probe specifically hybridizes with a nucleic acid encoding a GALR3 receptor, wherein the probe has a unique sequence corresponding to a sequence present within one of the two strands of the nucleic acid encoding the GALR3 receptor contained in plasmid pEXJ-hGalR3. This invention provides a nucleic acid probe comprising at least 15 nucleotides, which probe specifically hybridizes with a nucleic acid encoding a GALR3 receptor, wherein the probe has a unique sequence corresponding to a sequence present within (a) the nucleic acid sequence described in FIG. 3 (Seq. ID No: 3) or (b) the reverse complement to the nucleic acid sequence shown in FIG. 3 (Seq. ID No: 3).

This invention further provides a nucleic acid probe comprising a nucleic acid molecule of at least 15 nucleotides which is complementary to a unique fragment of the sequence of a nucleic acid molecule encoding a GALR3 receptor.

This invention also provides a nucleic acid probe comprising a nucleic acid molecule of at least 15 nucleotides which is complementary to the antisense sequence of a unique fragment of the sequence of a nucleic acid molecule encoding a GALR3 receptor.

This invention provides an antisense oligonucleotide having a sequence capable of specifically hybridizing to mRNA encoding a GALR3 galanin receptor, so as to prevent translation of the mRNA. This invention also provides an antisense oligonucleotide having a sequence capable of specifically hybridizing to the genomic DNA molecule encoding a GALR3 receptor.

This invention provides an antibody directed to a GALR3 receptor. This invention also provides a monoclonal antibody directed to an epitope of a GALR3 receptor, which epitope is present on the surface of a cell expressing a GALR3 receptor.

This invention provides a pharmaceutical composition comprising an amount of the oligonucleotide effective to reduce activity of a GALR3 receptor by passing through a cell membrane and binding specifically with mRNA encoding a GALR3 receptor in the cell so as to prevent its translation and a pharmaceutically acceptable carrier capable of passing through a cell membrane. In an embodiment, the oligonucleotide is coupled to a substance which inactivates mRNA. In another embodiment, the substance which inactivates mRNA is a ribozyme.

This invention provides a pharmaceutical composition comprising an amount of an antagonist effective to reduce the activity of a GALR3 receptor and a pharmaceutically acceptable carrier.

This invention provides a pharmaceutical composition comprising an amount of an agonist effective to increase activity of a GALR3 receptor and a pharmaceutically acceptable carrier.

This invention provides a transgenic nonhuman mammal expressing DNA encoding a GALR3 receptor. This invention provides a transgenic nonhuman mammal comprising a homologous recombination knockout of the native GALR3 receptor. This invention provides a transgenic nonhuman mammal whose genome comprises antisense DNA complementary to DNA encoding a GALR3 receptor so placed as to be transcribed into antisense mRNA which is complementary to mRNA encoding a GALR3 receptor and which hybridizes to mRNA encoding a GALR3 receptor thereby reducing its translation.

This invention also provides a process for determining whether a compound can specifically bind to a GALR3 receptor which comprises contacting a cell transfected with and expressing DNA encoding the GALR3 receptor with the compound under conditions permitting binding of compounds to such receptor, and detecting the presence of any such compound specifically bound to the GALR3 receptor, so as to thereby determine whether the ligand specifically binds to the GALR3 receptor.

This invention provides a process for determining whether a compound can specifically bind to a GALR3 receptor which comprises preparing a cell extract from cells transfected with and expressing DNA encoding the GALR3 receptor, isolating a membrane fraction from the cell extract, contacting the membrane fraction with the compound under conditions permitting binding of compounds to such receptor, and detecting the presence of the compound specifically bound to the GALR3 receptor, so as to thereby determine whether the compound specifically binds to the GALR3 receptor.

In one embodiment, the GALR3 receptor is a mammalian GALR3 receptor. In another embodiment, the GALR3 receptor is a rat GALR3 receptor. In still another embodiment, the GALR3 receptor has substantially the same amino acid sequence encoded by the plasmid K1086. In a still further embodiment, the GALR3 receptor has the amino acid sequence encoded by the plasmid K1086. In another embodiment, the GALR3 receptor is a human GALR3 receptor.

This invention provides a process for determining whether a compound is a GALR3 receptor agonist which comprises contacting a cell transfected with and expressing DNA encoding the GALR3 receptor with the compound under conditions permitting the activation of the GALR3 receptor, and detecting an increase in GALR3 receptor activity, so as to thereby determine whether the compound is a GALR3 receptor agonist.

This invention provides a process for determining whether a compound is a GALR3 receptor antagonist which comprises contacting a cell transfected with and expressing DNA encoding the GALR3 receptor with the compound in the presence of a known GALR3 receptor agonist, such as galanin, under conditions permitting the activation of the GALR3 receptor, and detecting a decrease in GALR3 receptor activity, so as to thereby determine whether the compound is a GALR3 receptor antagonist.

This invention provides a compound determined by the above-described processes. In one embodiment of the above-described processes, the compound is not previously known. In another embodiment, the compound is not known to bind a GALR3 receptor.

This invention provides a method of screening a plurality of chemical compounds not known to bind to a GALR3 receptor to identify a compound which specifically binds to the GALR3 receptor, which comprises (a) contacting cells transfected with and expressing DNA encoding the GALR3 receptor with a compound known to bind specifically to the GALR3 receptor; (b) contacting the preparation of step (a) with the plurality of compounds not known to bind specifically to the GALR3 receptor, under conditions permitting binding of compounds known to bind the GALR3 receptor; (c) determining whether the binding of the compound known to bind to the GALR3 receptor is reduced in the presence of the compounds, relative to the binding of the compound in the absence of the plurality of compounds; and if so (d) separately determining the binding to the GALR3 receptor of each compound included in the plurality of compounds, so as to thereby identify the compound which specifically binds to the GALR3 receptor.

This invention provides a method of screening a plurality of chemical compounds not known to activate a GALR3 receptor to identify a compound which activates the GALR3 receptor which comprises (a) contacting cells transfected with and expressing the GALR3 receptor with the plurality of compounds not known to activate the GALR3 receptor, under conditions permitting activation of the GALR3 receptor; (b) determining whether the activity of the GALR3 receptor is increased in the presence of the compounds; and if so (c) separately determining whether the activation of the GALR3 receptor is increased by each compound included in the plurality of compounds, so as to thereby identify the compound which activates the GALR3 receptor.

This invention provides a method of screening a plurality of chemical compounds not known to inhibit the activation of a GALR3 receptor to identify a compound which inhibits the activation of the GALR3 receptor, which comprises (a) preparing a cell extract from cells transfected with and expressing DNA encoding the GALR3 receptor, isolating a membrane fraction from the cell extract, contacting the membrane fraction with the plurality of compounds in the presence of a known GALR3 receptor agonist, under conditions permitting activation of the GALR3 receptor; (b) determining whether the activation of the GALR3 receptor is reduced in the presence of the plurality of compounds, relative to the activation of the GALR3 receptor in the absence of the plurality of compounds; and if so (c) separately determining the inhibition of activation of the GALR3 receptor for each compound included in the plurality of compounds, so as to thereby identify the compound which inhibits the activation of the GALR3 receptor.

This invention provides a method of detecting expression of a GALR3 receptor by detecting the presence of mRNA coding for the GALR3 receptor which comprises obtaining total mRNA from the cell and contacting the mRNA so obtained with the above-described nucleic acid probe under hybridizing conditions, detecting the presence of mRNA hybridized to the probe, and thereby detecting the expression of the GALR3 receptor by the cell.

This invention provides a method of treating an abnormality in a subject, wherein the abnormality is alleviated by the inhibition of a GALR3 receptor which comprises administering to a subject an effective amount of the above-described pharmaceutical composition effective to decrease the activity of the GALR3 receptor in the subject, thereby treating the abnormality in the subject. In an embodiment, the abnormality is obesity. In another embodiment, the abnormality is bulimia.

This invention provides a method of treating an abnormality in a subject wherein the abnormality is alleviated by the activation of a GALR3 receptor which comprises administering to a subject an effective amount of the above-described pharmaceutical composition effective to activate the GALR3 receptor in the subject. In an embodiment, the abnormal condition is anorexia.

This invention provides a method for diagnosing a predisposition to a disorder associated with the activity of a specific human GALR3 receptor allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human GALR3 receptor and labeled with a detectable marker; (e) detecting labeled bands which have hybridized to DNA encoding a human GALR3 receptor labeled with a detectable marker to create a unique band pattern specific to the DNA of subjects suffering from the disorder; (f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of modifying feeding behavior of a subject which comprises administering to the subject an amount of a compound which is a galanin receptor agonist or antagonist effective to increase or decrease the consumption of food by the subject so as to thereby modify feeding behavior of the subject. In an embodiment, the compound is a GALR3 receptor antagonist and the amount is effective to decrease the consumption of food by the subject. In another embodiment the compound is administered in combination with food.

In yet another embodiment the compound is a GALR3 receptor agonist and the amount is effective to increase the consumption of food by the subject. In a still further embodiment, the compound is administered in combination with food. In other embodiments the subject is a vertebrate, a mammal, a human or a canine.

This invention provides a process for determining whether a chemical compound is a GALR3 receptor agonist, which comprises preparing a cell extract from cells transfected with and expressing DNA encoding the GALR3 receptor, isolating a membrane fraction from the cell extract, separately contacting the membrane fraction with both the chemical compound and GTPγS, and with only GTPγS, under conditions permitting the activation of the GALR3 receptor, and detecting GTPγS binding to the membrane fraction, an increase in GTPγS binding in the presence of the compound indicating that the chemical compound activates the GALR3 receptor.

This invention provides a process for determining whether a chemical compound is a GALR3 receptor antagonist, which comprises preparing a cell extract from cells transfected with and expressing DNA encoding the GALR3 receptor, isolating a membrane fraction from the cell extract, separately contacting the membrane fraction with the chemical compound, GTPγS and a second chemical compound known to activate the GALR3 receptor, with GTPγS and only the second compound, and with GTPγS alone, under conditions permitting the activation of the GALR3 receptor, detecting GTPγS binding to each membrane fraction, and comparing the increase in GTPγS binding in the presence of the compound and the second compound relative to the binding of GTPγS alone, to the increase in GTPγS binding in the presence of the second chemical compound relative to the binding of GTPγS alone, a smaller increase in GTPγS binding in the presence of the compound and the second compound indicating that the compound is a GALR3 receptor antagonist.

This invention further provides a process for identifying a chemical compound which specifically binds to a GALR3 receptor which comprises contacting cells containing DNA encoding and expressing on their cell surface the GALR3 receptor, wherein such cells do not normally express the GALR3 receptor, with the compound under conditions suitable for binding, and detecting specific binding of the chemical compound to the GALR3 receptor.

This invention also provides a process for identifying a chemical compound which specifically binds to a GALR3 receptor which comprises contacting a membrane fraction from a cell extract of cells containing DNA encoding and expressing on their cell surface the GALR3 receptor, wherein such cells do not normally express the GALR3 receptor, with the compound under conditions suitable for binding, and detecting specific binding of the chemical compound to the GALR3 receptor.

This invention provides a process involving competitive binding for identifying a chemical compound which specifically binds to a GALR3 receptor which comprises separately contacting cells expressing on their cell surface the GALR3 receptor, wherein such cells do not normally express the GALR3 receptor, with both the chemical compound and a second chemical compound known to bind to the receptor, and with only the second chemical compound, under conditions suitable for binding of both compounds, and detecting specific binding of the chemical compound to the GALR3 receptor, a decrease in the binding of the second chemical compound to the GALR3 receptor in the presence of the chemical compound indicating that the chemical compound binds to the GALR3 receptor.

This invention further provides a process involving competitive binding for identifying a chemical compound which specifically binds to a human GALR3 receptor which comprises separately contacting a membrane fraction from a cell extract of cells expressing on their cell surface the GALR3 receptor, wherein such cells do not normally express the GALR3 receptor, with both the chemical compound and a second chemical compound known to bind to the receptor, and with only the second chemical compound, under conditions suitable for binding of both compounds, and detecting specific binding of the chemical compound to the GALR3 receptor, a decrease in the binding of the second chemical compound to the GALR3 receptor in the presence of the chemical compound indicating that the chemical compound binds to the GALR3 receptor.

This invention provides a method of screening a plurality of chemical compounds not known to bind to a GALR3 receptor to identify a compound which specifically binds to the GALR3 receptor, which comprises (a) preparing a cell extract from cells transfected with and expressing DNA encoding the GALR3 receptor, isolating a membrane fraction from the cell extract, contacting the membrane fraction with a compound known to bind specifically to the GALR3 receptor; (b)contacting the preparation of step (a) with the plurality of compounds not known to bind specifically to the GALR3 receptor, under conditions permitting binding of compounds known to bind the GALR3 receptor; (c) determining whether the binding of the compound known to bind to the GALR3 receptor is reduced in the presence of the compounds, relative to the binding of the compound in the absence of the plurality of compounds; and if so (d) separately determining the binding to the GALR3 receptor of each compound included in the plurality of compounds, so as to thereby identify the compound which specifically binds to the GALR3 receptor.

This invention provides a method for determining whether a compound is a GALR3 antagonist which comprises: (a) administering to an animal a GALR3 agonist and measuring the amount of food intake in the animal; (b) administering to a second animal both the GALR3 agonist and the compound, and measuring the amount of food intake in the second animal; and (c) determining whether the amount of food intake is reduced in the presence of the compound relative to the amount of food intake in the absence of the compound, so as to thereby determine whether the compound is a GALR3 antagonist.

This invention provides a method of screening a plurality of compounds to identify a compound which is a GALR3 antagonist which comprises: (a) administering to an animal a GALR3 agonist and measuring the amount of food intake in the animal; (b) administering to a second animal the GALR3 agonist and at least one compound of the plurality of compounds and measuring the amount of food intake in the animal; (c) determining whether the amount of food intake is reduced in the presence of at least one compound of the plurality relative to the amount of food intake in the absence of at least one compound of the plurality, and if so; (d) separately determining whether each compound is a GALR3 antagonist according to the method of claim 118, so as to thereby identify a compound which is a GALR3 antagonist.

This invention further provides a method of decreasing feeding behavior of a subject which comprises administering a compound which is a GALR3 receptor antagonist and a compound which is a Y5 receptor antagonist, the amount of such antagonists being effective to decrease the feeding behavior of the subject.

This invention provides a method of decreasing nociception in a subject which comprises administering to the subject an amount of a compound which is a GALR3 receptor agonist effective to decrease nociception in the subject.

This invention also provides a method of treating pain in a subject which comprises administering to the subject an amount of a compound which is a GALR3 receptor agonist effective to treat pain in the subject.

This invention further provides a method of treating diabetes in a subject which comprises administering to the subject an amount of a compound which is a GALR3 receptor antagonist effective to treat diabetes in the subject.

This invention also provides a process for determining whether a chemical compound specifically binds to and activates a GALR3 receptor, which comprises contacting cells producing a second messenger response and expressing on their cell surface the GALR3 receptor, wherein such cells do not normally express the GALR3 receptor, with the chemical compound under conditions suitable for activation of the GALR3 receptor, and measuring the second messenger response in the presence and in the absence of the chemical compound, a change in the second messenger response in the presence of the chemical compound indicating that the compound activates the GALR3 receptor.

This invention provides a process for determining whether a chemical compound specifically binds to and inhibits activation of a GALR3 receptor, which comprises separately contacting cells producing a second messenger response and expressing on their cell surface the GALR3 receptor, wherein such cells do not normally express the GALR3 receptor, with both the chemical compound and a second chemical compound known to activate the GALR3 receptor, and with only the second chemical compound, under conditions suitable for activation of the GALR3 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR3 receptor.

This invention provides a method of screening a plurality of chemical compounds not known to activate a GALR3 receptor to identify a compound which activates the GALR3 receptor which comprises: (a) contacting cells transfected with and expressing the GALR3 receptor with the plurality of compounds not known to activate the GALR3 receptor, under conditions permitting activation of the GALR3 receptor; (b) determining whether the activity of the GALR3 receptor is increased in the presence of the compounds; and if so (c) separately determining whether the activation of the GALR3 receptor is increased by each compound included in the plurality of compounds, so as to thereby identify the compound which activates the GALR3 receptor.

This invention provides a method of screening a plurality of chemical compounds not known to inhibit the activation of a GALR3 receptor to identify a compound which inhibits the activation of the GALR3 receptor, which comprises: (a) contacting cells transfected with and expressing the GALR3 receptor with the plurality of compounds in the presence of a known GALR3 receptor agonist, under conditions permitting activation of the GALR3 receptor; (b) determining whether the activation of the GALR3 receptor is reduced in the presence of the plurality of compounds, relative to the activation of the GALR3 receptor in the absence of the plurality of compounds; and if so (c) separately determining the inhibition of activation of the GALR3 receptor for each compound included in the plurality of compounds, so as to thereby identify the compound which inhibits the activation of the GALR3 receptor.

This invention provides a process for determining whether a chemical compound is a GALR3 receptor antagonist, which comprises preparing a cell extract from cells transfected with and expressing DNA encoding the GALR3 receptor, isolating a membrane fraction from the cell extract, separately contacting the membrane fraction with the chemical compound, GTPγS and a second chemical compound known to activate the GALR3 receptor, with GTPγS and only the second compound, and with GTPγS alone, under conditions permitting the activation of the GALR3 receptor, detecting GTPγS binding to each membrane fraction, and comparing the increase in GTPγS binding in the presence of the compound and the second compound relative to the binding of GTPγS alone, to the increase in GTPγS binding in the presence of the second chemical compound relative to the binding of GTPγS alone, a smaller increase in GTPγS binding in the presence of the compound and the second compound indicating that the compound is a GALR3 receptor antagonist.

BRIEF DESCRIPTION OF THE FIGURES

FIG. 1 Nucleotide coding sequence of the rat hypothalamic galanin GALR3 receptor (Seq. I.D. No: 1), with partial 5' and 3' untranslated sequences. Start and stop codons are underlined.

FIG. 2 Deduced amino acid sequence of the rat hypothalamic galanin GALR3 receptor (Seq. I.D. No: 2) encoded by the rat nucleotide sequence shown in FIG. 1.

FIG. 3 Nucleotide coding sequence of the human galanin GALR3 receptor (Seq. I.D. No: 3), with partial 5' and 3' untranslated sequences. Start and stop codons are underlined.

FIG. 4 Deduced amino acid sequence of the human galanin GALR3 receptor (Seq. I.D. No: 4) encoded by the human nucleotide sequence shown in FIG. 3. The nucleotide sequence shown in FIG. 3 is translated from nucleotide 1 to the stop codon. Two possible starting methionines are underlined.

FIGS. 5A–5D Amino acid sequence alignment of the rat GALR3 receptor (top row) (Seq. ID No: 2), human GALR3 receptor (middle row) (Seq. ID No: 4) and rat GALR1 receptor (bottom row) (Seq. ID No: 5). Transmembrane domains (TM 1–7) are indicated by brackets above the sequence.

FIG. 6B: Concentration-response characteristic of a second oocyte expressing both hGalR3 and GIRKs. Stepwise increases in the concentration of porcine galanin from 10 to 10,000 nM result in a saturable increase in inward current.

FIG. 8A: M32; FIG. 8B: porcine galanin; FIG. 8C: C7; FIG. 8D: Gal −7–29; FIG. 8E: Gal 1–16; FIG. 8F: M40; FIG. 8G: human galanin. Measurements of GIRK currents were made as shown for galanin in FIG. 6B. For all peptides, responses from 3–6 oocytes were averaged for each data point. Curves were fitted with the logistic equation $I=Imax/(1+(EC_{50}/[Agonist])^n)$, where $EC_{50}$ is the concentration of agonist that produced half-maximal activation, and n the Hill coefficient. Fits were made with a Marquardt-Levenberg non-linear least-squares curve fitting algorithm.

FIG. 9B: the galanin-sensitive current ($I_{gal}$) was derived by subtracting the background current (½ hK) from the galanin current (+gal); the total inward rectifier current ($I_{tot}$) was similarly obtained by subtracting the current in the presence of $Ba^{++}$ from the galanin current. Both $I_{gal}$ and $I_{tot}$ display steep inward rectification and reverse at approximately −24 mV.

DETAILED DESCRIPTION OF THE INVENTION

Figure 6A:
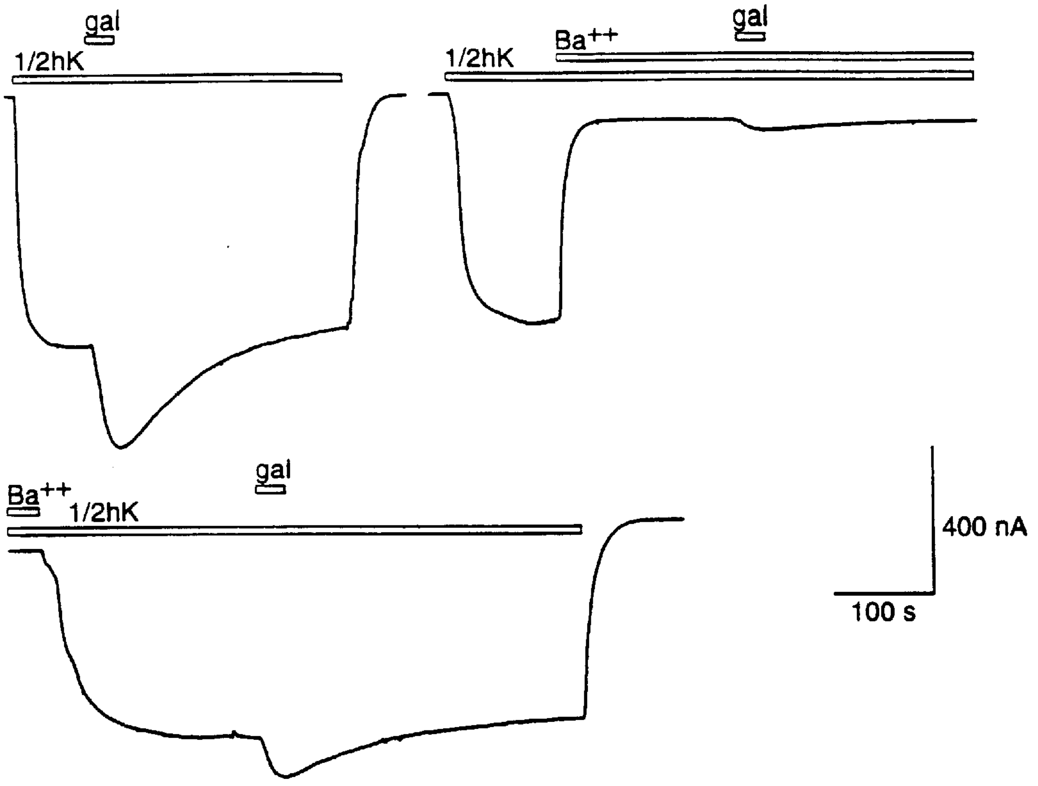
FIGS. 6A–6B FIG. 6A: Long continuous trace (3 segments) demonstrates galanin responsivity and sensitivity to $Ba^{++}$ block in an oocyte expressing hGalR3 and GIRK1 and GIRK4. Switching from ND96 to ½ hK solution causes the appearance of a large resting (inward) $K^+$ current that increases further upon transient addition of 3 $\mu$M galanin. Subsequent addition of 300 $\mu$M $Ba^{++}$ largely blocks both the resting and galanin-stimulated $K^+$ currents. After removal of $Ba^{++}$ galanin responsivity is partially restored.

Throughout this application, the following standard abbreviations are used to indicate specific nucleotide bases:

| | |
|---|---|
| C = cytosine | A = adenine |
| T = thymine | G = guanine |

Furthermore, the term "agonist" is used throughout this application to indicate any peptide or non-peptidyl compound which increases the activity of any of the receptors of the subject invention. The term "antagonist" is used throughout this application to indicate any peptide or non-peptidyl compound which decreases the activity of any of the receptors of the subject invention.

The activity of a G-protein coupled receptor such as a galanin receptor may be measured using any of a variety of functional assays which are well-known in the art, in which activation of the receptor in question results in an observable change in the level of some second messenger, including but not limited to adenylate cyclase, calcium mobilization, arachidonic acid release, ion channel activity, inositol phospholipid hydrolysis or guanylyl cyclase. Heterologous expression systems utilizing appropriate host cells to express the nucleic acid of the subject invention are used to obtain the desired second messenger coupling. Receptor activity may also be assayed in an oocyte expression system, using methods well known in the art.

This invention provides an isolated nucleic acid encoding a GALR3 galanin receptor. This invention further provides a recombinant nucleic acid encoding a GALR3 galanin receptor. In an embodiment, the galanin receptor is a vertebrate or a mammalian GALR3 receptor. In another embodiment, the galanin receptor is a rat GALR3 receptor. In another embodiment, the galanin receptor is a human GALR3 receptor. In an embodiment, the isolated nucleic acid encodes a receptor characterized by an amino acid sequence in the transmembrane region, which has a homology of 70% or higher to the amino acid sequence in the transmembrane region of the rat galanin GALR3 receptor and a homology of less than 70% to the amino acid sequence in the transmembrane region of any GALR1 receptor. In an embodiment, the GALR3 receptor is a rat GALR3 receptor. In another embodiment, the GALR3 receptor is a human GALR3 receptor.

This invention provides an isolated nucleic acid encoding a GALR3 receptor having the same or substantially the same amino acid sequence as the amino acid sequence encoded by the plasmid K1086 (ATCC Accession No. 97747). In an embodiment, the nucleic acid is DNA. This invention further provides an isolated nucleic acid encoding a rat GALR3 receptor having the amino acid sequence encoded by the plasmid K1086. This invention provides an isolated nucleic acid encoding a GALR3 receptor having substantially the same amino acid sequence as the amino acid sequence shown in FIG. 2 (Seq. I.D. No: 2). In another embodiment, the GALR3 receptor is the rat GALR3 receptor having the amino acid sequence shown in FIG. 2 (Seq. ID NO: 2). In another embodiment, the nucleic acid comprises at least an intron. In still another embodiment, the nucleic acid comprises alternately spliced nucleic acid transcribed from the nucleic acid contained in plasmid K1086. In an embodiment, the alternately spliced nucleic acid is mRNA transcribed from DNA encoding a galanin receptor.

In an embodiment, the GALR3 receptor is a human GALR3 receptor. This invention provides an isolated nucleic acid encoding a human GALR3 receptor having the same or substantially the same amino acid sequence as the amino acid sequence encoded by plasmid pEXJ-hGalR3 (ATCC Accession No. 97827). This invention provides an isolated nucleic acid encoding a human GALR3 receptor, wherein the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO: 4) from amino acid 60 through amino acid 427.

In another embodiment, the nucleic acid encoding the human GALR3 receptor comprises an intron. In still another embodiment, the nucleic acid encoding the human GALR3 receptor comprises alternately spliced nucleic acid.

The fact that introns are found in many G protein coupled receptors raises the possibility that introns could exist in coding or non-coding regions of GALR3; if so, a spliced form of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene (Burns et al., 1996; Chu et al., 1996). Such variants may exhibit pharmacologic properties differing from the receptor encoded by the original gene.

This invention provides a splice variant of the GALR3 receptors disclosed herein. This invention further provides for alternate translation initiation sites and alternately spliced or edited variants of nucleic acids encoding rat and human GALR3 receptors.

This invention provides the above-described isolated nucleic acid, wherein the nucleic acid is DNA. In one embodiment, the DNA is cDNA. In another embodiment, the DNA is genomic DNA. In still another embodiment, the nucleic acid molecule is RNA. Methods for production and manipulation of nucleic acid molecules are well known in the art.

This invention provides a vector encoding the nucleic acid of human GALR3 receptor.

In another embodiment, the nucleic acid encodes a vertebrate GALR3 receptor. In a separate embodiment, the nucleic acid encodes a mammalian GALR3 receptor. In another embodiment, the nucleic acid encodes a rat GALR3 receptor. In still another embodiment, the nucleic acid encodes a human GALR3 receptor.

This invention further provides nucleic acid which is degenerate with respect to the DNA comprising the coding sequence of the plasmid K1086 (ATCC Accession No. 97747). This invention further provides nucleic acid which is degenerate with respect to any DNA encoding a GALR3 receptor. In an embodiment, the nucleic acid comprises a nucleotide sequence which is degenerate with respect to the nucleotide sequence of plasmid K1086, that is, a nucleotide sequence which is translated into the same amino acid sequence. In an embodiment, the nucleic acid comprises a nucleotide sequence which is degenerate with respect to the nucleotide sequence of plasmid pEXJ-rGalR3T (ATCC Accession No. 97826). In another embodiment, the nucleic acid comprises a nucleotide sequence which is degenerate with respect to the nucleotide sequence of plasmid pEXJ-hGalR3 (ATCC Accession No. 97827).

This invention also encompasses DNAs and cDNAs which encode amino acid sequences which differ from those of the GALR3 galanin receptor, but which should not produce phenotypic changes. Alternatively, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

G-protein coupled receptors such as the GALR3 receptors of the present invention are characterized by the ability of an agonist to promote the formation of a high-affinity ternary complex between the agonist, the receptor, and an intracellular G-protein. This complex is formed in the presence of physiological concentrations of GTP, and results in the dissociation of the alpha subunit of the G protein from the beta and gamma subunits of the G protein, which further results in a functional response, i.e., activation of downstream effectors such as adenylyl cyclase or phospholipase C. This high-affinity complex is transient even in the presence of GTP, so that if the complex is destablized, the affinity of the receptor for agonists is reduced. Thus, if a receptor is not optimally coupled to G protein under the conditions of an assay, an agonist will bind to the receptor with low affinity. In contrast, the affinity of the receptor for an antagonist is normally not significantly affected by the presence or absence of G protein. Functional assays may be used to determine whether a compound binds to the receptor, but may be more time-consuming or difficult to perform than a binding assay. Therefore, it may desirable to produce a receptor which will bind to agonists with high affinity in a binding assay. Examples of modified receptors which bind agonists with high affinity are disclosed in WO 96/14331, which describes neuropeptide Y receptors modified in the third intracellular domain. The modifications may include deletions of 6–13 amino acids in the third intracellular loop. Such deletions preferably end immediately before the polar or charged residue at the beginning of helix six. In an embodiment, the deleted amino acids are at the carboxy terminus of the third intracellular domain. Such modified receptors may be produced using methods well-known in the art such as site-directed mutagenesis or recombinant techniques using restriction enzymes.

This invention provides an isolated nucleic acid encoding a modified GALR3 receptor, which differs from a GALR3 receptor by having an amino acid(s) deletion, replacement or addition in the third intracellular domain. In one embodiment, the modified GALR3 receptor differs by having a deletion in the third intracellular domain. In another embodiment, the modified GALR3 receptor differs by having an amino acid replacement or addition to the third intracellular domain.

The modified receptors of this invention may be transfected into cells either transiently or stably using methods well-known in the art, examples of which are disclosed herein. This invention also provides for binding assays using the modified receptors, in which the receptor is expressed either transiently or in stable cell lines. This invention further provides for a compound identified using a modified receptor in a binding assay such as the binding assays described herein.

The nucleic acids described and claimed herein are useful for the information which they provide concerning the amino acid sequence of the polypeptide and as products for the large scale synthesis of the polypeptide by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated galanin GALR3 receptor protein. In one embodiment, the GALR3 receptor protein has the same or substantially the same amino acid sequence as the amino acid sequence encoded by plasmid K1086. In another embodiment, the GALR3 receptor protein has the amino acid sequence encoded by plasmid K1086. In another embodiment, the protein has the amino acid sequence encoded by the plasmid pEXJ-hGalR3. In an embodiment, the GALR3 receptor protein has the same or substantially the same amino acid sequence as the amino acid sequence shown in FIG. 2 (Seq. I.D. No: 2). In an embodiment, the GALR3 receptor comprises the same or substantially the same amino acid sequence as the amino acid sequence shown in FIG. 4 (Seq. I.D. No: 4) from amino acid 60 through amino acid 427.

This invention provides a vector comprising the above-described nucleic acid molecule.

Vectors which comprise the isolated nucleic acid molecule described hereinabove also are provided. Suitable vectors comprise, but are not limited to, a plasmid or a virus. These vectors may be transformed into a suitable host cell to form a host cell expression system for the production of a polypeptide having the biological activity of a galanin GALR3 receptor. Suitable host cells include, for example, neuronal cells such as the glial cell line C6, a Xenopus cell such as an oocyte or melanophore cell, as well as numerous mammalian cells and non-neuronal cells.

This invention provides the above-described vector adapted for expression in a bacterial cell which further comprises the regulatory elements necessary for expression of the nucleic acid in the bacterial cell operatively linked to the nucleic acid encoding the GALR3 receptor as to permit expression thereof.

This invention provides the above-described vector adapted for expression in a yeast cell which comprises the regulatory elements necessary for expression of the nucleic acid in the yeast cell operatively linked to the nucleic acid encoding the GALR3 receptor as to permit expression thereof.

This invention provides the above-described vector adapted for expression in an insect cell which comprises the regulatory elements necessary for expression of the nucleic acid in the insect cell operatively linked to the nucleic acid encoding the GALR3 receptor as to permit expression thereof. In a still further embodiment, the vector is a baculovirus.

This invention provides the above-described vector adapted for expression in a amphibian cell which further comprises the regulatory elements necessary for expression of the nucleic acid in the amphibian cell operatively linked to the nucleic acid encoding the GALR3 receptor as to permit expression thereof.

In an embodiment, the vector is adapted for expression in a mammalian cell which comprises the regulatory elements necessary for expression of the nucleic acid in the mammalian cell operatively linked to the nucleic acid encoding the mammalian GALR3 receptor as to permit expression thereof.

In a further embodiment, the vector is adapted for expression in a mammalian cell which comprises the regulatory elements necessary for expression of the nucleic acid in the mammalian cell operatively linked to the nucleic acid encoding the rat GALR3 receptor as to permit expression thereof.

In a still further embodiment, the vector is a plasmid.

In another embodiment, the plasmid is adapted for expression in a mammalian cell which comprises the regulatory elements necessary for expression of the nucleic acid in the mammalian cell operatively linked to the nucleic acid encoding the human GALR3 receptor as to permit expression thereof.

This invention provides the above-described plasmid adapted for expression in a mammalian cell which comprises the regulatory elements necessary for expression of nucleic acid in a mammalian cell operatively linked to the nucleic acid encoding the mammalian GALR3 receptor as to permit expression thereof.

This invention provides a plasmid designated K1086 (ATCC Accession No. 97747) which comprises the regulatory elements necessary for expression of DNA in a mammalian cell operatively linked to DNA encoding the GALR3 galanin receptor so as to permit expression thereof.

This plasmid (K1086) was deposited on Oct. 8, 1996, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 97747.

This invention provides a plasmid designated pEXJ-hGalR3 (ATCC Accession No. 97827) which comprises the regulatory elements necessary for expression of DNA in a mammalian cell operatively linked to DNA encoding the human GALR3 galanin receptor so as to permit expression thereof.

This plasmid was deposited December 17, 1996, with the ATCC, 12301 Parklawn Drive, Rockville, Md., 20852, U.S.A. under the provisions of the Budapest Treaty forth International Recognition of the Deposit of Microorganisms for the Purposes of Patent Procedure and was accorded ATCC Accession No. 97827.

This invention provides a plasmid designated pEXJ-rGalR3T (ATCC Accession No. 97826) which comprises the regulatory elements necessary for expression of DNA in a mammalian cell operatively linked to DNA encoding the rat GALR3 galanin receptor so as to permit expression thereof.

This plasmid was deposited Dec. 17, 1996, with the ATCC, 12301 Parklawn Drive, Rockville, Md., 20852, U.S.A. under the provisions of the Budapest Treaty for the International Recognition of the Deposit of Microorganisms for the Purposes of Patent Procedure and was accorded ATCC Accession No. 97826.

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the receptor depending upon the host cell used. In one embodiment, the vector or plasmid comprises the coding sequence of the GALR3 receptor and the regulatory elements necessary for expression in the host cell.

This invention provides a eukaryotic cell comprising the above-described plasmid or vector. This invention provides a mammalian cell comprising the above-described plasmid or vector. In an embodiment the cell is a Xenopus oocyte or melanophore cell. In an embodiment, the cell is a neuronal cell such as the glial cell line C6. In an embodiment, the mammalian cell is non-neuronal in origin. In an embodiment, the mammalian cell is a COS-7 cell. In another embodiment the mammalian cell is a Chinese hamster ovary (CHO) cell. In another embodiment, the cell is a mouse Y1 cell.

In still another embodiment, the mammalian cell is a 293 human embryonic kidney cell. In still another embodiment, the mammalian cell is a NIH-3T3 cell. In another embodiment, the mammalian cell is an LM(tk−) cell.

In an embodiment, the mammalian cell is the 293 cell designated 293-rGALR3-105, which comprises the "trimmed" plasmid pEXJ-rGalR3T. This cell line was deposited with the ATCC on Feb. 19, 1997, under the provisions of the Budapest Treaty for the International Recognition of the Deposit of Microorganisms for the Purposes of Patent Procedure, and was accorded ATCC Accession No. CRL-12287.

In an embodiment, the mammalian cell is the LM(tk−) cell designated L-hGALR3-228, which comprises the plasmid pEXJ-hGalR3. This cell line was deposited with the ATCC on Jun. 25, 1997, under the provisions of the Budapest Treaty for the International Recognition of the Deposit of Microorganisms for the Purposes of Patent Procedure, and was accorded ATCC Accession No. CRL-12373.

This invention also provides an insect cell comprising the above-described vector. In an embodiment, the insect cell is an Sf9 cell. In another embodiment, the insect cell is an Sf21 cell.

This invention provides a membrane preparation isolated from any of the above-described cells.

This invention provides a nucleic acid probe comprising at least 15 nucleotides, which probe specifically hybridizes with a nucleic acid encoding a GALR3 receptor, wherein the probe has a unique sequence corresponding to a sequence present within one of the two strands of the nucleic acid encoding the GALR3 receptor contained in plasmid K1086.

This invention further provides a nucleic acid probe comprising at least 15 nucleotides, which probe specifically hybridizes with a nucleic acid encoding a GALR3 receptor, wherein the probe has a unique sequence corresponding to a sequence present within one of the two strands of the nucleic acid encoding the GALR3 receptor contained in plasmid pEXJ-rGalR3T.

This invention still further provides a nucleic acid probe comprising at least 15 nucleotides, which probe specifically hybridizes with a nucleic acid encoding a GALR3 receptor, wherein the probe has a unique sequence corresponding to a sequence present within (a) the nucleic acid sequence shown in FIG. 1 (Seq. ID NO. 1) or (b) the reverse complement to the nucleic acid sequence shown in FIG. 1 (Seq. ID No: 1).

This invention also provides a nucleic acid probe comprising at least 15 nucleotides, which probe specifically hybridizes with a nucleic acid encoding a GALR3 receptor, wherein the probe has a unique sequence corresponding to a sequence present within one of the two strands of the nucleic acid encoding the GALR3 receptor contained in plasmid pEXJ-hGalR3. This invention provides a nucleic acid probe comprising at least 15 nucleotides, which probe specifically hybridizes with a nucleic acid encoding a GALR3 receptor, wherein the probe has a unique sequence corresponding to a sequence present within (a) the nucleic acid sequence shown in FIG. 3 (Seq. ID No: 3) or (b) the reverse complement to the nucleic acid sequence shown in FIG. 3 (Seq. ID NO. 3).

This invention provides a nucleic acid probe comprising a nucleic acid which specifically hybridizes with a nucleic acid encoding a GALR3 receptor, wherein the probe comprises a unique sequence of at least 15 nucleotides within a fragment of (a) the nucleic acid sequence contained in plasmid K1086 or (b) the antisense nucleic acid sequence capable of specifically hybridizing to the nucleic acid sequence contained in plasmid K1086. In one embodiment the GALR3 receptor is encoded by the coding sequence of the plasmid K1086, or the reverse complement (antisense sequence) of the coding sequence of plasmid K1086. In an embodiment, the nucleic acid encoding a GALR3 receptor comprises an intron.

This invention further provides a nucleic acid probe comprising a nucleic acid molecule of at least 15 nucleotides which is complementary to a unique fragment of the sequence of a nucleic acid molecule encoding a GALR3 receptor. This invention also provides a nucleic acid probe comprising a nucleic acid molecule of at least 15 nucleotides which is complementary to the antisense sequence of a unique fragment of the sequence of a nucleic acid molecule encoding a GALR3 receptor.

In an embodiment, the nucleic acid probe is DNA. In another embodiment the nucleic acid probe is RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid of at least 15 nucleotides capable of specifically hybridizing with a sequence of a nucleic acid encoding the GALR3 galanin receptors can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the GALR3 receptor into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the GALR3 galanin receptor downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention provides an antisense oligonucleotide having a sequence capable of specifically hybridizing to mRNA encoding a GALR3 galanin receptor, so as to prevent translation of the mRNA.

This invention provides an antisense oligonucleotide having a sequence capable of specifically hybridizing to the genomic DNA molecule encoding a GALR3 receptor.

This invention provides an antisense oligonucleotide comprising chemical analogues of nucleotides.

This invention provides an antibody directed to a GALR3 receptor. This invention also provides an antibody directed to a rat GALR3 receptor. This invention also provides an antibody directed to a human GALR3 receptor. In an embodiment, the rat GALR3 has an amino acid sequence substantially the same as an amino acid sequence encoded by plasmid K1086. In an embodiment, the human GALR3 receptor has a sequence, which sequence comprises substantially the same sequence as the sequence shown in FIG. 4 (Seq. I.D. No: 4) from amino acid 60 through amino acid 427. This invention further provides an antibody capable of competitively inhibiting the binding of a second antibody to a GALR3 receptor.

This invention provides a monoclonal antibody directed to an epitope of a GALR3 receptor, which epitope is present on the surface of a cell expressing a GALR3 receptor.

This invention provides a pharmaceutical composition comprising an amount of the oligonucleotide effective to reduce activity of a GALR3 receptor by passing through a cell membrane and binding specifically with mRNA encoding a GALR3 receptor in the cell so as to prevent its translation and a pharmaceutically acceptable carrier capable of passing through a cell membrane. In an embodiment, the oligonucleotide is coupled to a substance which inactivates mRNA. In another embodiment, the substance which inactivates mRNA is a ribozyme.

This invention provides the above-described pharmaceutical composition, wherein the pharmaceutically acceptable carrier capable of passing through a cell membrane comprises a structure which binds to a receptor specific for a selected cell type and is thereby taken up by cells of the selected cell type. In an embodiment, the pharmaceutically acceptable carrier is capable of binding to a receptor which is specific for a selected cell type.

This invention provides a pharmaceutical composition comprising an amount of an antagonist effective to reduce the activity of a GALR3 receptor and a pharmaceutically acceptable carrier.

This invention provides a pharmaceutical composition comprising an amount of an agonist effective to increase activity of a GALR3 receptor and a pharmaceutically acceptable carrier.

This invention provides the above-described pharmaceutical composition which comprises an amount of the antibody effective to block binding of a ligand to the GALR3 receptor and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention provides a transgenic nonhuman mammal expressing DNA encoding a GALR3 receptor.

This invention provides a transgenic nonhuman mammal comprising a homologous recombination knockout of the native GALR3 receptor.

This invention provides a transgenic nonhuman mammal whose genome comprises antisense DNA complementary to DNA encoding a GALR3 receptor so placed as to be transcribed into antisense mRNA which is complementary to mRNA encoding a GALR3 receptor and which hybridizes to mRNA encoding a GALR3 receptor thereby reducing its translation.

This invention provides the above-described transgenic nonhuman mammal, wherein the DNA encoding a GALR3 receptor additionally comprises an inducible promoter.

This invention provides the transgenic nonhuman mammal, wherein the DNA encoding a GALR3 receptor additionally comprises tissue specific regulatory elements.

In an embodiment, the transgenic nonhuman mammal is a mouse.

Animal model systems which elucidate the physiological and behavioral roles of GALR3 receptor are produced by creating transgenic animals in which the activity of the GALR3 receptor is either increased or decreased, or the amino acid sequence of the expressed GALR3 receptor is altered, by a variety of techniques. Examples of these techniques include, but are not limited to: 1) Insertion of normal or mutant versions of DNA encoding a GALR3 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these GALR3 receptor sequences. The technique of homologous recombination is well known in the art. It replaces the native gene with the inserted gene and so is useful for producing an animal that cannot express native GALR3 receptors but does express, for example, an inserted mutant GALR3 receptor, which has replaced the native GALR3 receptor in the animal's genome by recombination, resulting in underexpression of the transporter. Microinjection adds genes to the genome, but does not remove them, and so is useful for producing an animal which expresses its own and added GALR3 receptors, resulting in overexpression of the GALR3 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a GALR3 receptor is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and tie egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a process for identifying a chemical compound which specifically binds to a GALR3 receptor which comprises contacting cells containing DNA encoding and expressing on their cell surface the GALR3 receptor, wherein such cells do not normally express the GALR3 receptor, with the compound under conditions suitable for binding, and detecting specific binding of the chemical compound to the GALR3 receptor.

This invention further provides a process for identifying a chemical compound which specifically binds to a GALR3 receptor which comprises contacting a membrane fraction from a cell extract of cells containing DNA encoding and expressing on their cell surface the GALR3 receptor, wherein such cells do not normally express the GALR3 receptor, with the compound under conditions suitable for binding, and detecting specific binding of the chemical compound to the GALR3 receptor.

This invention also provides a process for determining whether a chemical compound can specifically bind to a GALR3 receptor which comprises contacting cells transfected with and expressing DNA encoding the GALR3 receptor with the compound under conditions permitting binding of compounds to such receptor, and detecting the presence of any such compound specifically bound to the GALR3 receptor, so as to thereby determine whether the ligand specifically binds to the GALR3 receptor.

This invention provides a process for determining whether a chemical compound can specifically bind to a GALR3 receptor which comprises preparing a cell extract from cells transfected with and expressing DNA encoding the GALR3 receptor, isolating a membrane fraction from the cell extract, contacting the membrane fraction with the compound under conditions permitting binding of compounds to such receptor, and detecting the presence of the compound specifically bound to the GALR3 receptor, so as to thereby determine whether the compound specifically binds to the GALR3 receptor.

In one embodiment, the GALR3 receptor is a mammalian GALR3 receptor. In another embodiment, the GALR3 receptor is a rat GALR3 receptor. In still another embodiment, the GALR3 receptor has the same or substantially the same amino acid sequence as that encoded by plasmid K1086. In still another embodiment, the GALR3 receptor has the amino acid sequence encoded by plasmid K1086. In another embodiment, the GALR3 receptor has substantially the same amino acid sequence as the amino acid sequence shown in FIG. 2 (Seq. ID NO. 2). In another embodiment, the GALR3 receptor has the amino acid sequence shown in FIG. 2 (Seq. ID NO. 2). In still another embodiment, the cells are transfected with the plasmid pEXJ-RGALR3T (ATCC Accession No. 97826), encoding the rat GALR3 receptor. Plasmid pEXJ-RGalR3T comprises the entire coding region of rat GALR3, but in which the 5' initiating ATG is joined directly to the vector, and which comprises only 100 nucleotides from the 3' untranslated region after the stop codon (i.e., up to and including nucleotide 1275 in FIG. 1 (Seq. ID NO. 1)). Transfection of cells with the "trimmed" plasmid results in a higher level of expression of the rat CALR3 receptor than the level of expression when plasmid K1086 is used. The use of the "trimmed" plasmid provides for greater convenience and accuracy in binding assays. In another embodiment the GALR3 receptor is a human GALR3 receptor. In still another embodiment, the GALR3 receptor has the same or substantially the same amino acid sequence as that encoded by plasmid pEXJ-hGalR3 (ATCC Accession No. 97827). In an embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO. 4) from amino acid 60 through amino acid 427.

In an embodiment, the above process further comprises determining whether the compound selectively binds to the GALR3 receptor relative to another galanin receptor. In another embodiment, the determination whether the compound selectively binds to the GALR3 receptor comprises: (a) determining the binding affinity of the compound for the GALR3 receptor and for such other galanin receptor; and (b) comparing the binding affinities so determined, the presence of a higher binding affinity for the GALR3 receptor than for such other galanin receptor indicating that the compound selectively binds to the GALR3 receptor. In one embodiment, the other galanin receptor is a GALR1 receptor. In another embodiment, the other galanin receptor is a GALR2 receptor.

This invention provides a process for determining whether a chemical compound is a GALR3 receptor agonist which comprises contacting cells transfected with and expressing DNA encoding the GALR3 receptor with the compound under conditions permitting the activation of the GALR3 receptor, and detecting an increase in GALR3 receptor activity, so as to thereby determine whether the compound is a GALR3 receptor agonist.

This invention provides a process for determining whether a chemical compound is a GALR3 receptor agonist which comprises preparing a cell extract from cells transfected with and expressing DNA encoding the GALR3 receptor, isolating a membrane fraction from the cell extract, contacting the membrane fraction with the compound under conditions permitting the activation of the GALR3 receptor, and detecting an increase in GALR3 receptor activity, so as to thereby determine whether the compound is a GALR3 receptor agonist.

In one embodiment, the GALR3 receptor is a rat GALR3 receptor. In another embodiment, the GALR3 receptor has the same or substantially the same amino acid sequence as that encoded by the plasmid K1086. In yet another embodiment, the GALR3 receptor has the amino acid sequence encoded by the plasmid K1086. In another embodiment, the GALR3 receptor has substantially the same amino acid sequence as the amino acid sequence shown in FIG. 2 (Seq. ID No. 2). In another embodiment, the GALR3 receptor has the amino acid sequence shown in FIG. 2 (Seq. ID No. 2). In another embodiment, the GALR3 receptor is a human GALR3 receptor. In still another embodiment, the GALR3 receptor has the same or substantially the same amino acid sequence as that encoded by plasmid pEXJ-hGalR3 (ATCC Accession No. 97827). In another embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO: 4) from amino acid 60 through amino acid 427. In another embodiment of this invention the cells are transfected with plasmid pEXJ-RGalR3T (ATCC Accession No. 97826).

This invention provides a process for determining whether a chemical compound is a GALR3 receptor antagonist which comprises contacting cells transfected with and expressing DNA encoding the GALR3 receptor with the compound in the presence of a known GALR3 receptor agonist, such as galanin, under conditions permitting the activation of the GALR3 receptor, and detecting a decrease in GALR3 receptor activity, so as to thereby determine whether the compound is a GALR3 receptor antagonist.

This invention provides a process for determining whether a chemical compound is a GALR3 receptor antagonist which comprises preparing a cell extract from cells transfected with and expressing DNA encoding the GALR3 receptor, isolating a membrane fraction from the cell extract, contacting the membrane fraction with the ligand in the presence of a known GALR3 receptor agonist, such as galanin, under conditions permitting the activation of the GALR3 receptor, and detecting a decrease in GALR3 receptor activity, so as to thereby determine whether the compound is a GALR3 receptor antagonist.

In an embodiment, the GALR3 receptor is a mammalian GALR3 receptor. In one embodiment of the invention, the GALR3 receptor is a rat GALR3 receptor. In another embodiment, the GALR3 receptor has the same or substantially the same amino acid sequence as that encoded by the plasmid K1086. In still another embodiment, the GALR3 receptor has the amino acid sequence encoded by the plasmid K1086. In another embodiment, the GALR3 receptor has substantially the same amino acid sequence as the amino acid sequence shown in FIG. 2 (Seq. ID No: 2). In another embodiment, the GALR3 receptor has the amino acid sequence shown in FIG. 2 (Seq. ID No: 2). In another embodiment, the GALR3 receptor is a human GALR3 receptor. In still another embodiment, the GALR3 receptor has the same or substantially the same amino acid sequence as that encoded by plasmid pEXJ-hGalR3 (ATCC Accession No. 97827). In another embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO. 4) from amino acid 60 through amino acid 427.

In an embodiment of the above-described methods, the cell is a non-mammalian cell such as an insect cell or a Xenopus cell. In another embodiment, the cell is a mammalian cell. In a further embodiment, the cell is non-neuronal in origin. In still further embodiments, the non-neuronal cell is a COS-7 cell, 293 human embryonic kidney cell, NIH-3T3 cell, a CHO cell, or LM(tk−) cell. In another embodiment, the cell is a mouse Y1 cell.

This invention provides a compound determined by the above-described methods. In one embodiment of the above-described methods, the compound is not previously known to bind to a GALR3 receptor.

This invention provides a GALR3 agonist determined by the above-described methods. This invention also provides a GALR3 antagonist determined by the above-described methods.

In an embodiment of any of the above processes, the cells are transfected with and expressing GIRK1 and GIPK4.

In an embodiment of any of the above processes, the GALR3 receptor is a mammalian GALR3 receptor.

This invention provides a pharmaceutical composition which comprises an amount of a GALR3 receptor agonist determined by the above-described processes effective to increase activity of a GALR3 receptor and a pharmaceutically acceptable carrier. In an embodiment, the GALR3 receptor agonist is not previously known.

This invention provides a pharmaceutical composition which comprises an amount of a GALR3 receptor antagonist determined by the above-described processes effective to reduce activity of a GALR3 receptor and a pharmaceutically acceptable carrier. In an embodiment, the GALR3 receptor antagonist is not previously known.

This invention provides a pharmaceutical composition which comprises an amount of a GALR3 receptor agonist effective to increase activity of a GALR3 receptor and a pharmaceutically acceptable carrier.

This invention provides a pharmaceutical composition which comprises an amount of a GALR3 receptor antagonist effective to reduce activity of a GALR3 receptor and a pharmaceutically acceptable carrier.

In further embodiments of the above-described processes, the agonist or antagonist is not previously known to bind to a GALR3 receptor.

This invention provides a process involving competitive binding for identifying a chemical compound which specifically binds to a GALR3 receptor which comprises separately contacting cells expressing on their cell surface the GALR3 receptor, wherein such cells do not normally express the GALR3 receptor, with both the chemical compound and a second chemical compound known to bind to the receptor, and with only the second chemical compound, under conditions suitable for binding of both compounds, and detecting specific binding of the chemical compound to the GALR3 receptor, a decrease in the binding of the second chemical compound to the GALR3 receptor in the presence of the chemical compound indicating that the chemical compound binds to the GALR3 receptor.

This invention further provides a process involving competitive binding for identifying a chemical compound which specifically binds to a human GALR3 receptor which comprises separately contacting a membrane fraction from a cell extract of cells expressing on their cell surface the GALR3 receptor, wherein such cells do not normally express the GALR3 receptor, with both the chemical compound and a second chemical compound known to bind to the receptor, and with only the second chemical compound, under conditions suitable for binding of both compounds, and detecting specific binding of the chemical compound to the GALR3 receptor, a decrease in the binding of the second chemical compound to the GALR3 receptor in the presence of the chemical compound indicating that the chemical compound binds to the GALR3 receptor.

This invention further provides a process for determining whether a chemical compound specifically binds to and activates a GALR3 receptor, which comprises contacting cells producing a second messenger response and expressing on their cell surface the GALR3 receptor, wherein such cells do not normally express the GALR3 receptor, with the chemical compound under conditions suitable for activation of the GALR3 receptor, and measuring the second messenger response in the presence and in the absence of the chemical compound, a change in the second messenger response in the presence of the chemical compound indicating that the compound activates the GALR3 receptor.

This invention further provides a process for determining whether a chemical compound specifically binds to and activates a GALR3 receptor, which comprises contacting a membrane fraction from a cell extract of cells producing a second messenger response and expressing on their cell surface the GALR3 receptor, wherein such cells do not normally express the GALR3 receptor, with the chemical compound under conditions suitable for activation of the GALR3 receptor, and measuring the second messenger response in the presence and in the absence of the chemical compound, a change in the second messenger response in the presence of the chemical compound indicating that the compound activates the GALR3 receptor.

In an embodiment of the above processes, the second messenger response comprises potassium channel activation and the change in second messenger is an increase in the level of inward potassium current.

In one embodiment of the above processes, the second messenger response comprises adenylate cyclase activity and the change in second messenger response is a decrease in adenylate cyclase activity. In an embodiment, adenylate cyclase activity is determined by measurement of cyclic AMP levels.

In another embodiment of the above processes, the second messenger response comprises arachidonic acid release and the change in second messenger response is an increase in arachidonic acid levels.

In another embodiment of the above processes, the second messenger response comprises intracellular calcium levels and the change in second messenger response is an increase in intracellular calcium levels.

In a still further embodiment of the above processes, the second messenger response comprises inositol phospholipid hydrolysis and the change in second messenger response is an increase in inositol phospholipid hydrolysis.

This invention further provides a process for determining whether a chemical compound specifically binds to and inhibits activation of a GALR3 receptor, which comprises separately contacting cells producing a second messenger response and expressing on their cell surface the GALR3 receptor, wherein such cells do not normally express the GALR3 receptor, with both the chemical compound and a second chemical compound known to activate the GALR3 receptor, and with only the second compound, under conditions suitable for activation of the GALR3 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR3 receptor.

This invention further provides a process for determining whether a chemical compound specifically binds to and inhibits activation of a GALR3 receptor, which comprises separately contacting a membrane fraction from a cell extract of cells producing a second messenger response and expressing on their cell surface the GALR3 receptor, wherein such cells do not normally express the GALR3 receptor, with both the chemical compound and a second chemical compound known to activate the GALR3 receptor, and with only the second chemical compound, under conditions suitable for activation of the GALR3 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR3 receptor.

In an embodiment of the above processes, the second messenger response comprises potassium channel activation and the change in second messenger response is a smaller increase in the level of inward potassium current in the presence of both the chemical compound and the second chemical compound than in the presence of only the second chemical compound.

In one embodiment of the above processes, the second messenger response comprises adenylate cyclase activity and the change in second messenger response is a smaller decrease in the level of adenylate cyclase activity in the presence of both the chemical compound and the second chemical compound than in the presence of only the second chemical compound. In an embodiment, adenylate cyclase activity is determined by measurement of cyclic AMP levels.

In another embodiment of the above processes the second messenger response comprises arachidonic acid release, and the change in second messenger response is a smaller increase in arachidonic acid levels in the presence of both the chemical compound and the second chemical compound than in the presence of only the second chemical compound.

In another embodiment of the above processes the second messenger response comprises intracellular calcium levels, and the change in second messenger response is a smaller increase in intracellular calcium levels in the presence of both the chemical compound and the second chemical compound than in the presence of only the second chemical compound.

In yet another embodiment of the above processes, the second messenger response comprises inositol phospholipid hydrolysis, and the change in second messenger response is a smaller increase in inositol phospholipid hydrolysis in the presence of both the chemical compound and the second chemical compound than in the presence of only the second chemical compound.

In an embodiment of any of the above processes, the GALR3 receptor is a mammalian GALR3 receptor. In another embodiment of the above processes, the GALR3 receptor is a rat GALR3 receptor or a human GALR3 receptor. In still another embodiment of the above processes, the GALR3 receptor has the same or substantially the same amino acid sequence as encoded by the plasmid K1086 (ATCC Accession No. 97747). In another embodiment, the GALR3 receptor has substantially the same amino acid sequence as the amino acid sequence shown in FIG. 2 (Seq. ID No: 2). In another embodiment, the GALR3 receptor has the amino acid sequence shown in FIG. 2 (Seq. ID No: 2). In still another embodiment, the GALR3 receptor has the same or substantially the same amino acid sequence as that encoded by plasmid pEXJ-hGalR3 (ATCC Accession No. 97827). In another embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO. 4) from amino acid 60 through amino acid 427. In another embodiment of this invention the cells are transfected with plasmid pEXJ-RGalR3T (ATCC Accession No. 97826).

In one embodiment of the above-described processes, the cell is a non-mammalian cell such as an insect cell or a Xenopus cell. In another embodiment of any of the above processes, the cell is a mammalian cell. In still further embodiments, the cell is nonneuronal in origin. In another embodiment of the above processes, the nonneuronal cell is a COS-7 cell, 293 human embryonic kidney cell, CHO cell, mouse Y1 cell, NIH-3T3 cell or LM(tk−) cell.

This invention further provides a compound determined by any of the above processes. In another embodiment, the compound is not previously known to bind to a GALR3 receptor.

This invention provides a pharmaceutical composition which comprises an amount of a GALR3 receptor agonist determined by any of the above processes effective to increase activity of a GALR3 receptor and a pharmaceutically acceptable carrier. In an embodiment, the GALR3 receptor agonist is not previously known.

This invention provides a pharmaceutical composition which comprises an amount of a GALR3 receptor antagonist determined by any of the above processes effective to reduce activity of a GALR3 receptor and a pharmaceutically acceptable carrier. In an embodiment, the GALR3 receptor antagonist is not previously known.

This invention provides a method of screening a plurality of chemical compounds not known to bind to a GALR3 receptor to identify a compound which specifically binds to the GALR3 receptor, which comprises (a) contacting cells transfected with and expressing DNA encoding the GALR3 receptor with a compound known to bind specifically to the GALR3 receptor; (b) contacting the preparation of step (a) with the plurality of compounds not known to bind specifically to the GALR3 receptor, under conditions permitting binding of compounds known to bind the GALR3 receptor; (c) determining whether the binding of the compound known to bind to the GALR3 receptor is reduced in the presence of the compounds, relative to the binding of the compound in the absence of the plurality of compounds; and if so (d) separately determining the binding to the GALR3 receptor of each compound included in the plurality of compounds, so as to thereby identify the compound which specifically binds to the GALR3 receptor.

This invention provides a method of screening a plurality of chemical compounds not known to bind to a GALR3 receptor to identify a compound which specifically binds to the GALR3 receptor, which comprises (a) preparing a cell extract from cells transfected with and expressing DNA encoding the GALR3 receptor, isolating a membrane fraction from the cell extract, contacting the membrane fraction with a compound known to bind specifically to the GALR3 receptor; (b) contacting the preparation of step (a) with the plurality of compounds not known to bind specifically to the GALR3 receptor, under conditions permitting binding of compounds known to bind the GALR3 receptor; (c) determining whether the binding of the compound known to bind to the GALR3 receptor is reduced in the presence of the compounds, relative to the binding of the compound in the absence of the plurality of compounds; and if so (d) separately determining the binding to the GALR3 receptor of each compound included in the plurality of compounds, so as to thereby identify the compound which specifically binds to the GALR3 receptor.

In an embodiment of any of the above processes, the GALR3 receptor is a mammalian GALR3 receptor. In an embodiment of the above-described methods, the GALR3 receptor is a rat GALR3 receptor. In another embodiment, the GALR3 receptor has the same or substantially the same amino acid sequence as the amino acid sequence encoded by plasmid K1086. In another embodiment, the GALR3 receptor has substantially the same amino acid sequence as the amino acid sequence shown in FIG. 2 (Seq. ID NO. 2). In another embodiment, the GALR3 receptor has the amino acid sequence shown in FIG. 2 (Seq. ID No: 2). In another embodiment, the GALR3 receptor is a human GALR3 receptor. In still another embodiment, the GALR3 receptor has the same or substantially the same amino acid sequence as that encoded by plasmid pEXJ-hGalR3 (ATCC Accession No. 97827). In another embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO. 4) from amino acid 60 through amino acid 427.

This invention provides a method of screening a plurality of chemical compounds not known to activate a GALR3 receptor to identify a compound which activates the GALR3 receptor which comprises (a) contacting cells transfected with and expressing the GALR3 receptor with the plurality of compounds not known to activate the GALR3 receptor, under conditions permitting activation of the GALR3 receptor; (b) determining whether the activity of the GALR3 receptor is increased in the presence of the compounds; and if so (c) separately determining whether the activation of the GALR3 receptor is increased by each compound included in the plurality of compounds, so as to thereby identify the compound which activates the GALR3 receptor.

This invention provides a method of screening a plurality of chemical compounds not known to activate a GALR3 receptor to identify a compound which activates the GALR3 receptor which comprises (a) preparing a cell extract from cells transfected with and expressing DNA encoding the GALR3 receptor, isolating a membrane fraction from the cell extract, contacting the membrane fraction with the plurality of compounds not known to activate the GALR3 receptor, under conditions permitting activation of the GALR3 receptor; (b) determining whether the activity of the GALR3 receptor is increased in the presence of the compounds; and if so (c) separately determining whether the activation of the GALR3 receptor is increased by each compound included in the plurality of compounds, so as to thereby identify the compound which activates the GALR3 receptor.

In an embodiment of the above processes, the cells are transfected with and expressing GIRK1 and GIRK4. In another embodiment, the GALR3 receptor is a mammalian GALR3 receptor.

In an embodiment of any of the above-described methods, the GALR3 receptor is a rat GALR3 receptor. In still another embodiment, the GALR3 receptor has the same or substantially the same amino acid sequence as the amino acid sequence encoded by plasmid K1086. In another embodiment, the GALR3 receptor has substantially the same amino acid sequence as the amino acid sequence shown in FIG. 2 (Seq. ID No: 2). In another embodiment, the GALR3 receptor has the amino acid sequence shown in FIG. 2 (Seq. ID No: 2). In another embodiment, the CALR3 receptor is a human GALR3 receptor. In still another embodiment, the GALR3 receptor has the same or substantially the same amino acid sequence as that encoded by plasmid pEXJ-hGalR3 (ATCC Accession No. 97827). In another embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO. 4) from amino acid 60 through amino acid 427.

This invention provides a method of screening a plurality of chemical compounds not known to inhibit the activation of a GALR3 receptor to identify a compound which inhibits the activation of the GALR3 receptor, which comprises (a) contacting cells transfected with and expressing the GALR3 receptor with the plurality of compounds in the presence of a known GALR3 receptor agonist, under conditions permitting activation of the GALR3 receptor; (b) determining whether the activation of the GALR3 receptor is reduced in the presence of the plurality of compounds, relative to the activation of the GALR3 receptor in the absence of the plurality of compounds; and if so (c) separately determining the inhibition of activation of the GALR3 receptor for each compound included in the plurality of compounds, so as to thereby identify the compound which inhibits the activation of the GALR3 receptor.

This invention provides a method of screening a plurality of chemical compounds not known to inhibit the activation of a GALR3 receptor to identify a compound which inhibits the activation of the GALR3 receptor, which comprises (a) preparing a cell extract from cells transfected with and expressing DNA encoding the GALR3 receptor, isolating a membrane fraction from the cell extract, contacting the membrane fraction with the plurality of compounds in the presence of a known GALR3 receptor agonist, under conditions permitting activation of the GALR3 receptor; (b) determining whether the activation of the GALR3 receptor is reduced in the presence of the plurality of compounds, relative to the activation of the GALR3 receptor in the absence of the plurality of compounds; and if so (c) separately determining the inhibition of activation of the GALR3 receptor for each compound included in the plurality of compounds, so as to thereby identify the compound which inhibits the activation of the GALR3 receptor.

In an embodiment of the above processes, the cells are transfected with and expressing GIRK1 and GIRK4. In another embodiment, the GALR3 receptor is a mammalian GALR3 receptor.

In an embodiment of any of the above-described methods, the GALR3 receptor is a rat GALR3 receptor. In another embodiment, the GALR3 receptor has the same or substantially the same amino acid sequence as the amino acid sequence encoded by plasmid K1086. In another embodiment, the GALR3 receptor has substantially the same amino acid sequence as the amino acid sequence shown in FIG. 2 (Seq. ID No: 2). In another embodiment, the GALR3 receptor has the amino acid sequence shown in FIG. 2 (Seq. ID No: 2). In another embodiment, the GALR3 receptor is a human GALR3 receptor. In still another embodiment, the GALR3 receptor has the same or substantially the same amino acid sequence as that encoded by plasmid pEXJ-hGalR3 (ATCC Accession No. 97827). In another embodiment, the human GALR3 receptor has a sequence, which sequence comprises substantially the same amino acid sequence as the sequence shown in FIG. 4 (Seq. I.D. No: 4) from amino acid 60 through amino acid 427. In another embodiment, the GALR3 receptor has a sequence, which sequence comprises the sequence shown in FIG. 4 (Seq. ID NO: 4) from amino acid 60 through amino acid 427.

In an embodiment of the above processes, the cells are transfected with and expressing GIRK1 and GIRK4. In an embodiment of the above processes, receptor activation is determined by measurement of potassium channel activation. In an embodiment, receptor activation is determined by measurement of an increase in inward potassium current. In another embodiment, inhibition of receptor activation is determined by a smaller increase in inward potassium current in the presence of the compound and a galanin receptor agonist than in the presence of only the galanin receptor agonist. In an embodiment, the galanin receptor agonist is galanin.

This invention provides a pharmaceutical composition comprising a compound identified by any of the above-described methods effective to increase GALR3 receptor activity and a pharmaceutically acceptable carrier.

This invention provides a pharmaceutical composition comprising a compound identified by any of the above-described methods effective to decrease GALR3 receptor activity and a pharmaceutically acceptable carrier.

This invention provides any of the above processes, which further comprises a process for determining whether the compound selectively activates the GALR3 receptor relative to another galanin receptor.

This invention provides a process for determining whether a compound selectively activates the GALR3 receptor relative to another galanin receptor which comprises: (a) determining the potency of the compound for the GALR3 receptor and for such other galanin receptor; and (b) comparing the potencies so determined, the presence of a higher potency for the GALR3 receptor than for such other galanin receptor indicating that the compound selectively activates the GALR3 receptor. In an embodiment of the above process such other galanin receptor is a GALR1 receptor. In another embodiment, such other galanin receptor is a GALR2 receptor.

This invention further provides any of the above processes, which further comprises a process for determining whether the compound selectively inhibits the activation of the GALR3 receptor relative to another galanin receptor.

This invention provides a process for determining whether a compound selectively inhibits the activation of the GALR3 receptor relative to another galanin receptor, which comprises: (a) determining the decrease in the potency of a known galanin receptor agonist for the GALR3 receptor in the presence of the compound, relative to the potency of the agonist in the absence of the compound; (b) determining the decrease in the potency of the agonist for such other galanin receptor in the presence of the compound, relative to the potency of the agonist in the absence of the compound; and (c) comparing the decrease in potencies so determined, the presence of a greater decrease in potency for the GALR3 receptor than for such other galanin receptor indicating that the compound selectively inhibits the activation of the GALR3 receptor. In an embodiment of the above processes, such other galanin receptor is a GALR1 receptor. In another embodiment, such other galanin receptor is a GALR2 receptor.

In an embodiment of any of the above-described methods, the activation of the GALR3 receptor is determined by a second messenger assay. In an embodiment, the second messenger assay measures adenylate cyclase activity. In other embodiments, the second messenger is cyclic AMP, intracellular calcium, or arachidonic acid or a phosphoinositol lipid metabolite. Receptor activation may also be measured by assaying the binding of GTPγS (gamma thiol GTP) to membranes, which precedes and is therefore independent of second messenger coupling.

This invention provides a process for determining whether a chemical compound is a GALR3 receptor agonist, which comprises preparing a cell extract from cells transfected with and expressing DNA encoding the GALR3 receptor, isolating a membrane fraction from the cell extract, separately contacting the membrane fraction with both the chemical compound and GTPγS, and with only GTPγS, under conditions permitting the activation of the GALR3 receptor, and detecting GTPγS binding to the membrane fraction, an increase in GTPγS binding in the presence of the compound indicating that the chemical compound activates the GALR3 receptor.

This invention provides a process for determining whether a chemical compound is a GALR3 receptor antagonist, which comprises preparing a cell extract from cells transfected with and expressing DNA encoding the GALR3 receptor, isolating a membrane fraction from the cell extract, separately contacting the membrane fraction with the chemical compound, GTPγS and a second chemical compound known to activate the GALR3 receptor, with GTPγS and only the second compound, and with GTPγS alone, under conditions permitting the activation of the GALR3 receptor, detecting GTPγS binding to each membrane fraction, and comparing the increase in GTPγS binding in the presence of the compound and the second compound relative to the binding of GTPγS alone, to the increase in GTPγS binding in the presence of the second chemical compound relative to the binding of GTPγS alone, a smaller increase in GTPγS binding in the presence of the compound and the second compound indicating that the compound is a GALR3 receptor antagonist. In an embodiment of any of the above-described processes, the second chemical compound is a labeled compound. In another embodiment, the second chemical compound is a radiolabeled compound.

In an embodiment of any of the above-described processes, the GALR3 receptor is a mammalian GALR3 receptor. In another embodiment of any of the above-described processes, the GALR3 receptor has substantially the same amino acid sequence as encoded by the plasmid K1086 (ATCC Accession No. 97747). In another embodiment of any of the above-described processes, the GALR3 receptor has substantially the same amino acid sequence as that shown in FIG. 2 (Seq. ID No: 2). In still another embodiment of any of the above-described processes, the GALR3 receptor has substantially the same amino acid sequence as encoded by the plasmid pEXJ-hGalR3 (ATCC Accession No. 97827). In an embodiment of any of the above-described processes, the GALR3 receptor has a sequence, which sequence comprises substantially the same amino acid sequence as that shown in FIG. 4 (Seq. ID No: 4) from amino acid 60 through amino acid 427. In still another embodiment of any of the above-described processes, the GALR3 receptor has a sequence, which sequence comprises a sequence shown in FIG. 4 (Seq. ID No: 4) from amino acid 60 through amino acid 427.

In an embodiment of any of the above-described processes, the cell is an insect cell.

In an embodiment of any of the above-described processes, the cell is a mammalian cell. In another embodiment of any of the above-described processes, the mammalian cell is nonneuronal in origin. In another embodiment of any of the above-described processes, the nonneuronal cell is a COS-7 cell, CHO cell, 293 human embryonic kidney cell, NIH-3T3 cell or LM(tk−) cell. In another embodiment, the nonneuronal cell is the 293 human embryonic kidney cell designated 293-rGALR3-105 (ATCC Accession No. CRL-12287). In still another embodiment, the nonneuronal cell is the LM(tk−) cell designated L-hGALR3-228 (ATCC Accession No. CRL-12373).

GTPγS assays are well-known in the art, and it is expected that variations on the method described above, such as are described by e.g., Tian et al. (1994) or Lazareno and Birdsall (1993), may be used by one of ordinary skill in the art. In an embodiment of any of the above-described processes, the compound is not previously known to bind to a GALR3 receptor. This invention also provides a compound determined by any of the above-described processes.

This invention further provides a method of measuring GALR3 receptor activation in an oocyte expression system such as a Xenopus oocyte or melanophore. In an embodiment, receptor activation is determined by measurement of ion channel activity, e.g., using the voltage clamp technique (Stühmer, 1992). In an embodiment, receptor activation is determined by the measurement of inward potassium current. In the experiments described hereinbelow, receptor activation was determined by measurement of inward potassium current in the presence of elevated external potassium levels. However, this invention also provides a method of determining GALR3 receptor activation by measurement of outward potassium current in the presence of low (i.e., physiologic) external potassium levels, using similar methods, which are well-known in the art.

Expression of genes in Xenopus oocytes is well known in the art (A. Coleman, *Transcription and Translation: A Practical Approach* (B. D. Hanes, S. J. Higgins, eds., pp 271–302, IRL Press, Oxford, 1984; Y. Masu et al., *Nature* 329:21583–21586, 1994) and is performed using microinjection of native mRNA or in vitro synthesized mRNA into frog oocytes. The preparation of in vitro synthesized mRNA can be performed by various standard techniques (J. Sambrook et al., *Molecular Cloning: A Laboratory Manual*, Second Edition, Cold Spring Harbor Laboratory, Cold Spring Harbor, N.Y., 1989) including using T7 polymerase with the mCAP RNA capping kit (Stratagene). The use of DNA vectors that include 5' and 3' untranslated (UT) regions of Xenopus β-globin gene flanking the coding region of the gene of interest has been found to increase the level of expression in Xenopus oocytes (Linman, et al., 1992).

In an embodiment of any of the above-described processes or methods, the cell is a non-mammalian cell such as an insect cell or Xenopus cell. In a further embodiment of the invention, the cell is a mammalian cell. In another embodiment of the invention, the mammalian cell is non-neuronal in origin. In still further embodiments of the invention, the non-neuronal cell is a COS-7 cell, a 293 human embryonic kidney cell, a LM(tk−) cell, a mouse Y1 cell, a CHO cell, or an NIH-3T3 cell.

This invention provides a pharmaceutical composition comprising a compound identified by the above-described methods and a pharmaceutically acceptable carrier.

In an embodiment of the above-described methods, the cell is non-neuronal in origin. In a further embodiment, the non-neuronal cell is a COS-7 cell, 293 human embryonic kidney cell, CHO cell, NIH-3T2 cell or LM(tk−) cell.

In one embodiment of the above-described methods, the compound is not previously known to bind to a GALR3 receptor.

This invention provides a GALR3 receptor agonist detected by the above-described methods. This invention provides a GALR3 receptor antagonist detected by the above-described methods. In an embodiment the cell is a non-mammalian cell, for example, a Xenopus oocyte or melanophore. In another embodiment the cell is a neuronal cell, for example, a glial cell line such as CG. In an embodiment, the cell is non-neuronal in origin. In a further embodiment, the cell is a Cos-7 or a CHO cell, a 293 human embryonic kidney cell, an LM(tk−) cell or an NIH-3T3 cell.

This invention provides a pharmaceutical composition comprising a drug candidate identified by the above-described methods and a pharmaceutically acceptable carrier.

This invention provides a method for determining whether a chemical compound is a GALR3 antagonist which comprises: (a) administering to an animal a GALR3 agonist and measuring the amount of food intake in the animal; (b) administering to a second animal both the GALR3 agonist and the chemical compound, and measuring the amount of food intake in the second animal; and (c) determining whether the amount of food intake is reduced in the presence of the chemical compound relative to the amount of food intake in the absence of the compound, so as to thereby determine whether the compound is a GALR3 antagonist.

This invention further provides a method of screening a plurality of chemical compounds to identify a chemical compound which is a GALR3 antagonist which comprises: (a) administering to an animal a GALR3 agonist and measuring the amount of food intake in the animal; (b) administering to a second animal the GALR3 agonist and at least one chemical compound of the plurality of compounds, and measuring the amount of food intake in the animal; (c) determining whether the amount of food intake is reduced in the presence of at least one chemical compound of the plurality of chemical compounds relative to the amount of food intake in the absence of at least one of the compounds, and if so; (d) separately determining whether each chemical compound is a GALR3 antagonist according to the method described above, so as to thereby determine if the chemical compound is a GALR3 antagonist. In another embodiment the animal is a non-human mammal. In a further embodiment, the animal is a rodent.

This invention provides a method of detecting expression of a GALR3 receptor by detecting the presence of mRNA coding for the GALR3 receptor which comprises obtaining total mRNA from a cell or tissue sample and contacting the mRNA so obtained with the above-described nucleic acid probe under hybridizing conditions, detecting the presence of mRNA hybridized to the probe, and thereby detecting the expression of the GALR3 receptor by the cell or in the tissue.

This invention provides a method of treating an abnormality in a subject, wherein the abnormality is alleviated by administering to the subject an amount of a GALR3 selective compound, effective to treat the abnormality. Abnormalities which may be treated include cognitive disorder, pain, sensory disorder (olfactory, visual), motor coordination abnormality, motion sickness, neuroendocrine disorders, sleep disorders, migraine, Parkinson's disease, hypertension, heart failure, convulsion/epilepsy, traumatic brain injury, diabetes, glaucoma, electrolyte imbalances, respiratory disorders (asthma, emphysema) depression, reproductive disorders, gastric and intestinal ulcers, gastroesophageal reflux disorder, gastric hypersecretion, gastrointestinal motility disorders (diarrhea), inflammation, immune disorders, and anxiety. In one embodiment the compound is an agonist. In another embodiment the compound is an antagonist.

This invention provides a method of treating an abnormality in a subject, wherein the abnormality is alleviated by the inhibition of a GALR3 receptor which comprises administering to a subject an effective amount of the above-described pharmaceutical composition effective to decrease the activity of the GALR3 receptor in the subject, thereby treating the abnormality in the subject. In an embodiment, the abnormality is obesity. In another embodiment, the abnormality is bulimia.

This invention provides a method of treating an abnormality in a subject wherein the abnormality is alleviated by the activation of a GALR3 receptor which comprises administering to a subject an effective amount of the above-described pharmaceutical composition effective to activate the GALR3 receptor in the subject. In an embodiment, the abnormal condition is anorexia.

In another embodiment, the compound binds selectively to a GALR3 receptor. In yet another embodiment, the compound binds to the GALR3 receptor with an affinity greater than ten-fold higher than the affinity with which the compound binds to a GALR1 receptor. In a still further embodiment, the compound binds to the GALR3 receptor with an affinity greater than ten-fold higher than the affinity with which the compound binds to a GALR2 receptor.

This invention provides a method of detecting the presence of a GALR3 receptor on the surface of a cell which comprises contacting the cell with the above-described antibody under conditions permitting binding of the antibody to the receptor, detecting the presence of the antibody bound to the cell, and thereby detecting the presence of a GALR3 receptor on the surface of the cell.

This invention provides a method of determining the physiological effects of varying levels of activity of GALR3 receptors which comprises producing a transgenic nonhuman mammal whose levels of GALR3 receptor activity are varied by use of an inducible promoter which regulates GALR3 receptor expression.

This invention provides a method of determining the physiological effects of varying levels of activity of GALR3 receptors which comprises producing a panel of transgenic nonhuman mammals each expressing a different amount of GALR3 receptor.

This invention provides a method for identifying an antagonist capable of alleviating an abnormality wherein the abnormality is alleviated by decreasing the activity of a GALR3 receptor comprising administering a compound to the above-described transgenic nonhuman mammal and determining whether the compound alleviates the physical and behavioral abnormalities displayed by the transgenic nonhuman mammal as a result of overactivity of a GALR3 receptor, the alleviation of the abnormality identifying the compound as an antagonist.

This invention provides an antagonist identified by the above-described methods. This invention provides a pharmaceutical composition comprising an antagonist identified by the above-described methods and a pharmaceutically acceptable carrier.

This invention provides a method of treating an abnormality in a subject wherein the abnormality is alleviated by decreasing the activity of a GALR3 receptor which comprises administering to a subject an effective amount of the above-described pharmaceutical composition, thereby treating the abnormality.

This invention provides a method for identifying an agonist capable of alleviating an abnormality in a subject wherein the abnormality is alleviated by increasing the activity of a GALR3 receptor comprising administering a compound to a transgenic nonhuman mammal and determining whether the compound alleviates the physical and behavioral abnormalities displayed by the transgenic nonhuman mammal, the alleviation of the abnormality identifying the compound as an agonist.

This invention provides an agonist identified by the above-described methods.

This invention provides a pharmaceutical composition comprising an agonist identified by the above-described methods and a pharmaceutically acceptable carrier.

This invention provides a method for treating an abnormality in a subject wherein the abnormality is alleviated by increasing the activity of a GALR3 receptor which comprises administering to a subject an effective amount of the above-described pharmaceutical composition, thereby treating the abnormality.

This invention provides a method for diagnosing a predisposition to a disorder associated with the activity of a specific human GALR3 receptor allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human GALR3 receptor and labelled with a detectable marker; (e) detecting labelled bands which have hybridized to DNA encoding a human GALR3 receptor labelled with a detectable marker to create a unique band pattern specific to the DNA of subjects suffering from the disorder; (f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

In an embodiment, a disorder associated with the activity of a specific human GALR3 receptor allele is diagnosed. In another embodiment, the above-described method may be used to identify a population of patients having a specific GALR3 receptor allele, in which population the disorder may be alleviated by administering to the subjects a GALR3-selective compound.

This invention provides a method of preparing the purified GALR3 receptor which comprises: (a) inducing cells to express GALR3 receptor; (b) recovering the receptor from the induced cells; and (c) purifying the receptor so recovered.

This invention provides a method of preparing a purified GALR3 receptor which comprises: (a) inserting nucleic acid encoding the GALR3 receptor in a suitable vector; (b) introducing the resulting vector in a suitable host cell; (c) placing the resulting cell in suitable condition permitting the production of the isolated GALR3 receptor; (d) recovering the receptor produced by the resulting cell; and (e) purifying the receptor so recovered.

This invention provides a method of modifying feeding behavior of a subject which comprises administering to the subject an amount of a compound which is a galanin receptor agonist or antagonist effective to increase or decrease the consumption of food by the subject so as to thereby modify feeding behavior of the subject. In one embodiment, the compound is a GALR3 receptor antagonist and the amount is effective to decrease the consumption of food by the subject. In another embodiment the compound is administered in combination with food.

In yet another embodiment the compound is a GALR3 receptor agonist and the amount is effective to increase the consumption of food by the subject. In a still further embodiment, the compound is administered in combination with food. In other embodiments the subject is a vertebrate, a mammal, a human or a canine.

In one embodiment, the compound binds selectively to a GALR3 receptor. In another embodiment, the compound binds to the GALR3 receptor with an affinity greater than ten-fold higher than the affinity with which the compound binds to a GALR1 receptor. In another embodiment, the compound binds to the GALR3 receptor with an affinity greater than ten-fold higher than the affinity with which the compound binds to a GALR2 receptor. In yet another embodiment, the compound binds to the GALR3 receptor with an affinity greater than one hundred-fold higher than the affinity with which the compound binds to a GALR1 receptor. In another embodiment, the compound binds to the GALR3 receptor with an affinity greater than one hundred-fold higher than the affinity with which the compound binds to a GALR2 receptor.

This invention provides a method of treating Alzheimer's disease in a subject which comprises administering to the subject an amount of a compound which is a galanin receptor antagonist effective to treat the subject's Alzheimer's disease. In one embodiment, the galanin receptor antagonist is a GALR3 receptor antagonist and the amount of the compound is effective to treat the subject's Alzheimer's disease.

This invention provides a method of producing analgesia in a subject which comprises administering to the subject an amount of a compound which is a galanin receptor agonist effective to produce analgesia in the subject. In another embodiment, the galanin receptor agonist is a GALR3 receptor agonist and the amount of the compound is effective to produce analgesia in the subject.

This invention provides a method of decreasing nociception in a subject which comprises administering to the subject an amount of a compound which is a GALR3 receptor agonist effective to decrease nociception in the subject.

This invention provides a method of treating pain in a subject which comprises administering to the subject an amount of a compound which is a GALR3 receptor agonist effective to treat pain in the subject.

This invention provides a method of treating diabetes in a subject which comprises administering to the subject an amount of a compound which is a GALR3 receptor antagonist effective to treat diabetes in the subject.

This invention provides a method of decreasing feeding behavior of a subject which comprises administering a compound which is a GALR3 receptor antagonist and a compound which is a Y5 receptor antagonist, the amount of such antagonists being effective to decrease the feeding behavior of the subject. In an embodiment, the GALR3 antagonist and the Y5 antagonist are administered in combination. In another embodiment, the GALR3 antagonist and the Y5 antagonist are administered once. In another embodiment, the GALR3 antagonist and the Y5 antagonist are administered separately. In still another embodiment, the GALR3 antagonist and the Y5 antagonist are administered once. In another embodiment, the galanin receptor antagonist is administered for about 1 week to 2 weeks. In another embodiment, the Y5 receptor antagonist is administered for about 1 week to 2 weeks.

In yet another embodiment, the GALR3 antagonist and the Y5 antagonist are administered alternately. In another embodiment, the GALR3 antagonist and the Y5 antagonist are administered repeatedly. In a still further embodiment, the galanin receptor antagonist is administered for about 1 week to 2 weeks. In another embodiment, the Y5 receptor antagonist is administered for about 1 week to 2 weeks. This invention also provides a method as described above, wherein the compound is administered in a pharmaceutical composition comprising a sustained release formulation.

This invention will be better understood from the Experimental Details which follow. However, one stilled in the art will readily appreciate that the specific methods and results discussed are merely illustrative of the invention as described more fully in the claims which follow thereafter.

Experimental Details

Materials and Methods

Cloning and Sequencing a Novel Rat Galanin Receptor Fragment

A rat hypothalamus CDNA library in lambda ZAP II (≈2.5×$10^6$ total recombinants; Stratagene, LaJolla, Calif.) was screened using overlapping transmembrane (TM) oligonucleotide probes (TM 1, 2, 3, 4, 5, 6 and 7) derived from the rat GALR2 receptor cDNA. Overlapping oligomers were labeled with [$^{32}$P]DATP and [$^{32}$]dCTP by synthesis with the large fragment of DNA polymerase, and comprised the following sequences:

```
TM1:
(+)strand:
5'TTGTACCCCTATTTTTCGCGCTCATCTTCCTCGTGGGCACCGTGG-3'        (SEQ ID NO: 6)

(-)strand:
5'-AGCACCGCCAGCACCAGCGCGTTGCCCACGGTGCCCACGAGGAAG-3'       (SEQ ID NO: 7)

TM2:
(+)strand:
5'-TCAGCACCACCAACCTGTTCATCCTCAACCTGGGCGTGGCCGACCTGTGT-3'  (SEQ ID NO: 8)

(-)strand:
5'-GGCCTGGAAAGGCACGCAGCACAGGATGAAACACAGGTCGGCCACGCCCA-3'  (SEQ ID NO: 9)

TM3:
(+)strand:
5'-CTGCAAGGCTGTTCATTTCCTCATCTTTCTCACTATGCACGCCAG-3'       (SEQ ID NO: 10)

(-)strand:
5'-GGAGACGGCGGCCAGCGTGAAGCTGCTGGCGTGCATAGTGAGAAA-3'       (SEQ ID NO: 11)

TM4:
(+)strand
5'-AACGCGCTGGCCGCCATCGGGCTCATCTGGGGGCTAGCACTGCTC-3'       (SEQ ID NO: 12)

(-)strand
5'-AGTAGCTCAGGTAGGGCCCGGAGAAGAGCAGTGCTAGCCCCCAGA-3'       (SEQ ID NO: 13)

TM5:
(+)strand:
5'-AGCCATGGACCTCTGCACCTTCGTCTTTAGCTACCTGCTGCCAGT-3'       (SEQ ID NO: 14)
```

-continued

```
(-)strand:
5'-CGCATAGGTCAGACTGAGGACTAGCACTGGCAGCAGGTAGCTAAA-3'        (SEQ ID NO: 15)

TM6:
(+)strand:
5'-GATCATCATCGTGGCGGTGCTTTTCTGCCTCTGTTGGATGCCCCA-3'        (SEQ ID NO: 16)

(-)strand:
5'-CCACACGCAGAGGATAAGCGCGTGGTGGGGCATCCAACAGAGGCA-3'        (SEQ ID NO: 17)

TM7:
(+)strand:
5'-GTTGCGCATCCTTTCACACCTAGTTTCCTATGCCAACTCCTGTGT-3'        (SEQ ID NO: 18)

(-)strand:
5'-AGACCAGAGCGTAAACGATGGGGTTGACACAGGAGTTGGCATAGGA-3'       (SEQ ID NO: 19).
```

Hybridization of phage lifts was performed at reduced stringency conditions: 40° C. in a solution containing 37.5% formamide, 5×SSC (1×SSC is 0.15M sodium chloride 0.015M sodium citrate), 1×Denhardt's solution (0.02% polyvinylpyrrolidone, 0.02% Ficoll, 0.02% bovine serum albumin), and 25 μg/μL sonicated salmon sperm DNA. The filters were washed at 45° C. in 0.1×SSC containing 0.1% sodium dodecyl sulfate and exposed at −70° C. to Kodak BioMax film in the presence of an intensifying screen. Lambda phage clones hybridizing with the probes were plaque purified and pBluescript recombinant DNAs were excision-rescued from λ Zap II using helper phage Re704, as described by the manufacturer's protocol (Rapid Excision Kit, Stratagene, LaJolla, Calif.). Insert size was confirmed by restriction enzyme digest analysis. The cDNA insert was sequenced on both strands by cycle sequencing with AmpliTaq DNA Polymerase, FS (Perkin Elmer) and products run on an automated fluorescent sequencer, the ABI Prism 377 Sequencer (ABI). Nucleotide and peptide sequence analyses were performed using the Wisconsin Package (GCG, Genetics Computer Group, Madison, Wis.). Sequence analyses indicated that one clone, named rHY35a, contained an open reading frame from the starting MET codon to the middle of a predicted seventh transmembrane domain. Because the high degree of identity of rHY35a to rGALR1 and rGALR2 indicated that it might represent a fragment of a novel galanin receptor (referred to herein as "GALR3"), PCR primers directed to the amino terminus (forward primer) and first extracellular loop (reverse primer) of each of the corresponding receptor cDNA were synthesized having the following sequences:

```
rGALR1:
(forward primer):
5'-CCTCAGTGAAGGGAATGGGAGCGA-3'      (SEQ ID NO: 20);

(reverse primer):
5'-GTAGTGTATAAACTTGCAGATGAAGGC-3'   (SEQ ID NO: 21);

rGALR2:
(forward primer):
5'-ATGAATGGCTCCGGCAGCCAGGG-3'       (SEQ ID NO: 22);

(reverse primer):
5'-TTGCAGAGCAGCGAGCCGAACAC-3'       (SEQ ID NO: 23);

and
```

-continued

```
rHY35a (i.e., rat GALR3):
(forward primer):
5'-GGCTGACATCCAGAACATTTCGCT-3'     (SEQ ID NO: 24);

(reverse primer):
5'-CAGATGTACCGTCTTGCACACGAA-3'     (SEQ ID NO: 25).
```

Polymerase Chain Reaction (PCR) of cDNA

Total RNA was prepared from RIN14B cells (ATCC No. CCL 89) by a modification of the guanidine thiocyanate method (Chirgwin et al., 1979). Poly $A^+$ RNA was purified with a FastTrack kit (Invitrogen Corp., San Diego, Calif.) and converted to single-stranded cDNA by random priming using Superscript reverse transcriptase (BRL, Gaithersburg, Md.). An aliquot of the first strand cDNA was diluted (1:50) in a 50 μL PCR reaction mixture containing a combination of Tar and Pwo DNA polymerases in the buffer supplied by the manufacturer (for the Expand Long Template PCR System, Boehringer Mannheim), and 300 nM each of the amino terminus and first extracellular loop rGALR3 (rHY35a) primers described above. The PCR amplification reaction was performed under the following conditions: 30 sec. at 94° C. and 1 min. 30 sec. at 68° C. for 40 cycles, with a pre- and post-incubation of 5 min. at 95° C. and 2 min. 30 sec. at 68° C. , respectively. In order to control for the amplification of DNA (potentially carried over during the RNA extraction), control PCR reactions were run in parallel using RIN14B RNA prepared as above but without reverse transcriptase, and thus not converted to cDNA. The PCR products were separated on a 1.0% agarose gel and stained with ethidium bromide.

Construction and PCR Screening of a RIN14B Cell Line Plasmid Library

Total RNA was prepared from RIN14B cells by a modification of the guanidine thiocyanate method (Chirgwin et al., 1979). Poly $A^+$ RNA was purified with a FastTrack kit (Invitrogen Corp., San Diego, Calif.). Double stranded (ds) cDNA was synthesized from 4 μg of poly $A^+$ RNA according to Gubler and Hoffman (1983) with minor modifications. The resulting cDNA was ligated to BstXI/EcoRI adaptors (Invitrogen Corp.) and the excess adaptors removed by exclusion column chromatography. High molecular weight fractions of size-selected ds-cDNA were ligated in pEXJ.BS (an Okayama and Berg expression vector) and electroporated in *E.coli* MC 1061 (Gene Pulser, Biorad). A total of $0.9\times10^6$ independent clones with an insert mean size of 3.4 kb were generated. The library was plated on agar plates (Ampicillin selection) in 216 pools of ~4,000 independent clones. After 18 hours amplification, the bacteria from each pool were scraped, resuspended in 4 mL of LB media, and 1.5 mL processed for plasmid purification (Qiaprep, Qiagen, Inc., Chatsworth, Calif.). Aliquots of each bacterial pool were stored at −85° C. in 20% glycerol.

Glycerol stocks (2 μL) of the 216 primary pools for the RIN14B plasmid library (designated "F") were screened for rGALR3 by PCR using a forward primer from the third transmembrane domain of rGALR3 (5'-CATCTGCTCATCTACCTCACCATG-3' (SEQ ID NO: 26)) and a reverse primer from third intracellular loop of rGALR3 (5'-CATAGGAAACATAGCGTGCGTCCG-3' (SEQ ID NO: 27)). PCR was performed with the Expand Long Template PCR System, as described in the preceding section. Two positive pools, F105 and F212, were subjected to further PCR analyses, using a forward primer to the amino terminus of rat GALR3 (described above) with a reverse primer from the third intracellular loop (described above), as well as vector-anchored PCR (see below). These PCR analyses indicated that, although these clones were full-length, they were in the incorrect orientation in the expression vector (pEXJ.BS). Although these pools were not further subdivided, the sequence missing from clone rHY35a (i.e., from the middle of TM7 through the stop codon) was determined from the F105 clone, using vector-anchored PCR, as described below.

Vector-anchored PCR

To determine the orientation and size of the F105 cDNA insert (including the coding region, 5' untranslated (UT) and 3' UT regions) PCR was conducted on glycerol stocks (2 μL) using combinations of vector-derived primers and gene-specific primers. The vector-derived forward primer sequence was 5'-AAGCTTCTAGAGATCCCTCGACCTC-3' (SEQ ID NO: 28); the reverse primer sequence was 5'-AGGCGCAGAACTGGTAGGTATGGAA-3' (SEQ ID NO: 29). The rGALR3-specific forward primer (in the sixth transmembrane domain) was 5'-GCTCATCCTCTGCTTCTGGTACG-3' (SEQ ID NO: 30); the reverse primer (in the first extracellular loop) was 5'-CAGATGTACCGTCTTGCACACGAA-3' (SEQ ID NO: 31). PCR was performed with the Expand Long Template PCR System, as described above. The PCR products were separated on a 1.0% agarose gel and stained with ethidium bromide.

A 1.2 kb vector-anchored PCR product generated from pool F105 using the sixth TM forward primer from rGALR3 and the vector-derived reverse primer was isolated from a 1% TAE gel using a GENECLEAN III kit (BIO 101, Vista, Calif.) and sequenced using AmpliTaq DNA Polymerase, FS (Perkin Elmer). Sequencing reactions were run on an ABI PRISM 377 DNA Sequencer and analyzed using the Wisconsin Package (GCG, Genetics Computer Group, Madison, Wis.). The sequence information from this vector-anchored PCR product corresponding to the predicted 3' end of the novel receptor gene indicated an overlap with rHY35a within the first half of TM7. Downstream of this overlap was new sequence, consistent with the second half of TM7 and the carboxy terminus, including an in-frame stop codon. Based on this newly acquired sequence, a reverse primer, within the 3'UT, was synthesized (also containing a BamHI site at the 5' end, as indicated by the underline): 5'-CGA <u>GGATCC</u>CAACTTTGCCTCTGCTTTTTGGTGG-3' (SEQ ID NO: 32).

Construction and PCR Screening of a Rat Hypothalamus Plasmid Library

Total RNA was prepared from rat hypothalami by a modification of the guanidine thiocyanate method (Chirgwin, 1979). Poly $A^+$ RNA was purified using a Fast-Track kit (Invitrogen Corp., San Diego, Calif.). Double stranded (ds) cDNA was synthesized from 6 μg of poly $A^+$ RNA according to Gubler and Hoffman (1983) with minor modifications. The resulting cDNA was ligated to BstXI/EcoRI adaptors (Invitrogen Corp.) and the excess adaptors removed by exclusion column chromatography. High molecular weight fractions of size-selected ds-cDNA were ligated in pEXJ.T7 (an Okayama and Berg expression vector modified from pcEXV (Miller & Germain, 1986) to contain BstXI and other additional restriction sites and a T7 promoter (Stratagene) and electroporated in *E.coli* MC 1061 (Gene Pulser, Biorad). A total of $1.2\times10^6$ independent clones with a mean insert size of 3.2 kb were generated. The library (designated "K") was plated on agar plates (Ampicillin selection) in 373 primary pools of ~3,200 independent clones. After 18 hours amplification, the bacteria from each pool were scraped, resuspended in 4 mL of LB media and 0.75 mL processed for plasmid purification (QIAwell-96 ultra, Qiagen, Inc., Chatsworth, Calif.). Aliquots of each bacterial pool were stored at −85° C. in 20% glycerol.

To screen the library for galanin binding, COS-7 cells were plated in slide chambers (Lab-Tek) in Dulbecco's modified Eagle medium (DMEM) supplemented with 10% calf serum, 100 U/mL of penicillin, 100 ug/mL streptomycin, 2 mM L-glutamine (DMEM-C) and grown at 37° C. in a humidified 5% $CO_2$ atmosphere for 24 hours before transfection. Cells were transfected with miniprep DNA prepared from the primary pools (~3,200 cfu/pool) of the rat hypothalamus cDNA library ("K" library ) using a modification of the DEAE-dextran method (Warden & Thorne, 1968). Pools containing GALR1 and GALR2 were identified by PCR prior to screening. The galanin binding assay was carried out after 48 hours. Cells were rinsed twice with phosphate-buffered saline (PBS) then incubated with 2 nM $^{125}$I-porcine galanin (NEN; specific activity ~2200 Ci/mmol) in 20 mM HEPES-NaOH, pH 7.4, containing 1.26 mM $CaCl_2$, 0.81 mM $MgSO_4$, 0.44 mM $KH_2PO_4$, 5.4 mM KCl, 10 mM NaCl, 0.1% BSA, and 0.1% bacitracin for one hour at room temperature. After rinsing and fixation in 2.5% glutaraldehyde, slides were rinsed in PBS, air-dried, and dipped in photoemulsion (Kodak, NTB-2). After a 4 day exposure slides were developed in Kodak D19 developer, fixed, and coverslipped (Aqua-Mount, Lerner Laboratories), then inspected for positive cells by brightfield microscopy (Leitz Laborlux, 25×magnification).

PCR Screening of the Rat Hypothalamus cDNA Library

Glycerol stocks of the primary pools were combined into 40 superpools of 10 primary pools and screened for rGALR3 by PCR using the same primers as described for the screening of the RIN14B plasmid library (see above). Primary pools from positive superpools (#3 and #17) were inspected for galanin binding using the photoemulsion binding assay described above and screened by PCR. The slide corresponding to pool K163 exhibited positive galanin binding. Pool K163 was then subjected to PCR with internal rGALR3 primers (TM3 forward primer and third intracellular loop reverse primer; described above), full-length primers (forward primer to the amino terminus, at the starting MET, and reverse primer to the 3' UT (containing a Bam HI site as above)) and with the vector and gene-specific primers (preceding section). These PCR analyses indicated that the primary pool K163 contained a full-length coding region for rGALR3 in the correct orientation in the expression vector, pEXJ.T7. Pool K163 was further analyzed by PCR and shown to contain GALR3 but not GALR1 nor GALR2, indicating that a novel galanin receptor cDNA was present in the pool and responsible for the galanin binding. The PCR primers used to confirm the absence of GALR1 and GALR2 in the pool are described below:

rGALR1:

Forward primer, KS-1311:

5'-CCTCAGTGAAGGGAATGGGAGCGA (SEQ ID NO: 33);

Reverse primer, KS-1447:

5'-CTTGCTTGTACGCCTTCCGGAAGT (SEQ ID NO: 34);

Human GALR1:

Forward primer, KS-1177:

5'-TGGGCAACAGCCTAGTGATCACCG-3' (SEQ ID NO: 35);

Reverse primer, KS-1178:

5'-CTGCTCCCAGCAGAAGGTCTGGTT-3' (SEQ ID NO: 36);

rGALR2:

Forward primer, KS-1543:

5'-ATGAATGGCTCCGGCAGCCAGGG-3' (SEQ ID NO: 37);

Reverse primer, KS-1499:

5'-TTGGAGACCAGAGCGTAAACGATGG-3' (SEQ ID NO: 38).

The primary pool K163 was further subdivided and screened by PCR. One positive subpool, 163-30, was subdivided into 15 pools of 150 clones and 15 pools of 500 clones and plated on agar plates (ampicillin selection). Colonies were transferred to nitrocellulose membranes (Schleicher and Schuell, Keene, N.H.), denatured in 0.4 N NaOH, 1.5 M NaCl, renatured in 1M Tris, 1.5 M NaCl, and UV cross-linked. Filters were hybridized overnight at 40° C. in a buffer containing 50 % formamide, 5×SSC, 7 mM TRIS, 1×Denhardt's solution and 25 $\mu$g/mL salmon sperm DNA (Sigma Chemical Co.) and $10^6$ cpm/ml of overlapping 45-mer oligonucleotide probes, filled-in using [$\alpha$-$^{32}$P ]dCTP and [$\alpha$-$^{32}$P]DATP (800Ci/mmol, NEN) and Klenow fragment of DNA polymerase (Boehringer Mannheim). The following probe sequence is directed to the amino terminus of rGALR3:

from the sense strand:

5'-AGATGGCTGACATCCAGAACATTTCGCTGGACAG CCCAGGGAGCG-3' (SEQ ID NO: 39);

from the antisense strand:

5'-ATCACAGGCACTGCCACAGCCCCTACGCTCCCTG GGCTGTCCAGCG-3' (SEQ ID NO: 40).

Filters were washed 2×15 minutes at room temperature in 2×SSC, 0.1% SDS, 2×15 minutes at 50° C. in 0.1×SSC, 0.1% SDS, and exposed to BioMax MS X-ray film (Kodak) with corresponding Kodak intensifying screens for 6 hours. One positive colony, 163-30-17, was amplified overnight separately in 100 mL LB media and in 100 mL TB media and processed for plasmid purification using a standard alkaline lysis miniprep procedure followed by a PEG precipitation. Clone K163-30-17 was sequenced on both strands using AmpliTaq DNA Polymerase, FS (Perkin Elmer). Sequencing reactions were run on an ABI PRISM 377 DNA Sequencer and analyzed using the Wisconsin Package (GCG, Genetics Computer Group, Madison, Wis.). Clone K163-30-17 was given the designation K1086 and deposited with the ATCC (Accession No. 97747).

Expression in COS 7 Cells for Whole Cell-slide Binding

To test the ability of K163-30-17 to confer galanin binding, COS-7 cells were plated in slide chambers (Lab-Tek) in Dulbecco's modified Eagle medium (DMEM) supplemented with 10% calf serum, 100 U/mL of penicillin, 100 $\mu$g/mL streptomycin, 2 mM L-glutamine (DMEM-c) and grown at 37° C. in a humidified 5% $CO_2$ atmosphere for 24 hours before transfection. Cells were transfected with 1 $\mu$g of miniprep DNA from K163-30-17 or vector control using a modification of the DEAE-dextran method (Warden and Thorne, 1968). 48 hours after transfection, cells were rinsed with phosphate-buffered saline (PBS) then incubated with 2 nM $^{125}$I-porcine galanin (NEN; specific activity ~2200 Ci/mmol) in 20 mM HEPES-NaOH, pH 7.4, containing 1.26 mM $CaCl_2$, 0.81 mM $MgSO_4$, 0.44 mM $KH_2PO_4$, 5.4 mM KCl, 10 mM NaCl, 0.1% BSA, and 0.1% bacitracin for one hour at room temperature. After rinsing and fixation in 2.5% glutaraldehyde, binding of $^{125}$I-galanin to cells on the slide was detected by autoradiography using BioMax MS film (Kodak) and an intensifying screen (Kodak). The signal from K163-30-17 transfected cells was compared with the signal from control vector transfected cells.

Cloning and Sequencing a Novel Human Galanin Receptor Fragment

A human placenta genomic library in λ dash II (≈$1.5\times10^6$ total recombinants; Stratagene, LaJolla, Calif.) was screened using the same set of overlapping oligonucleotide probes to TM regions 1–7 of rat GALR2 and under the same hybridization and wash conditions as described for screening the rat hypothalamus cDNA library (supra). Lambda phage clones hybridizing with the probe were plaque purified and DNA was prepared for Southern blot analysis (Southern, 1975; Sambrook et al., 1989).

One phage clone, plc2la, contained a 2.7 kb KpnI/EcoRI fragment which hybridized with the rat GALR2 TM2 oligonucleotide probe and was subsequently subcloned into a pUC vector. Nucleotide sequence analysis was accomplished by sequencing both strands using cycle sequencing with AmpliTaq DNA Polymerase, FS (Perkin Elmer) and products run on the automated fluorescent sequencer, the ABI Prism 377 Sequencer (ABI), and sequence analyses were performed using the Wisconsin Package (GCG, Genetics Computer Group, Madison, Wis.). DNA sequence analysis indicated greatest homology to the rat and human GALR1 and GALR2 genes. This clone was a partial intron-containing gene fragment, encoding the starting MET through to an intron in the second intracellular loop (i.e., TM ¾ loop).

Isolation of the Full-length Human GALR3 Receptor Gene

Sequence analyses of the cloned human genomic fragment indicated the presence of a open reading frame from the starting MET codon down to a predicted intron in the second intracellular loop, with a nucleotide identity of 88% (93% amino acid identity) with the rat GALR3 receptor described above (thus establishing this human genomic clone to be the human homologue of rat GALR3). Although this human genomic fragment was not full-length and contained an intron downstream of TM3, it is anticipated that a molecular biologist skilled in the art may isolate the full-length, intronless version of the human GALR3 receptor gene using standard molecular biology techniques and approaches such as those briefly described below:

Approach #1: Using PCR to screen commercial human cDNA phage libraries and in-house human cDNA plasmid libraries with primers to the human GALR3 sequence (forward primer in amino terminus, 5'-ATGGCTGATGCCCAGAACATTTCAC-3' (SEQ ID NO: 41), and reverse primer in first extracellular loop, 5'-AGCCAGGCATCCAGCGTGTAGAT-3' (SEQ ID NO: 42), we have identified two commercial libraries and two proprietary plasmid libraries that contain at least part of the human GALR3 gene, as follows:

human fetal brain CDNA lambda ZAPII library (Stratagene);

human testis CDNA lambda ZAPII library (Stratagene);

human hypothalamus cDNA plasmid library (proprietary)—3 superpools identified; and human hippocampus CDNA plasmid library (proprietary)—3 superpools identified.

One may determine whether these libraries contain full-length human GALR3 by: (1) obtaining a purified clone from the lambda libraries by plaque-purification and then conducting hybridization screening using probes derived from rat GALR3 under reduced stringency, using standard protocols and/or (2) using PCR to determine which pool of the human plasmid library superpools contain the gene and then conducting vector-anchor PCR (as described in this patent) to determine if these cDNAs are full-length. One problem which may arise with vector-anchored PCR is a false-positive result, in which the PCR product size is consistent with a full-length clone but the product actually contains an intron in the second intracellular loop. In this case, sequencing of this product would identify whether this product contains the intron or is intronless and full-length (also see Approach #2 below).

Approach #2: We have also determined that the phage clone containing MET thru the intron in the second intracellular loop (i.e., TM¾ loop), plc21a (see above), also contains at least part of the 3' end of the gene, by using hybridization at reduced stringency with a probe to the third extracellular loop (TM 6/7) derived from the rat GALR3 sequence:

5'-ACGGTCGCTTCGCCTTCAGCCCGGCCACCTACGCCTGTCGCCTGG-3' (SEQ ID NO: 43).

Standard molecular biology techniques may be used to subclone either the entire intron-containing full-length human GALR3 (with confirmation that it contains an in-frame stop codon) or subclone the part of the gene from the intron in the second intracellular loop through the stop codon. This approach would permit one to utilize sequence around the termination codon to design a primer which can be used with the primer around the starting MET, to generate the full-length intronless human GALR3 gene, using human cDNA as the target template. Alternatively, one may use restriction enzymes to remove the intron and some adjacent coding region from the intron-containing human GALR3 gene, and then replace the removed coding region by inserting a restriction enzyme-digested PCR fragment amplified from a tissue shown to express the intronless form of the receptor.

Approach #3: As yet another alternative method, one could utilize 3' RACE to generate a PCR product from human cDNA expressing human GALR3 (e.g., human brain), using a forward primer derived from known sequence between the starting MET thru the second intracellular loop (from the fragment already isolated). Such a PCR product could then be sequenced to confirm that it contains the rest of the coding region (without an intron), and then attached to the 5' end of the molecule, using an overlapping restriction site, or alternatively, its sequence could be used to design a reverse primer in the predicted 3' UT region to generate the full-length, intronless human GALR3 receptor gene with use of the primer at the starting MET codon and using human cDNA as target template.

To this end, we have also determined that the phage clone containing MET through the intron in the second intracellular loop (i.e. TM ¾ loop), plc2la (see above), also contains at least part of the 3' end of the gene, by us ng hybridization at reduced stringency with probes either to the third extracellular loop (TM 6/7 ) or to TM 4, derived from the rat GALR3 sequence:

5'-ACGGTCGCTTCGCCTTCAGCCCGGCCACCTACGCCTGTCGCCTGG-3' (SEQ ID NO: 44)

5'-GCGCAACGCGCGCGCCGCCGTGGGGCTCGTGTGGCTGCTGGCGGC-3' (SEQ ID NO: 45).

Another clone, plc14a, which was essentially the same as plc21a (i.e. possessed the identical restriction map and hybridizing bands as plc21a), was further utilized by subcloning a 1.4 kb KpnI fragment which similarly hybridized to the above probes. Since the phage clone, plc14a, also hybridized with a TM⅔ loop probe under high stringency, derived from sequence data of human GALR3 5' fragment (plc21a, see above),

5"-ATCTACACGCTGGATGCCTGGCTCTTTGGGGCCCTCGTCTGCAAG-3' (SEQ ID NO: 46), this 3' fragment (e.g. plc14a) presumably corresponds to the 3' end of human GALR3 and is molecularly linked to the 5' fragment (e.g. plc21a 2.7 kb KpnI/EcoRI clone); however, an intron of unknown size separates the coding region, which is defined on the 5' (2.7 kb KpnI/EcoRI plc2la fragment) and 3' (1.4 kb KpnIplc14a fragment) genomic pieces. Nucleotide sequence analysis was conducted on the 1.4 kb KpnI plc14a fragment, as described above, and indicated greatest homology to the rat and human GALR1 and GALR2 genes.

To obtain sequence information from the region defined by the intersection of these to exons as well as to prove that the 5' and 3' fragments, putatively representing the entire full-length coding region of human GALR3, are molecularly linked, we used a forward oligonucleotide primer located on the 5' Fragment (within ⅔ loop)

5'-ATCTACACGCTGGATGCCCTGGCT-3' (SEQ ID NO: 47) and a reverse oligonucleotide primer located on the 3' fragment (within the predicted 4/5 loop),

5'-CGTAGCGCACGGTGCCGTAGTA-3' (SEQ ID NO: 48), to amplify human brain and liver CDNA (corresponding to 5 ng of poly$^{+}$ RNA). The predicted =250 nts. PCR products were sequenced and demonstrated that: (1) the sequences were identical between brain and liver cDNA, (2) the 5' and 3' genomic fragments are linked and represent the 5' and 3' fragments of the human GALR3 gene, and (3) the sequence obtained defined the junction of the exon containing the starting MET through the ¾ loop (e.g., housed on the 2.7 kb KpnI/EcoRI plc21a subclone) and the exon containing the ¾ loop through the predicted STOP codon (e.g. housed on the 1.4 kb KpnI plc14a subclone). The sequence of this junction demonstrated the presence of a KpnI site, which was utilized in the construction of the full-length gene.

The construction of the full-length human GALR3 gene first involved the generation of the 5' end of the gene using PCR to synthetically create a KpnI site at the 3' end of the PCR product. To this end, we designed a forward oligonucleotide primer located at the starting MET of the 5' fragment and added a consensus Kozak sequence as well as a BamHI site to be used for subcloning:

5'-GATGGATCCGCCACCATGGCTGATGCCCAGAACATTTCAC-3' (SEQ ID NO: 49), and a reverse oligonucleotide primer, within the ¾ loop, containing a KpnI site that generated the joint between the 5' and 3' KpnI fragment:

5'-CAGGTACCTGTCCACGGAGACAGCAGC-3' (SEQ ID NO: 50).

The addition of the KpnI site enabled the attachment of the 3' KpnI fragment but preserved the sequence which was identified from human brain and liver cDNAs.

The forward and reverse primers were used to amplify the 2.7 kb KpnI/EcoRI5' genomic-containing plasmid (plc21a)

using PCR, as described in a previous section but utilizing Expand High Fidelity PCR System (Boehringer Manniheim). The PCR product was isolated from a low melting gel, purified by phenol extraction, digested with BamHI and KpnI and purified further by phenol extraction. This BamHI/KpnI PCR product was subcloned into BamHI/KpnI-digested expression vector, PEXJ, and sequenced. The sequence of the PCR product was identical to that determined for the original genomic fragment. The subclone was then digested with KpnI, treated with calf intestinal alkaline phosphatase, and ligated with the 1.4 KpnI 3' genomic fragment. Correct orientation was determined by both restriction mapping and sequencing. Therefore, the full-length human GALR3 construct contained=1.7 kb genomic insert, containing 1107 bp of coding region and =600 bp of 3' non-coding region.

Northern Blots

Rat multiple tissue northern blots (rat MTN blot, Clontech, Palo Alto, Calif.), containing 2 μg poly $A^+$ RNA, or northern blots containing 5 μg $poly^+$ RNA, either purchased from Clontech or purified from various rat peripheral tissues and brain regions, respectively, were similarly hybridized at high stringency with a probe directed to the amino-terminus of rGalR3 (SEQ ID NO: 39 and 40), according to the manufacturer's specifications. Probe was labeled as previously described (supra), using Klenow fragment of DNA polymerase, except [$\alpha$-$^{32}$P]dCTP and [$\alpha$-$^{32}$P] DATP (3000 Ci/mmol, NEN) were used. Northern blots were reprobed with a randomly-primed β-actin probe to assess quantities of mRNA present in each lane.

Human brain multiple tissue northern blots (MTN brain blots II and III, Clontech, Palo Alto, Calif.) and human peripheral MTN blot (Clontech, Palo Alto, Calif.) carrying mRNA (2 μg) purified from various human brain areas and peripheral tissues, respectively, were hybridized at high stringency with overlapping probes directed to the amino-terminus of hGALR3

5' GATGGCTGATGCCCAGAACATTTCACTG-GACAGCCCAGGGAGTGT 3' (SEQ ID NO: 51) and

5' GACCACAGGCACTGCCACGGCCCCCA-CACTCCCTCGGCTGTCCAG 3' (SEQ ID NO: 52), according to the manufacturer's specifications.

RT-PCR Analyses of GALR3 mRNA

Tissues were homogenized and total RNA extracted using the guanidine isothiocyanate/CsCl cushion method. RNA was then treated with DNase to remove any contaminating genomic DNA and poly $A^+$-selected using FastTrack kit (Invitrogen), according to manufacturer's specifications. cDNA was prepared from mRNA with random hexanucleotide primers using reverse transcriptase Superscript II (BRL, Gaithersburg, Md.). First strand cDNA (corresponding to ≈5 ng of poly $A^+$ RNA) was amplified in a 50 μL PCR reaction mixture with 300 nM of forward (directed to the amino-terminus: SEQ ID NO: 24) and reverse (directed to the third intracellular loop: SEQ ID NO: 27) primers, using the thermal cycling program and conditions described above.

The PCR products were run on a 1.5% agarose gel and transferred to charged nylon membranes (Zetaprobe GT, BioRad), and analyzed as Southern blots. GALR3 primers were screened for the absence of cross-reactivity with the other galanin receptors. Filters were hybridized with a radiolabeled probe directed to the first intracellular loop, 5'-TGCAGCCTGGCCCAAGTGCCTGGCAGGAGCCA-AGCAGTACCACAG-3' (Seq. I.D. No: 53), and washed under high stringency. Labeled PCR products were visualized on X-ray film. Similar PCR and Southern blot analyses were conducted with primers and probes directed to the housekeeping gene, glyceraldehyde phosphate dehydrogenase (G3PDH; Clontech, Palo Alto, Calif.), to normalize the amount of cDNA used from the different tissues.

Production of Recombinant Baculovirus

The coding region of GALR3 may be subcloned into pBlueBacIII into existing restriction sites, or sites engineered into sequences 5' and 3' to the coding region of GALR3, for example, a 5' EcoRI site and a 3' EcoRI site. To generate baculovirus, 0.5 μg of viral DNA (BaculoGold) and 3 μg of GALR3 construct may be co-transfected into $2\times10^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Cell Culture

COS-7 cells are grown on 150 mm plates in DMEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of COS-7 cells are trypsinized and split 1:6 every 3–4 days. Human embryonic kidney 293 cells are grown on 150 mm plates in D-MEM with supplements (minimal essential medium) with Hanks' salts and supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of 293 cells are trypsinized and split 1:6 every 3–4 days. Mouse fibroblast LM(tk–) cells are grown on 150 mm plates in D-MEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of LM(tk–) cells are trypsinized and split 1:10 every 3–4 days.

LM(tk–) cells stably transfected with the GALR3 receptor may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/mL in suspension media (10% bovine calf serum, 10% 10×Medium 199 (Gibco), 9 mM $NaHCO_3$, 25 mM glucose, 2 mM L-glutamine, 100 units/mL penicillin/100 jig/mL streptomycin, and 0.05% methyl cellulose). Cell suspensions are maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/mL) followed by incubation at 37° C., 5% $CO_2$ for 24 hours. Cells prepared in this manner generally yield a robust and reliable response in cAMP radio-immunoassays as further described hereinbelow.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/mL penicillin/100 μg/mL streptomycin) at 37° C., 5% $CO_2$. Stock plates of NIH-3T3 cells are trypsinized and split 1:15 every 3–4 days. Chinese hamster ovary (CHO) cells were grown on 150 mm plates in HAM's F-12 medium with supplements (10% bovine calf serum, 4 mM L-glutamine and 100 units/mL penicillin/100 μg/ml streptomycin) at 37° C., 5% $CO_2$. Stock plates of CHO cells were trypsinized and split 1:8 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

Transfection

All receptor subtypes studied may be transiently transfected into COS-7 cells by the DEAE-dextran method, using 1 μg of DNA /$10^6$ cells (Cullen, 1987). In addition, Schneider 2 Drosophila cells may be cotransfected with vectors containing the receptor gene, under control of a promoter which is active in insect cells, and a selectable resistance gene, eg., the G418 resistant neomycin gene, for expression of the galanin receptor.

Stable Transfection

The GALR3 receptor may be co-transfected with a G-418 resistant gene into the human embryonic kidney 293 cell line by a calcium phosphate transfection method (Cullen, 1987). Stably transfected cells are selected with G-418. GALR3 receptors may be similarly transfected into mouse fibroblast LM(tk−) cells, Chinese hamster ovary (CHO) cells and NIH-3T3 cells, or other suitable host cells. GALR1 receptors were expressed in cells using methods well-known in the art.

Radioligand Binding Assays

Transfected cells from culture flasks are scraped into of 20 mM Tris-HCl, 5 mM EDTA, pH 7.5, and lysed by sonication. The cell lysates are centrifuged at 1000 rpm for 5 min. at 4° C., and the supernatant centrifuged at 30,000×g for 20 min. at 4° C. The pellet is suspended in binding buffer (50 mM Tris-HCl, 5 mM $MgSO_4$, 1 mM EDTA at pH 7.5 supplemented with 0.1% BSA, 2 μg/ml aprotinin, 0.5 mg/ml leupeptin, and 10 μg/ml phosphoramidon). Optimal membrane suspension dilutions, defined as the protein concentration required to bind less than 10% of the added radioligand, are added to 96-well polpropylene microtiter plates containing $^{125}$I-labeled peptide, non-labeled peptides and binding buffer to a final volume of 250 μl. In equilibrium saturation binding assays membrane preparations may be incubated in the presence of increasing concentrations (e.g., 0.1 nM to 4 nM) of [$^{125}$I]porcine galanin (specific activity about 2200 Ci/mmol). The binding affinities of the different galanin analogs may be determined in equilibrium competition binding assays, using 0.1–0.5 nM [$^{125}$I]porcine galanin in the presence of e.g., twelve different concentrations of the displacing ligands. Binding reaction mixtures are incubated for 1 hr at 30° C., and the reaction stopped by filtration through GF/B filters treated with 0.5% polyethyleneimine, using a cell harvester. Radioactivity may be measured by scintillation counting and the data analyzed by a computerized non-linear regression program. Non-specific binding may be defined as the amount of radioactivity remaining after incubation of membrane protein in the presence of 100 nM of unlabeled porcine galanin. Protein concentration may be measured by the Bradford method using Bio-Rad Reagent, with bovine serum albumin as a standard. Such competitive binding assays are well-known in the art, and may also include the use of non-hydrolyzable analogues of GTP, which may reduce the binding of agonists to the GALR3 receptors of the present invention.

The binding assays used to generate the data shown in Table 4 were conducted as described above, with certain modifications. Assays were conducted at room temperature for 120 minutes, and leupeptin, aprotonin and phosphoramidon were omitted from the rat GALR3 assay, while bacitracin was added to 0.1%. In addition, nonspecific binding was defined in the presence of 1 μM porcine galanin.

Functional Assays

Cyclic AMP (cAMP) Formation

The receptor-mediated inhibition of cyclic AMP (cAMP) formation may be assayed in LM(tk−) cells expressing the galanin receptors. Cells are plated in 96-well plates and incubated in Dulbecco's phosphate buffered saline (PBS) supplemented with 10 mM HEPES, 5 mM theophylline, 2 μg/ml aprotinin, 0.5 mg/ml leupeptin, and 10 μg/ml phosphoramidon for 20 min at 37° C., in 5% $CO_2$. Galanin or the test compounds are added and incubated for an additional 10 min at 37° C. The medium is then aspirated and the reaction stopped by the addition of 100 mM HCl. The plates are stored at 4° C. for 15 min, and the cAMP content in the stopping solution measured by radioimmunoassay. Radioactivity may be quantified using a gamma counter equipped with data reduction software.

Arachidonic Acid Release

CHO cells stably transfected with the rat GALR3 receptor are seeded into 96 well plates and grown for 3 days in HAM's F-12 with supplements. $^3$H-arachidonic acid (specific activity=0.75 uCi/ml) is delivered as a 100 uL aliquot to each well and samples were incubated at 37° C., 5% $CO_2$ for 18 hours. The labeled cells are washed three times with 200 uL HAM's F-12. The wells are then filled with medium (200 uL) and the assay is initiated with the addition of peptides or buffer (22 uL). Cells are incubated for 30 min at 37° C., 5% $CO_2$. Supernatants are transferred to a microtiter plate and evaporated to dryness at 75° C. in a vacuum oven. Samples are then dissolved and resuspended in 25 uL distilled water. Scintillant (300 uL) is added to each well and samples are counted for $^3$H in a Trilux plate reader. Data are analyzed using nonlinear regression and statistical techniques available in the GraphPAD Prism package (San Diego, Calif.).

Intracellular Calcium Mobilization

The intracellular free calcium concentration may be measured by microspectroflourometry using the fluorescent indicator dye Fura-2/AM (Bush et al. 1991). Stably transfected cells are seeded onto a 35 mm culture dish containing a glass coverslip insert. Cells are washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Phosphoinositide Metabolism

LM(tk−) cells stably expressing the rat GALR3 receptor cDNA are plated in 96-well plates and grown to confluence. The day before the assay the growth medium is changed to 100 μl of medium containing 1% serum and 0.5 μCi [$^3$H] myo-inositol, and the plates are incubated overnight in a $CO_2$ incubator (5% $CO_2$ at 37° C.) Alternatively, arachidonic acid release may be measured if [$^3$H]arachidonic acid is substituted for the [$^3$H]myoinositol. Immediately before the assay, the medium is removed and replaced by 200 μL of PBS containing 10 mm LiCl, and the cells are equilibrated with the new medium for 20 min. During this interval cells are also equilibrated with the antagonist, added as a 10 μL aliquot of a 20-fold concentrated solution in PBS. The [$^3$H]inositol-phosphates accumulation from inositol phospholipid metabolism may be started by adding 10 $\mu$L of a solution containing the agonist. To the first well 10 $\mu$L may be added to measure basal accumulation, and 11 different concentrations of agonist are assayed in the following 11 wells of each plate row. All assays are performed in duplicate by repeating the same additions in two consecutive plate rows. The plates are incubated in a $CO_2$ incubator for 1 hr. The reaction may be terminated by adding 15 $\mu$l of 50% v/v trichloroacetic acid (TCA), followed by a 40 min. incubation at 4° C. After neutralizing TCA with 40 $\mu$l of 1M Tris, the content of the wells may be transferred to a Multiscreen HV filter plate (Millipore) containing Dowex AG1-X8 (200–400 mesh, formate form). The filter plates are prepared adding 200 AL of Dowex AG1-X8 suspension (50% v/v, water: resin) to each well. The filter plates are placed on a vacuum manifold to wash or elute the resin bed. Each well is washed 2 times with 200 $\mu$L of water, followed by 2×200 $\mu$L of 5 mM sodium tetraborate/60 mM ammonium formate. The [$^3$H]IPs are eluted into empty 96-well plates with 200 $\mu$l of 1.2 M ammonium formate/0.1 formic acid. The content of the wells is added to 3 mL of scintillation cocktail, and the radioactivity is determined by liquid scintillation counting.

GTPγS Functional Assay

Membranes from cells transfected with the GALR3 receptors are suspended in assay buffer (50 mM Tris, 100 mM NaCl, 5 mM $MgCl_2$, pH 7.4) supplemented with 0.1% BSA, 0.1% bacitracin and 10 $\mu$M GDP. Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus GTPγS (final concentration=100 $\mu$M). Final membrane protein concentration≈90 $\mu$g/mL. Samples are incubated in the presence or absence of porcine galanin (final concentration=1 $\mu$M) for 30 min. at room temperature, then filtered on a Millipore vacuum manifold and washed three times with cold assay buffer. Samples collected in the filter plate are treated with scintillant and counted for $^{35}$S in a Trilux (Wallac) liquid scintillation counter. It is expected that optimal results are obtained when the GALR3 receptor membrane preparation is derived from an appropriately engineered heterologous expression system, i.e., an expression system resulting in high levels of expression of the GALR3 receptor and/or expressing G-proteins having high turnover rates (for the exchange of GDP for GTP). GTPγS assays are well-known in the art, and it is expected that variations on the method described above, such as are described by e.g., Tian et al. (1994) or Lazareno and Birdsall (1993), may be used by one of ordinary skill in the art.

The binding and functional assays described herein may also be performed using GALR1 and GALR2 receptors. The GALR1 receptors are well-known in the art and may be prepared and transfected into cells (transiently and stably) using standard methods. Applicants have isolated and cloned the rat and human GALR2 receptors, and have deposited several plasmids expressing GALR2 receptors, as well as cell lines stably expressing the rat GALR2 receptor. Plasmids expressing GALR2 receptors may be transiently or stably transfected into cell using methods well-known in the art, examples of which are provided herein. The rat GALR2 receptor may be expressed using plasmid K985 (ATCC Accession No. 97426, deposited Jan. 24, 1996), or using plasmid K1045 (ATCC Accession No. 97778, deposited Oct. 30, 1996). Plasmid K1045 comprises an intronless construct encoding the rat GALR2 receptor. Cell lines stably expressing the rat GALR2 receptor have also been prepared, for example, the LM(tk−) cell lines L-rGALR2-8 (ATCC Accession No. CRL-12074, deposited Mar. 28, 1996) and L-rGALR2I-4 (ATCC Accession No. CRL-12223, deposited Oct. 30, 1996). L-rGALR2I-4 comprises an intronless construct expressing the rat GALR2 receptor. The CHO cell line C-rGalR2-79 (ATCC Accession No. CRL-12262, deposited Jan. 15, 1997) also stably expresses the rat GALR2 receptor. The human GALR2 receptor may be expressed using plasmid BO29 (ATCC Accession No. 97735, deposited Sep. 25, 1996) or plasmid BO39 (ATCC Accession No. 97851, deposited Jan. 15, 1997). Plasmid BO39 comprises an intronless construct encoding the human GALR2 receptor.

The plasmids and cell lines described above were deposited with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure.

It is to be understood that the cell lines described herein are merely illustrative of the methods used to evaluate the binding and function of the galanin receptors of the present invention, and that other suitable cells may be used in the assays described herein.

Methods for Recording Currents in Xenopus Oocytes

Female *Xenopus laevis* (Xenopus-1, Ann Arbor, Mich.) are anesthetized in 0.2% tricain (3-aminobenzoic acid ethyl ester, Sigma Chemical Corp.) and a portion of ovary is removed using aseptic technique (Quick and Lester, 1994). Oocytes are defolliculated using 2 mg/ml collagenase (Worthington Biochemical Corp., Freehold, N.J.) in a solution containing 87.5 mM NaCl, 2 mM KCl, 2 MM $MgCl_2$ and 5 mM HEPES, pH 7.5. Oocytes are injected (Nanoject, Drummond Scientific, Broomall, Pa.) with 50 nL of rat GalR3 mRNA. Other oocytes are injected with a mixture of GalR3 mRNA and mRNA encoding the genes for G-protein-activated inward rectifiers (GIRK1 and GIRK4). Genes encoding GIRK1 and GIRK4 are obtained using conventional PCR-based cloning techniques based on published sequences (Kubo et al., 1993; Dascal et al., 1993; Krapivinsky et al., 1995). RNAs are prepared from separate DNA plasmids containing the complete coding regions of GalR3, GIRK1 and GIRK4. Plasmids are linearized and transcribed using the T7 polymerase ("Message Machine", Ambion). Alternatively, mRNA may be translated from a template generated by PCR, incorporating a T7 promoter and a poly A tail. After injection of mRNA, oocytes are incubated at 160 on a rotating platform for 3–8 days. Dual electrode voltage clamp ("GeneClamp", Axon Instruments Inc., Foster City, Calif.) is performed using 3 M KCl-filled glass microelectrodes having resistances of 1–3 Mohms. Unless otherwise specified, oocytes are voltage clamped at a holding potential of −80 mV. During recordings, oocytes are bathed in continuously flowing (2–5 ml/min) medium containing 96 mM NaCl, 2 mM KCl, 2 mM $CaCl_2$, 2 mM $MgCl_2$, and 5 mM HEPES, pH 7.5 ("ND96"), or, in the case of oocytes expressing GIRK1 and GIRK4, elevated $K^+$ containing 96 mM KCl, 2 mM NaCl, 2 mM $CaCl_2$, 2 mM $MgCl_2$, and 5 mM HEPES, pH 7.5 ("hK"). Drugs are applied by switching from a series of gravity fed perfusion lines.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying 1 $\mu$M galanin in ND96 solution to oocytes previously injected with mRNA for the GalR3 receptor and observing inward currents at a holding potential of −80 mV. The appearance of currents that reverse at −25 mV and display other properties of the $Ca^{++}$-activated Cl− channel is indicative of GalR3 receptor-activation of PLC and release of IP3 and intracellular $Ca^{++}$. Subsequently, measurement of inwardly rectifying $K^+$ channel (GIRK) activity is monitored in oocytes that have been co-injected with mRNAs encoding GALR3, GTRK1 and GIRK4. These two GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing GalR3 plus the two GIRK subunits are tested for galanin responsivity using 1 μM galanin and measuring $K^+$ currents in elevated $K^+$ solution (hK). Activation of inwardly rectifying currents that are sensitive to 300 μM $Ba^{++}$ signifies GALR3 coupling to a $G_i$ or $G_o$ pathway in the oocytes.

Oocytes were isolated as described above, except that 3 mg/mL collagenase was used to defolliculate the oocytes. Genes encoding G-protein inwardly rectifying $K^+$ channels 1 and 4 (GIRK1 and GIRK4) were obtained by PCR using the published sequences (Kubo et al., 1993; Dascal et al., 1993; Krapivinsky et al., 1995b) to derive appropriate 5' and 3' primers. Human heart cDNA was used as template together with the primers 5'-CGCGGATCCATTATGTCTGCACTCCGAAGGAAATTTG-3' (SEQ ID NO: 54) and 5'-CGCGAATTCTTATGTGAAGCGATCAGAGTTCATTTTTC -3' (SEQ ID NO: 55) for GIRK1 and 5'-GCGGGATCCGCTATGGCTGGTGATTCTAGGAATG-3' (SEQ ID NO: 56) and 5'-CCGGAATTCCCCTCACACCGAGCCCCTGG-3' (SEQ ID NO: 57) for GIRK4.

In each primer pair, the upstream primer contained a BamHI site and the downstream primer contained an EcoRI site to facilitate cloning of the PCR product into pcDNA1-Amp (Invitrogen). The transcription template for hGalR3 was obtained similarly by PCR using the cloned cDNA in combination with primers 5'-CCAAGCTTCTAATACGACTCACTATAGGGCCACCATGGCTGATGCCCAGA-3' (SEQ ID NO: 58) and 5'-TTTTTTTTTTTTTTTTTTTTTTTTTTTTTTTTTTTTGCAGGGTTTATTCCGGTCCTCG-3' (SEQ ID NO: 59).

Alternatively, the complete coding region of hGalR3 is subcloned into the high-efficiency transcription vector pBS $KS^+$ AMV-pA50 (Nowak et al., 1995). This plasmid was modified by adding the recognition sequence for the restriction enzyme SrfI downstream of the poly A sequence in the plasmid. The new plasmid was designated M52. Subcloning involved the isolation of a 1.1 kb NcoI/EcoRI restriction fragment encoding the entire hGALR3 gene followed by its ligation into NcoI/EcoRI digested M52. After identification of a suitable clone (M54), the transcription template was produced by linearization of the plasmid DNA with SrfI. The plasmid M54 was deposited on Sep. 30, 1997, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 209312. mRNAs were transcribed using the T7 polymerase ("Message Machine", Ambion). Each oocyte received 2 ng each of GIRK1 and GIRK4 mRNA in combination with 25 ng of GalR3 mRNA. In other experiments oocytes received injections of mRNAs encoding the human α1A adrenergic receptor, rGalR1 or rGalR2 galanin receptors (Forray et al., 1994; Parker et al., 1995) with or without GIRKs 1 and 4. After injection of mRNAs, oocytes were incubated at 17° for 3–8 days.

Dual electrode voltage clamp ("GeneClamp", Axon Instruments Inc., Foster City, Calif.) was performed as described above, with the following modifications: during recordings, oocytes were bathed in continuously flowing (1–3 mL/min) ND96 medium or, in the case of oocytes expressing GIRKs 1 and 4, elevated $K^+$ containing 48 mM KCl, 49 mM NaCl, 2 mM $CaCl_2$, 2 mM $MgCl_2$, and 5 mM HEPES, pH 7.5 (½ hK). Drugs were applied either by local perfusion from a 10 μl glass capillary tube fixed at a distance of 0.5 mm from the oocyte, or for calculation of steady-state $EC_{50}$s, by switching from a series of gravity fed perfusion lines. Experiments were carried out at room temperature. All values are expressed as mean±standard error of the mean.

MAP Kinase

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (Gq and G11) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the mitogen and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Briefly, cells are stimulated with the mitogen and a soluble extract is prepared. The extract is incubated at 30° C. for 10 min with gamma-32-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatrography paper is washed and counted for $^{32}P$ in a liquid scintillation counter. Alternatively, the cell extract is incubated with gamma-32-ATP, an ATP regenerating system, and biotinylated myelin basic protein bound by streptavidin to a filter support. The myelin basic protein is a substrate for activated MAP kinase. The phosphorylation reaction is carrried out for 10 min at 30° C. The extract can then by aspirated through the filter, which retains the phosphorylated myelin basic protein. The filter is washed and counted for $^{32}P$ by liquid scintillation counting.

Cell Proliferation Assay

Receptor activation of a G protein coupled receptor may lead to a mitogenic or proliferative response which can be monitored via $^{3}H$-thymidine uptake. When cultured cells are incubated with $^{3}H$-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^{3}H$-thymidine at specific activities ranging from 1 to 10 uCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^{3}H$ by liquid scintillation counting. Alternatively, adherant cells are fixed in MeOH or TCA, washed in water, and solubilized in 0.05% deoxycholate/0.1 N NaOH. The soluble extract is transferred to scintillation vials and counted for $^{3}H$ by liquid scintillation counting.

Tissue Preparation for Neuroanatomical Studies

Male Sprague-Dawley rats (Charles River, Wilmington, Mass.) are decapitated and the brains rapidly removed and frozen in isopentane. Coronal sections may be cut at 11 $\mu$m on a cryostat and thaw-mounted onto poly-L-lysine coated slides and stored at −80° C. until use. Prior to hybridization, tissues are fixed in 4% paraformaldehyde, treated with 5 mM dithiothreitol, acetylated in 0.1 M triethanolamine containing 0.25% acetic anhydride, delipidated with chloroform, and dehydrated in graded ethanols.

Probes

Oligonucleotide probes employed to characterize the distribution of the rat GALR3 receptor mRNA may be synthesized, for example, on a Millipore Expedite 8909 Nucleic Acid Synthesis System. The probes are then lyophilized, reconstituted in sterile water, and purified on a 12% polyacrylamide denaturing gel. The purified probes are again reconstituted to a concentration of 100 ng/$\mu$L, and stored at −20° C. Probe sequences may include DNA or RNA which is complementary to the mRNA which encodes the GALR3 receptor.

In Situ Hybridization

Probes are 3'-end labeled with $^{35}S$-dATP (1200 Ci/mmol, New England Nuclear, Boston, Mass.) to a specific activity of about $10^{9}$ dpm/$\mu$g using terminal deoxynucleotidyl transferase (Pharmacia). The radiolabeled probes are purified on Biospin 6 chromatography columns (Bio-Rad; Richmond, CA), and diluted in hybridization buffer to a concentration of $1.5\times10^{4}$ cpm/$\mu$L. The hybridization buffer consists of 50% formamide, 4×sodium citrate buffer (1×SSC=0.15 M NaCl and 0.015 M sodium citrate), 1×Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate. About one hundred $\mu$L of the diluted radiolabeled probe is applied to each section, which is then covered with a Parafilm coverslip. Hybridization is carried out overnight in humid chambers at 40 to 55° C. The following day the sections are washed in two changes of 2×SSC for one hour at room temperature, in 2×SSC for 30 min at 50–60° C., and finally in 0.1×SSC for 30 min at room temperature. Tissues are dehydrated in graded ethanols and apposed to Kodak XAR-5 film for 3 days to 3 weeks at −20° C., then dipped in Kodak NTB3 autoradiography emulsion diluted 1:1 with 0.2% glycerol water. After exposure at 4° C. for 2 to 8 weeks, the slides are developed in Kodak D-19 developer, fixed, and counterstained with cresyl violet.

Solution Hybridization/ribonuclease Protection Assay

For solution hybridization 2–15 $\mu$g of total RNA isolated from tissues may be used. Sense RNA synthesized using the full-length coding sequence of the rGalR2 is used to characterize specific hybridization. Negative controls may consist of 30 $\mu$g transfer RNA (tRNA) or no tissue blanks. Samples are placed in 1.5-ml microfuge tubes and vacuum dried. Hybridization buffer (40 $\mu$l of 400 mM NaCl, 20 mM Tris, pH 6.4, 2 mM EDTA, in 80% formamide) containing 0.25–1.0×10 counts of each probe is added to each tube. Samples are heated at 90° C. for 15 min, after which the temperature is lowered to 45° C. for hybridization.

After hybridization for 14–18 hr, the RNA/probe mixtures are digested with RNAse A (Sigma) and RNAse T1 (Bethesda Research Labs, Gaithersburg, Md.). A mixture of 2.0 ug RNAse A and 1000 units of RNAse T1 in a buffer containing 330 mM NaCl, 10 mM Tris (pH 8.0) and 5 mM EDTA (400 $\mu$l) is added to each sample and incubated for 90 min at room temperature. After digestion with RNAses, 20 $\mu$l of 10% SDS and 50 $\mu$g proteinase K are added to each tube and incubated at 37° C. for 15 min. Samples are then extracted with phenol/chloroform:isoamyl alcohol and precipitated in 2 volumes of ethanol for 1 hr at −70° C. tRNA is added to each tube (30 mg) as a carrier to facilitate precipitation. Following precipitation, samples are centrifuged, washed with cold 70% ethanol, and vacuum dried. Samples are dissolved in formamide loading buffer and size-fractionated on a urea/acrylamide sequencing gel (7.6 M urea, 6% acrylamide in Tris-borate-EDTA). Gels are dried and apposed to Kodak XAR-5 x-ray film.

Development of probes: Using full length cDNA encoding the rat Gal R3 receptor as a template, PCR was used to amplify a 455 base pair fragment corresponding to nucleotides 1061–1516 of the coding sequence. Primers used in PCR contained both sp6 and T7 RNA polymerase promoter sequences, and the PCR generated fragments were subcloned into a plasmid vector (pUC-18). This construct was linearized with Bam HI or Hind III. sp6 and T7 RNA polymerases were used to synthesize the sense and antisense strands of RNA respectively. Full length RNA transcripts were obtained using a full length cDNA construct in pBluescript.

A probe coding for rat glyceraldehyde 3-phosphate dehydrogenase (GAPDH) gene, a constitutively expressed protein, is used concurrently. GAPDH is expressed at a relatively constant level in most tissue and its detection is used to compare expression levels of the rat GalR3 gene in different tissue.

Extraction of RNA: Tissue harvested from rat peripheral tissue as well as regions of the CNS was frozen using liquid $N_2$ and stored at −70° C. until needed Tissue was homogenized in buffer containing detergent, protein and RNase degrader. The homogenate was incubated with Oligo(dT) cellulose powder, and washed extensively. mRNA was eluted from the Oligo(dT) cellulose with 10 mM Tris, and precipitated after the addition of NaCl. Yield and relative purity were assessed by measuring absorbance $A_{260}/A_{280}$.

Synthesis of probes: rGALR3 and GAPDH cDNA sequences preceded by phage polymerase promoter sequences were used to synthesize radiolabeled riboprobes. Conditions for the synthesis of riboprobes were: 0.5–1.0 $\mu$L linearized template (1 $\mu$g/$\mu$L), 1.5 $\mu$L of ATP, GTP, UTP (10 mM each), 3 $\mu$L dithiothreitol (0.1 M), 30 units RNAsin RNAse inhibitor, 0.5–1.0 $\mu$L (15–20 units/$\mu$L) RNA polymerase, 7.0 $\mu$L transcription buffer (Promega Corp.), and 12.5 $\mu$L a$^{32}$P-CTP (specific activity 3,00 Ci/mmol). 0.1 mM CTP (0.02–1.0 $\mu$L) were added to the reactions, and the volume were adjusted to 35 μL with DEPC-treated water. Labeling reactions were incubated at 37° C. for 90 min, after which 3 units of RQ1 RNAse-free DNAse (Promega Corp.) were added to digest the template. The riboprobes were separated from unincorporated nucleotide by a spun G-50 column (Select D G-50(RF); 5 Prime-3 Prime, Inc.). TCA precipitation and liquid scintillation spectrometry were used to measure the amount of label incorporated into the probe. A fraction of all riboprobes synthesized were size-fractionated on 0.4 mm thick 5% acrylamide sequencing gels and autoradiographed to confirm that the probes synthesized were full-length and not degraded.

Solution hybridization/ribonuclease protection assay: For solution hybridization 2.0 μg of total RNA isolated from tissues were used. Sense RNA synthesized using the full-length coding sequence of the rGalR3 was used to characterize specific hybridization. Negative controls consisted of 30 μg transfer RNA (tRNA) or no tissue blanks. All mRNA samples were placed in 1.5-ml microfuge tubes and vacuum dried. Hybridization buffer (40 μl of 400 mM NaCl, 20 mM Tris, pH 6.4, 2 mM EDTA, in 80% formamide) containing 0.25–1.0×$10^6$ counts of each probe were added to each tube. Samples were heated at 90° C. for 15 min, after which the temperature was lowered to 42° C. for hybridization.

After hybridization for 14–18 hr, the RNA/probe mixtures were digested with RNAse A (Sigma) and RNAse T1(Life Technologies). A mixture of 2.0 μg RNAse A and 1000 units of RNAse T1 in a buffer containing 330 mM NaCl, 10 mM Tris (pH B.0) and 5 mM EDTA (400 μL) was added to each sample and incubated for 90 min at room temperature. After digestion with RNAses, 20 μL of 10% SDS and 50 Hg proteinase K were added to each tube and incubated at 37° C. for 15 min. Samples were then extracted with phenol/chloroform:isoamyl alcohol and precipitated in 2 volumes of ethanol for 1 hr at −70° C. Pellet Paint (Novagen) was added to each tube (2.0 μg) as a carrier to facilitate precipitation. Following precipitation, samples were centrifuged, washed with cold 70% ethanol, and vacuum dried. Samples were dissolved in formamide loading buffer and size-fractionated on a urea/acrylamide sequencing gel (7.6 M urea, 6% acrylamide in Tris-borate-EDTA). Gels were dried and apposed to Kodak XAR-5 x-ray or BioMax film and exposed at −70° C.

In vivo Methods

The effects of galanin, galanin derivatives, and related peptides and compounds may be evaluated by intracerebroventricular (i.c.v.) injection of the peptide or compound followed by measurement of food intake in the animal. Measurement of food intake was performed for 3 hours after injection, but other protocols may also be used. Saline was injected as a control, but it is understood that other vehicles may be required as controls for some peptides and compounds. In order to determine whether a compound is a GALR3 antagonist, food intake in rats may be stimulated by administration of (for example) a galanin receptor agonist through an intracerebroventricular (i.c.v.) cannula. A preferred anatomic location for injection is the hypothalamus, in particular, the paraventricular nucleus. Methods of cannulation and food intake measurements are well-known in the art, as are i.c.v. modes of administration (Kyrkouli et al., 1990, Ogren et al., 1992). To determine whether a compound reduces agonist-stimulated food intake, the compound may be administered either simultaneously with the peptide, or separately, either through cannula, or by subcutaneous, intramuscular, or intraperitoneal injection, or more preferably, orally.

Materials

Cell culture media and supplements are from Specialty Media (Lavallette, N.J.). Cell culture plates (150 mm and 96-well microtiter) are from Corning (Corning, N.Y.). Sf9, Sf21, and High Five insect cells, as well as the baculovirus transfer plasmid, pBlueBacIII™, are purchased from Invitrogen (San Diego, Calif.). TMN-FH insect medium complemented with 10% fetal calf serum, and the baculovirus DNA, BaculoGold™, is obtained from Pharmingen (San Diego, Calif.). Ex-Cell 400™ medium with L-Glutamine is purchased from JRH Scientific. Polypropylene 96-well microtiter plates are from Co-star (Cambridge, Mass.). All radioligands are from New England Nuclear (Boston, Mass.).

Galanin and related peptide analogs were either from Bachem California (Torrance, Calif.), Peninsula (Belmont, Calif.); or were synthesized by custom order from Chiron Mimotopes Peptide Systems (San Diego, Calif.).

Bio-Rad Reagent was from Bio-Rad (Hercules, Calif.). Bovine serum albumin (ultra-fat free, A-7511) was from Sigma (St. Louis. Mo.). All other materials were reagent grade.

Experimental Results

Isolation of a Partial GALR3 cDNA From Rat Hypothalamus

In order to clone additional members of the galanin receptor family, a homology cloning strategy based on the potential presence of multiple galanin receptors in hypothalamus was designed. Although recent evidence indicated that GALR1 and GALR2 receptor mRNAs were present in rat hypothalamus (Gustafson et al., 1996; Parker et al., 1995), not all aspects of the cloned GALR1 and GALR2 pharmacological profiles match that observed for galanin-mediated feeding (Crawley et al., 1993). These results suggested that the regulation of galanin-induced feeding may not be explained by the presence of only GALR1 or GALR2 (or both) in the rat hypothalamus.

In order to attempt to isolate additional galanin receptors, a rat hypothalamus cDNA phage library was screened, under reduced stringency conditions, with oligonucleotide probes directed to the transmembrane regions of the rat GALR2 neuropeptide receptor gene. Five positively-hybridizing clones were isolated, plaque-purified and characterized by Southern blot analysis and sequencing. One clone, rHY35a, contained a 3.5 kb insert (consisting of a 1.0 kb, 0.2 kb, and 2.3 kb EcoRI fragments), which hybridized with the second transmembrane domain oligonucleotide probe of rat GALR2. DNA sequence analysis indicated greatest homology to the published rat GALR1 gene (Burgevin, et al., 1995) and the novel rat GALR2 receptor gene we have recently identified. This clone was a partial intronless gene fragment, containing an open reading frame and encoding a predicted starting MET through the middle of the predicted seventh transmembrane domain, with ≈150 nucleotides of 5' UT. Hydropathy analysis of the predicted translated protein is consistent with a putative topography of at least six transmembrane domains (the predicted sequence ended in the middle of TM7), indicative of the G protein-coupled receptor family. This gene fragment exhibited 52% and 66% nucleotide identity and 37% and 60% amino acid identity to the rat GALR1 and rat GALR2 receptors, respectively. Furthermore, PCR primers directed to the amino terminus (forward primer) and first extracellular loop (reverse primer) of each of the corresponding receptor genes, rGALR1 and rGALR2, were unable to amplify this clone, whereas primers directed to this clone resulted in the correct size PCR product. The putative six (or seven) transmembrane topography and the high degree of identity to rat GALR1 and GALR2 suggested that this cDNA represented a partial gene fragment of a novel galanin-like receptor gene, referred to herein as GALR3.

In order to obtain the full-length gene, PCR on cDNA derived from the RIN14B cell line, using internal primers directed to TM3 and third intracellular loop of rat GALR3 was first conducted. It was hypothesized that since previous data indicated that this cell line expressed both GALR1 and GALR2, it may also contain further subtypes. PCR analyses revealed the presence of at least a portion of GALR3 in cDNA from RIN14B cells; the absence of reverse transcriptase did not result in PCR amplification, indicating the ability to amplify RIN14B cDNA was due to authentic GALR3 mRNA and not any contaminating genomic DNA in the RNA source.

To isolate a cDNA molecule from RIN14B which expresses GALR3, a RIN14B plasmid library was screened by PCR (using internal primers) and two pools, F105 and F212, were identified which contained a PCR product of the correct size. To determine if the insert was in the correct orientation for expression and to determine the size of the cDNA insert (including the coding region, 5'UT and 3 'UT), vecror-anchored PCR was conducted on each pool. The PCR analyses suggested that both pools contained full-length GALR3 but in the incorrect orientation and thus would be predicted not to express the GALR3 receptor. Examination of slides of COS-7 cells which had been transfected with DNA from each of these pools and subsequently bound with radioligand confirmed the absence of binding of radiolabeled galanin, presumably due to its incorrect orientation.

Although the full-length clone of rat GALR3 in the correct orientation from the RIN14Bplasmid library was not obtained, it was reasoned that the sequence of the missing 3' end (i.e., from the middle of TM7 through the stop codon) could be obtained by sequencing the vector-anchored PCR product corresponding to the 3' end of the molecule. An ≈1.2 kb PCR product from a vector-anchored amplification of bacterial glycerol stock of the F105 pool was obtained, using a vector-derived reverse primer and a rGALR3-specific forward primer from TM6. This PCR product was sequenced with the gene-specific primer to reveal an overlap within TM7 with the sequence known from rHY35a. In addition, further sequence was obtained representing an open reading frame corresponding to the missing second half of TM7 and the carboxy terminus. The sequence obtained showed an overall 47% nucleotide identity to rGalR2, and a 62% nucleotide identity to rGalR2 from the third extracellular domain to the 5' end of the COOH terminus, confirming the existence of an open reading frame from a starting MET throuyh a stop codon, with the presence of seven putative transmembrane domains. Furthermore, this sequence permitted us to design an oligonucleotide primer in n the 3' UT which Could serve as a diagnostic tool for determination of full-length characterization of additional pools of DNA (see below).

Since the most convenient method to obtain the full-length rGALR3 clone in the correct orientation in an expression vector is to locate a full-length clone in preexisting libraries, and it was known that this gene was expressed in rat hypothalamus, we screened a rat hypothalamus plasmid library ("K") by PCR. Two superpools from the K library (#3 and #17) were identified as containing rGALR3. A primary pool, K163 (from superpool #17), was identified to be positive and full-length using internal and full-length PCR primers, and vector-anchor primers were used to determine the orientation. These data were consistent with primary pool K163 (made up of 3200 primary clones), containing full-length rGALR3 in the correct orientation in the expression vector, pEXJ.T7. Furthermore, this pool failed to amplify with GALR1- and GALR2-specific primers and yet exhibited galanin binding when DNA from this pool was used to transfect COS cells and tested for radiolabeled galanin binding. These data suggested that a pool from a rat hypothalamus plasmid cDNA library which contains the novel sequence initially identified from rat hypothalamus as a galanin-like receptor had been identified, which, in addition, exhibits galanin binding, thereby identifying the pool as containing a novel galanin receptor, referred to herein as GALR3, or more specifically, rGALR3.

The pool K163 was then sib selected through one round by PCR and a second round by colony hybridization, using a probe directed to the amino terminus of the sequence from rHY35a, resulting in the isolation of a single clone (i.e., a bacterial colony containing rat GALR3), called K163-30-17, representing the full-length rat GALR3 in the correct orientation. The rGALR3 recombinant bacterial colony was grown up in broth with ampicillin and DNA extracted. Restriction enzyme digestion suggested a 2.1 kb insert, consistent with the clone comprising the full-length coding region.

Furthermore, sequence analysis on K163-30-17 DNA (plasmid K1086) confirmed that it contained a full-length coding region in the correct orientation for expression.

Northern Blot Analyses of GALR3 mRNA

To define the size and distribution of the mRNA encoding GALR3, Northern blot analyses of poly $A^+$ RNA from various rat tissues and brain regions was carried out. A radiolabeled 70-mer oligonucleotide probe directed to the amino terminus of the rat GALR3 coding region was used as a hybridization probe under high stringency. This probe failed to cross-hybridize with either the GALR1 or GALR2 genes under similar hybrization conditions, demonstrating its specificity for GALR3 receptor. A single transcript of ≈3.3 kb is detected after a 5 day exposure of the autoradiogram at −80° C. using Kodak Biomax MS film with a Biomax MS intensifying screen. GALR3 mRNA was not detected by Northern analysis in the brain nor in various regions of the brain (see Table 1). Among various rat tissues, the GALR3 transcript had a restricted distribution; GALR3 mRNA was predominantly observed in kidney with a faint signal detected in liver (see Table 1). This distribution was the same upon a longer exposure of the autoradiogram (14 days). Northern blots were reprobed with G3PDH probe to assess whether similar amounts of mRNA were present in each lane.

Northern blot analyses of poly A+ RNA from various human brain regions and peripheral tissues were carried out with a radiolabeled 70-mer oligonucleotide probe directed to the amino terminus of the human GALR3 coding region under high stringency. A s demonstrated for the corresponding rat probe, this human probe failed to cross-hybridize with either the human GALR1 or GALR2 genes under similar hybridization conditions, demonstrating its specificity for human GALR3 receptor. No transcript was observed even after 14 day exposure of the autoradiogram in any of the human n brain regions or peripheral tissues, by Northern blot analyses. The regions of the brain and periphery included in this analysis, as contained in the MTN blots from Clontech, included: amygdala, caudate nucleus, corpus callosum, hippocampus, total brain, substantia nigra, subthalamic brain, thalamus nucleus, cerebellum,cerebral cortex, medulla, spinal cord, occipital pole, frontal lobe, temporal lobe, putamen, heart, total brain, placenta, lung, liver, skeletal muscle, kidney, and pancreas.

Reverse-transcription PCR of GALR3 mRNA

Amplification of cDNA derived from mRNA of various rat peripheral and brain regions demonstrated the presence of GALR3 mRNA in various regions of the brain, including hypothalamus (see Table 2), as well as several peripheral tissues tested, such as pancreas and liver. It was anticipated that we would identify GALR3 mRNA in hypothalamus since the gene was cloned from this region of the brain (supra). Therapeutic indications implied from localization of GALR3 mRNA for several of these regions are also indicated in Table 2.

TABLE 1

Northern blot analyses of GALR3 mRNA in brain and various peripheral rat tissues

| Tissue | Intensity of Signal | Therapeutic Indications |
|---|---|---|
| Heart | (–) | |
| Brain | (–) | |
| Spleen | (–) | |
| Lung | (–) | |
| Liver | + | Diabetes |
| Skeletal Muscle | (–) | |
| Kidney | ++ | Hypertension, electrolyte balance, diuretic, anti-diuretic |
| Testis | (–) | |
| Spinal cord | (–) | |
| Periaqueductal Grey | (–) | |
| Cerebellum | (–) | |
| Cortex | (–) | |
| Brain Stem | (–) | |
| Hypothalamus | (–) | |
| Amygdala | (–) | |
| RIN14B cell line | (–) | |

TABLE 2

RT-PCR analyses of GALR3 mRNA in brain and various peripheral rat tissues.

| Tissue | Intensity of Signal | Therapeutic Indications |
|---|---|---|
| Heart | (–) | |
| Brain | + | Obesity/feeding, analgesia, cognition enhancement, Alzheimer's disease, depression, anxiety, sleep disorders, Parkinson's disease, traumatic brian injury, convulsion/epilepsy |
| Spleen | + | Immune functions, hematopoiesis |
| Lung | + | Respiratory disorders, asthma, emphysema, lung cancer diagnostics |
| Liver | + | Diabetes |
| Skeletal Muscle | (–) | Diabetes |
| Smooth Muscle | + | |
| Kidney | + | Hypertension, electrolyte balance, diuretic, anti-diuretic |
| Pancreas | +++ | Appetite/obesity, diabetes, gastrointestinal disorders, neuroendocrine regulation |
| Retina | (–) | |
| Testis | + | Reproductive function |
| Ventral spinal cord | ++ | Analgesia |

TABLE 2-continued

RT-PCR analyses of GALR3 mRNA in brain and various peripheral rat tissues.

| Tissue | Intensity of Signal | Therapeutic Indications |
|---|---|---|
| Dorsal spinal cord | ++ | Analgesia |
| Periaqueductal Grey | (–) | |
| Cerebellum | + | Motor disorders |
| Cortex | (–) | |
| Brain Stem | + | Autonomic disorders |
| Lower midbrain | + | |
| Hypothalamus | ++ | Neuroendocrine regulation, appetite/obesity |
| Amygdala | (–) | |
| RIN14B cell line | + | Neuroendocrine regulation, including diabetes |

RNase Protection Assay to Detect mRNA Coding for Rat GALR3 mRNA was isolated and assayed as described from: heart, striated muscle, liver, kidney, lung, stomach, spleen, pancreas, pituitary, adrenal medulla, adrenal cortex, trigeminal ganglion and CNS regions. CNS regions included: whole brain, spinal cord, medulla, hypothalamus, cerebral cortex, cerebellum, hippocampus, caudate-putamen, and substantia nigra. Levels of rat GALR3 mRNA were extremely low in all areas assayed. The highest levels of rat GALR3 mRNA were detected in the hypothalamus. Lower amounts were found in: kidney, liver, stomach, pancreas, spleen, pituitary, adrenal medulla, adrenal cortex, whole brain, spinal cord, medulla, cerebellum and caudate/putamen. At the present time, mRNA coding for the rat GALR3 has not been detected in RNA extracted from other regions (Table 3).

TABLE 3

Distribution of mRNA coding for rat GALR3 receptors.

| Region | rGalR3 | Potential applications |
|---|---|---|
| liver | + | Diabetes |
| kidney | + | Hypertension, Electrolyte balance |
| lung | + | Respiratory disorders, asthma |
| heart | – | Cardiovascular indications |
| stomach | + | Gastrointestinal disorders |
| duodenum | – | Gastrointestinal disorders |
| spleen | + | Immune function |
| pancreas | + | Diabetes, endocrine disorders |
| testicle | – | Reproductive function |
| striated muscle | – | Musculoskeletal disorders, diabetes |
| pituitary | + | Endocrine/neuroendocrine regulation |
| adrenal medulla | + | Regulation of epinephrine release |
| adrenal cortex | + | Regulation of steroid hormones |
| trigeminal ganglion | – | Analgesia, sensory transmission, migraine |
| whole brain | + | |
| cerebral cortex | + | Sensory integration, cognition |
| hypothalamus | ++ | Appetite/obesity, Neuroendocrine regulation |
| hippocampus | – | Cognition/memory |
| spinal cord | ++ | Analgesia, sensory modulation and transmission |

TABLE 3-continued

| Distribution of mRNA coding for rat GALR3 receptors. | | |
|---|---|---|
| Region | rGalR3 | Potential applications |
| cerebellum | + | Motor coordination |
| medulla | + | Analgesia, motor coordination |
| substantia nigra | − | Modulation of dopaminergic function. Modulation of motor coordiantion. |
| caudate-putamen | + | Modulation of dopaminergic function |

Pharmacological Characterization of GALR3

The pharmacology of GALR3 was studied in COS-7 cells transiently transfected with the GALR3 cDNA, K163-30-17 (or "K1086"). COS-7 cells transfected with the single clone K1086 exhibit specific binding of $^{125}$I-galanin in comparison with COS-7 cells transfected with control vector. In preliminary radioligand binding experiments, porcine $^{125}$I-galanin bound to membranes from COS-7 cells transfected with K1086, with a specific binding of 90 fmol/mg, when the membranes (0.17 mg/mL) were incubated with 2.1 nM porcine 125I-galanin for 60 min at room temperature. (Specific binding was decreased by as much as 70% when the incubation temperature was raised to 30° C., suggesting receptor instability and/or protease activity in the membrane preparation.) In this experiment, the binding buffer used was that described for the whole cell slide binding assay. No specific binding was detected to membranes from mock-transfected COS-7 cells when tested under the same conditions.

In another experiment, COS-7 cells were transiently transfected with a "trimmed" plasmid (designated pEXJ-RGalR3T), which comprises the entire coding region of rat GALR3, but in which the 5' initiating ATG is joined directly to the vector, and which comprises only 100 nucleotides from the 3' untranslated region, after the stop codon (i.e., up to and including nucleotide 1275 in FIG. 1). A full saturation binding analysis using $^{125}$I-galanin was performed using the COS-7 cells transfected with plasmid pEXJ-RGalR3T, and yielded a $K_d$ (dissociation constant) of 0.34 nM and an apparent $B_{max}$ as high as 570 fmol/mg. The use of the "trimmed" plasmid provides for greater expression and therefore greater convenience and accuracy in binding assays.

Peptide displacement assays yielded a distinct rank order of binding affinity (Table 4). Porcine galanin bound with relatively high affinity ($K_i$=5 nM), C-terminal truncation to porcine galanin 1–16 was disruptive (Ki=86 nM), and galanin 3–29 as well as D-Trp$^2$-galanin analogs were without demonstrable binding. Two chimeric peptides displayed high affinity for GALR3 (M32 and M35) whereas galantide was slightly less active and the putative "antagonists" C7 and M40 were relatively weak ligands.

Peptide binding profiles for the rat GALR1, GALR2 and GALR3 receptor subtypes were derived from membranes prepared from transiently transfected COS-7 cells. Rat GALR3 is distinguished from the other receptor subtypes by having 40-fold lower affinity for M40 vs. galanin, whereas the rat GALR1 and GALR2 receptor subtypes display <=8-fold lower affinity for M40 vs. galanin. Rat GALR3 also displays low affinity for the D-Trp$^2$-galanin analogs, which appear to be primarily useful for distinguishing the rat GALR2 receptor. It is concluded that the rat GALR3 displays a distinctive pharmacological profile which can be used to evaluate receptor expression in native cells and tissues.

TABLE 4

| Peptide binding profile of rat GALR1, GALR2 and GALR3 receptors transiently expressed in COS-7 cell membranes and labeled with porcine $^{125}$I-galanin. Values are reported as $K_i$ (nM). | | | |
|---|---|---|---|
| Peptide | GALR1 ($K_i$, nM) | GALR2 ($K_i$, nM) | GALR3 ($K_i$, nM) |
| porcine galanin | 0.46 | 0.45 | 5.1 |
| M32 | 0.62 | 12 | 2.1 |
| M35 | 0.33 | 0.57 | 6.7 |
| galantide | 9.5 | 2.0 | 18 |
| C7 | 16 | 19 | 68 |
| M40 | 3.6 | 0.72 | 210 |
| porcine galanin 1-16 | 2.2 | 7.2 | 86 |
| D-Trp$^2$-galanin 1-29 | 3700 | 52 | >1000 |
| D-Trp$^2$-galanin 1-16 | 40 000 | 23 | >1000 |
| porcine galanin 3-29 | >100 000 | >100 000 | >1000 |

Isolation of the Human GALR3 Gene

A human placenta genomic library in λ dash II (≈1.5×10$^6$ total recombinants) was screened using the same set of overlapping oligonucleotide probes to TM regions 1–7 of rat GALR2 and under the same hybridization and wash conditions as described for screening the rat hypothalamus cDNA library. Lambda phage clones hybridizing with the probe were plaque purified and DNA was prepared for Southern blot analysis. One phage clone, plc21a, contained a 2.7 kb KpnI/EcoRI fragment which hybridized with the rat GALR2 TM2 oligonucleotide probe and was subsequently subcloned into a pUC vector for sequence analysis. The cloned human genomic fragment contains an a open reading frame from the starting MET codon to a predicted intron in the second intracellular loop, with a nucleotide identity of 88% (93% aa identity) with the rat GALR3 receptor described above (thus establishing this human genomic clone to be the human homologue of rat GALR3). Although this human genomic fragment was not full-length and contained an intron downstream of TM3, it is anticipated that the full-length, intronless version of the human GALR3 receptor gene may be isolated using standard molecular biology techniques, as described in Materials and Methods.

Since the human genomic fragment was not full-length and contained an intron downstream of TM3, it was hypothesized that the original phage clone, which contains an average insert size of about 18 kb, may contain the 3' end of this gene, assuming a smaller size for the intron which separates the 5' and 3' exons. The presence of the exon, representing the 3' end of the human GALR3, on the original phage clone, was demonstrated by positive hybridization signals of the phage clone, plc21a, with probes directed to the third extracellular loop or TM4 of the rat GALR3 gene.

The full-length human GALR3 gene was constructed by ligating a PCR-derived product of the 5' exon, representing the starting MET through the ¾ loop with a synthetically-created KpnI site appended to the reverse PCR primer, and the 3' exon, contained on a 1.4 kb KpnI genomic fragment. The full-length human GALR3 gene contains 1107 bp within its coding region, encoding for a predicted protein of 368 aa. The rat homologue contains two additional aa and encodes for a predicted protein of 370 aa. The human and rat GALR3 homologues exhibit 86% nucleotide and 92% amino acid identities, consistent with designating these genes as species homologues of the same gene within the GPCR family. The amino acid identity increases to 96% when restricting the comparison to within the transmembrane domains. The human GALR3 gene exhibits 52% and 67% nucleotide identities and 36% and 58% amino acid identities to the human GALR1 and GALR2 receptors, respectively. Furthermore, within the transmembrane domains, the human GALR3 receptor displays 46% and 74% amino acid identities with the human GALR1 and GALR2 receptors, respectively. This relationship suggests that human GALR3 represents a novel receptor subtype within the galanin gene family.

Pharmacological Characterization of Human GALR3

The pharmacology of human GALR3 was studied in COS-7 cells transiently transfected with pEXJ-hGalR3. In preliminary radioligand binding experiments using membranes prepared from COS-7 cells transfected with pEXJ-hGalR3, specific binding of galanin was observed with binding of 6 fmol/mg when the membranes (0.31 mg/mL) were incubated with 0.32 nM porcine $^{125}$I-galanin for 2 hrs. at room temperature. No mock transfection was performed in this assay because no galanin binding to COS-7 cells was observed previously in binding experiments using similar conditions (supra).

In a subsequent experiment, when membranes from transiently transfected cells (membrane protein=0.15 mg/ml) were incubated with porcine $^{125}$I-galanin (0.32 nM), specific binding was measured as 110 fmol/mg. Therefore, it is concluded that the human GALR3 receptor cDNA leads to expression of functional GALR3 receptors, thereby providing an important tool with which to evaluate ligand selectivity for human GALR1, GALR2 and GALR3 receptor subtypes.

In further experiments, cell lines stably expressing the rat and human GALR3 receptors were prepared. Membranes from the stably transfected cell line 293-rGalR3-105 bound porcine $^{125}$I-galanin with a $K_d$ of 0.74 nM and an apparent $B_{max}$ of 450 fmol/mg membrane protein. Both the transiently and stably expressed rat GALR3 receptors were analyzed in competitive displacement assays using porcine $^{125}$I-galanin (Table 5). Like GALR2, GALR3 appears to bind the N-terminally extended peptide galanin −7 to +29 with affinity comparable to that for porcine galanin. These data provide a pharmacological fingerprint which should be useful for characterizing GALR3-dependent processes in vivo.

Next, the cDNA for the human GALR3 receptor was used to prepare both transiently and stably transfected cells. Membranes from COS-7 cells transiently transfected with human GALR3 cDNA bound porcine $^{125}$I-galanin with a $K_d$ of 1.25 nM and an apparent $B_{max}$ of 750 fmol/mg membrane protein. Membranes LM(tk−) cells stably transfected with human GALR3 receptor CDNA (L-hGalR3-228) bound porcine $^{125}$I-galanin with a $K_d$ of 2.57 nM and an apparent $B_{max}$ of 1700 fmol/mg membrane protein. Specific binding measured in the presence of 0.3 nM porcine $^{125}$I-galanin was reduced by 40% in the presence of nonhydrolyzable guanine nucleotides such as GTPγS or Gpp(NH)p at concentrations up to 100 μM. These data suggest that the human GALR3 receptor interacts with one or more G proteins in the LMTK− cell, and furthermore, that receptor stimulation by galanin might lead to a functional response in the LMTK− cell at the level of the G-protein or further downstream in the signal transduction pathway. Preliminary analyses in peptide displacement assays using porcine $^{125}$I-galanin as the radioligand indicate that the human GALR3 receptor, sharing 92% amino acid identity with the rat GALR3 receptor, binds galanin and related analogs with affinities resembling those for the rat receptor. A similar pharmacological profile for both the human and rat GALR3 receptor homologs suggests that the rat may be used to model the therapeutic value of GALR3-directed ligands. A noteworthy feature of the pharmacology is that the GALR3 receptor, whether human or rat, binds human galanin with lower affinity compared to rat and porcine galanin. Human galanin is also somewhat less potent than porcine galanin in both in vitro functional and in vivo feeding assays. This relationship differentiates the GALR3 receptor from the GALR1 and GALR2 subtypes, and may be useful in further investigations.

TABLE 5

| | Ki (nM) | | | |
|---|---|---|---|---|
| Peptide | Rat GalR3 COS7 | 293-rGalR3-105 | Human GalR3 COS7 | L-hGalR3-228 |
| M32 | 1.9 | 1.0 | | 6.0 |
| M35 | 3.7 | 3.2 | 19 | 7.8 |
| rat galanin | 4.3 | 5.7 | | |
| porcine galanin | 5.1 | 5.8 | 5.3 | 14 |
| human galanin | 10.5 | 53 | 19 | 69 |
| galantide | 9.0 | 7.6 | 23 | 40 |
| C-7 | 23 | 9.6 | | 8.1 |
| M40 | 103 | 85 | | 130 |
| porcine galanin 1-16 | 52 | 138 | 35 300 | 320 |
| D-Trp2-galanin | >1000 | >1000 | | |
| galanin −7 to +29 | 3.3 | 21 | 29 | |

Signal Transduction Pathway of hGalR3: Stimulation of $K^+$ Currents

Heterologous expression of GPCRs in Xenopus oocytes has been widely used to determine the identity of signaling pathways activated by agonist stimulation (Gundersen et al., 1983; Takahashi et al., 1987; Dascal et al., 1993). A large family of GPCRs that naturally couple to heterotrimeric G-proteins of the $G_i/G_o$ class activate GIRK channels (North, 1989) in native neurons (Kofuji et al., 1995) and in the Xenopus expression system (Dascal et al., 1993; Kubo et al., 1993; Krapivinsky et al., 1995). Under voltage clamp conditions, oocytes injected with mRNAs for hGALR3 and GIRKs 1 and 4 responded with inward currents to local perfusion of porcine galanin (FIG. 6A). Average currents were 51.3±9.4 nA (n=16) in the presence of 1 μM porcine galanin, whereas oocytes injected with mRNAs for GIRKs 1 and 4 alone produced little or no inward current (2.5±1.2 nA, n=8) in response to 1 μM galanin. Oocytes injected with mRNA encoding the rat GalR3 receptor also exhibited current responses to the 1 μM local application of M32 or porcine galanin. The pharmacology of the rat GalR3 receptor was not further evaluated in oocytes. In oocytes expressing human GalR3, evidence that galanin-induced currents were mediated by GIRK channels included: 1) dependency on elevated external $K^+$, 2) strong inward rectification of the current-voltage (I/V) relation, 3) reversal potential (−26±2 mV) close to the predicted equilibrium potential for $K^+$ (−23 mV), 4) sensitivity to block by 300 μM $Ba^{++}$ (FIG. 6A), and 5) lack of galanin-sensitivity in oocytes injected with only hGALR3 mRNA (data not shown). Currents having these same properties, but larger in amplitude, were also evoked by galanin in oocytes expressing GALR1 receptors in combination with GIRKs 1 and 4 (Table 6). Thus, GALR1 and GALR3 receptors appear to have a related signal transduction pathway.

Figure 7:
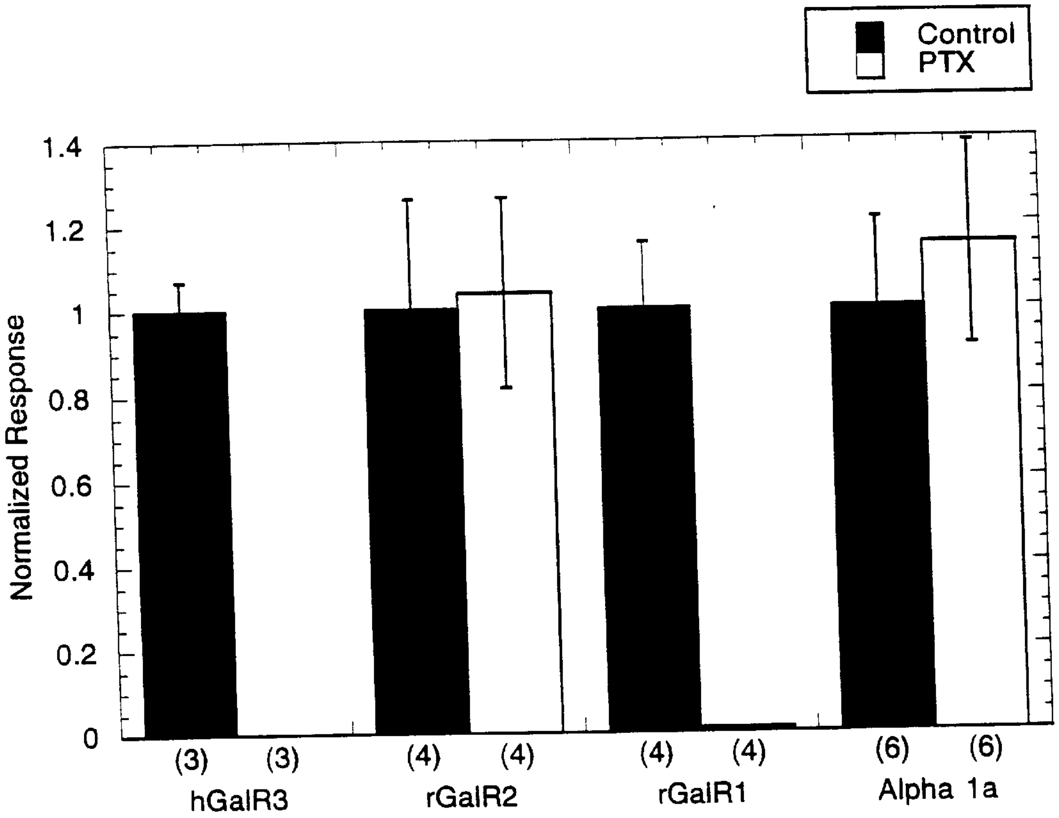
FIG. 7 Pertussis toxin sensitivity of GalR3 and GalR1 stimulation of GIRK currents. Normalized mean currents elicited by 0.1 $\mu$M (GalR1) and 1 AM (GalR3) galanin in oocytes injected 3 h prior with 2 ng of pertussis toxin compared to water-injected oocytes. For oocytes expressing GalR2 and ala receptors, the response amplitude was measured as the peak of the $Cl^-$ current stimulated by 1 $\mu$M galanin or epinephrine, respectively. Number of observations appears in parenthesis below the x-axis. Apparent absence of a bar indicates an amplitude of 0 (no response above baseline).
Figure 8A:
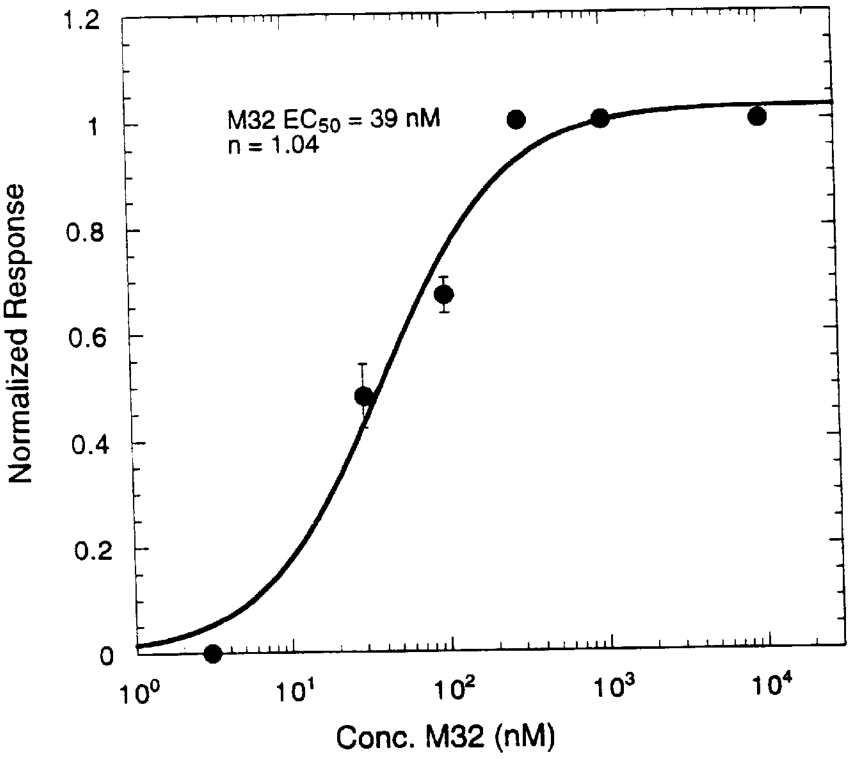
FIGS. 8A–8G Concentration-response relations for 6 peptides at GalR3 receptors expressed in oocytes.
Figure 8B:
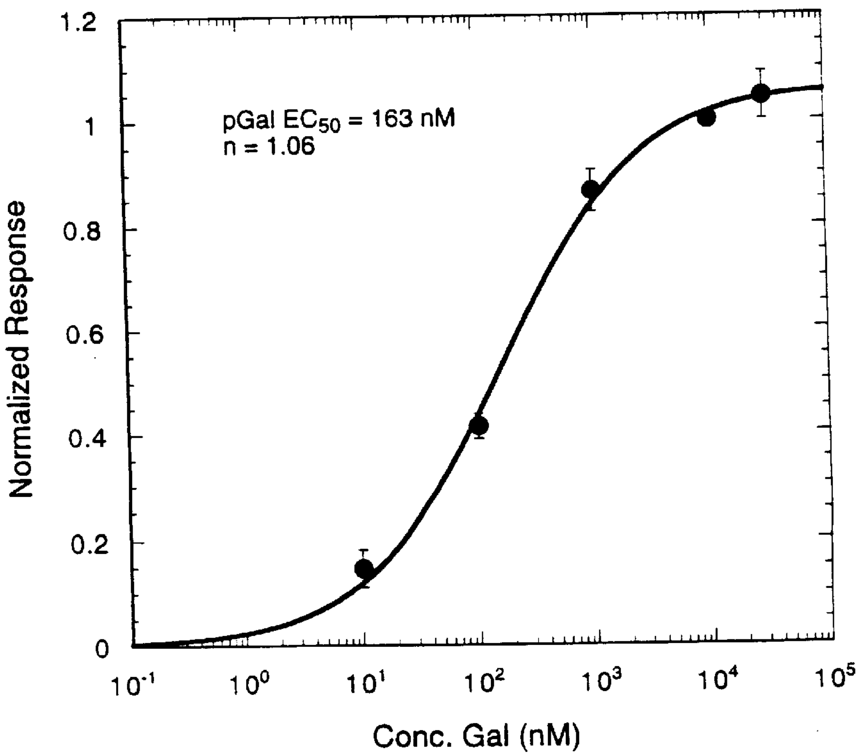
Figure 8C:
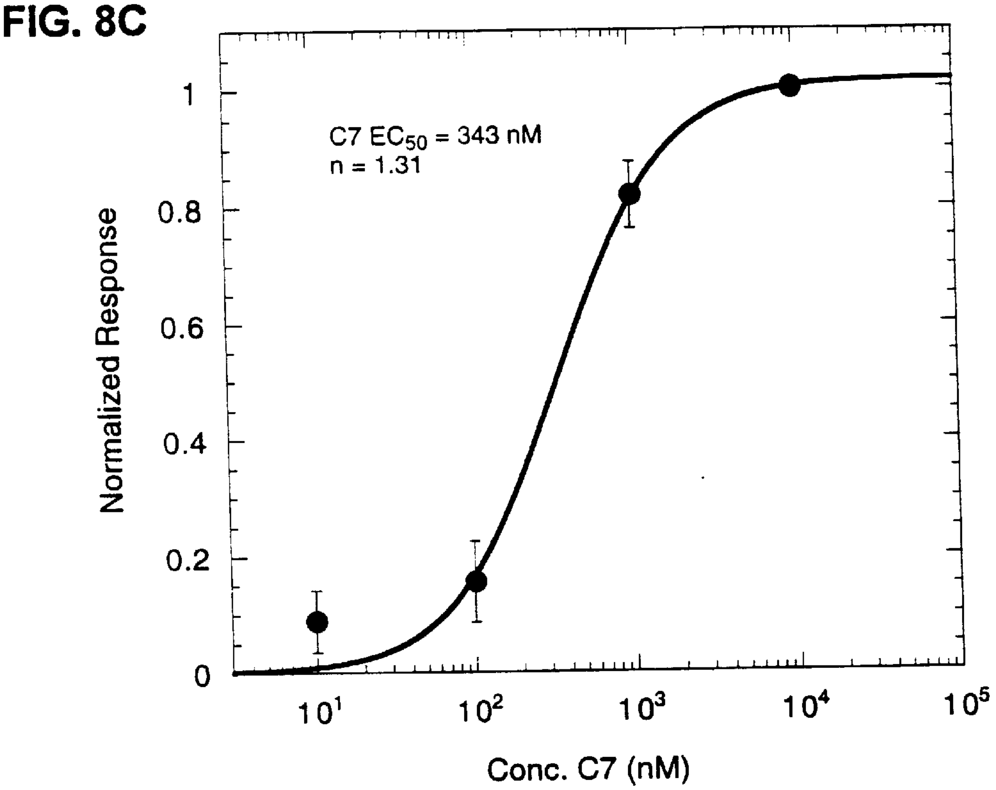
Figure 8D:
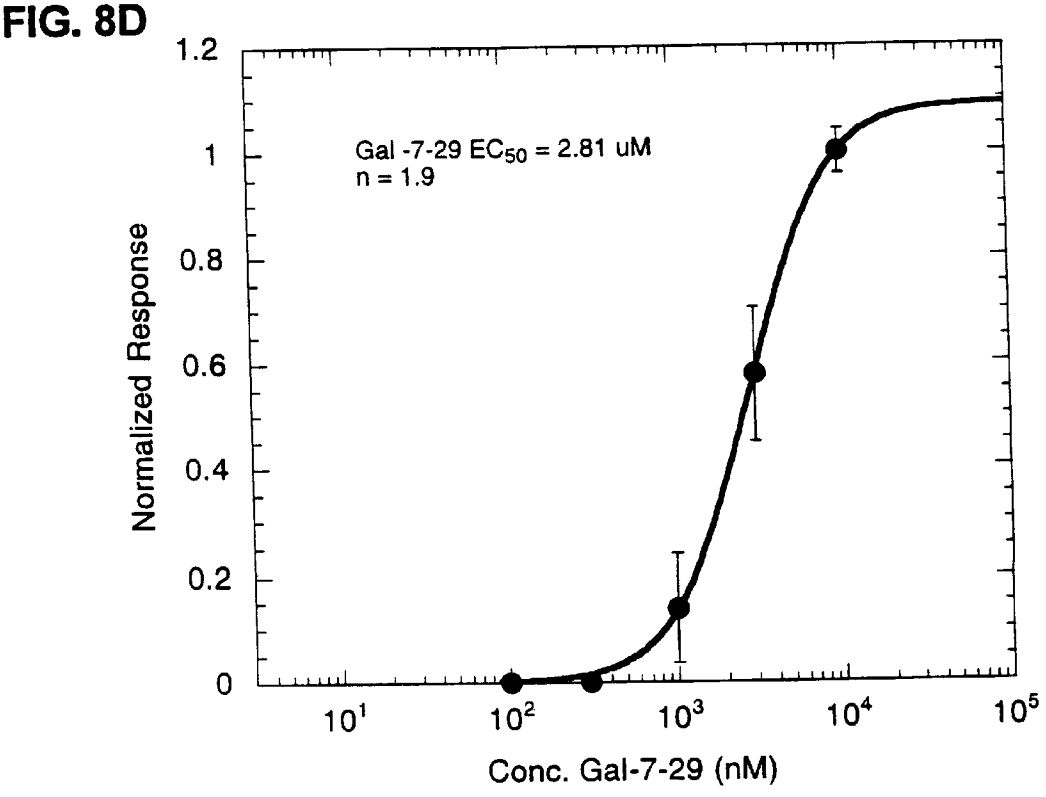
Figure 8E:
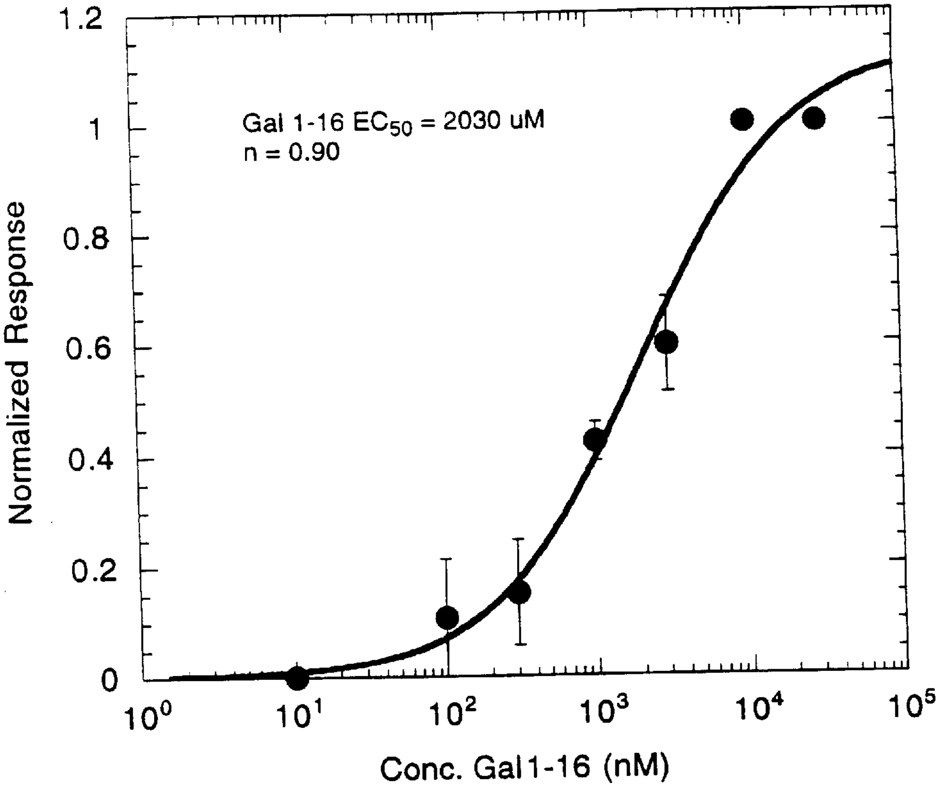
Figure 8F:
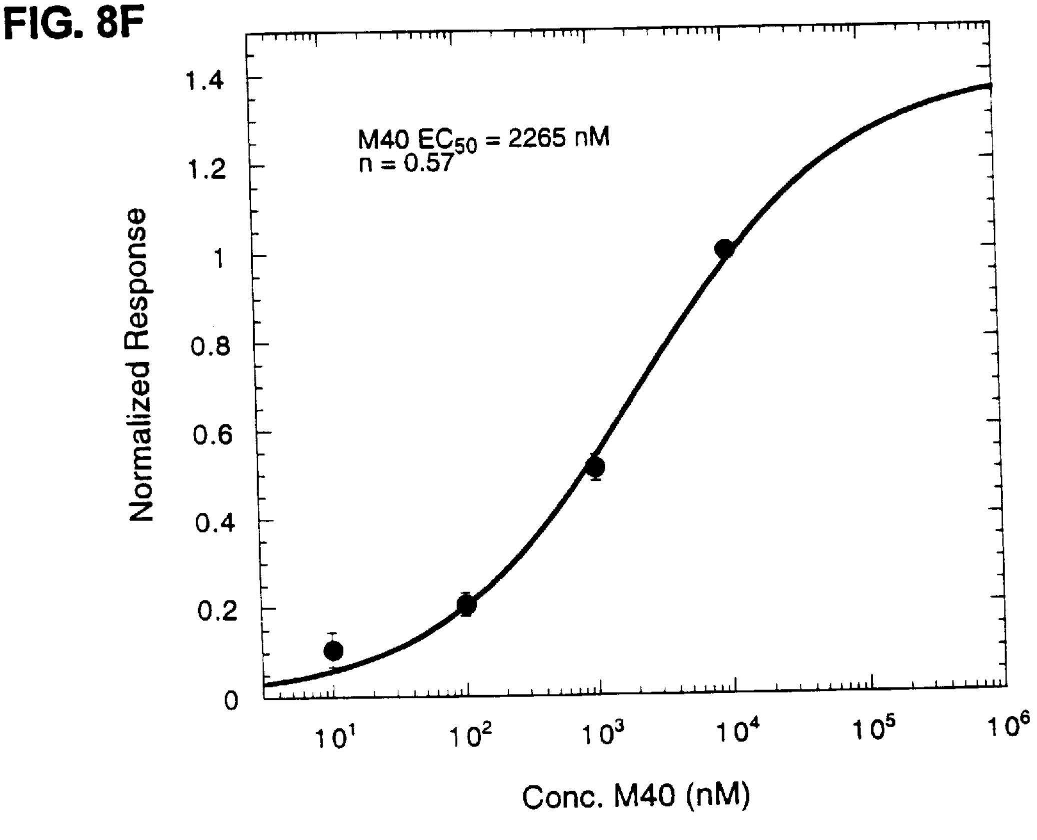
Figure 8G:
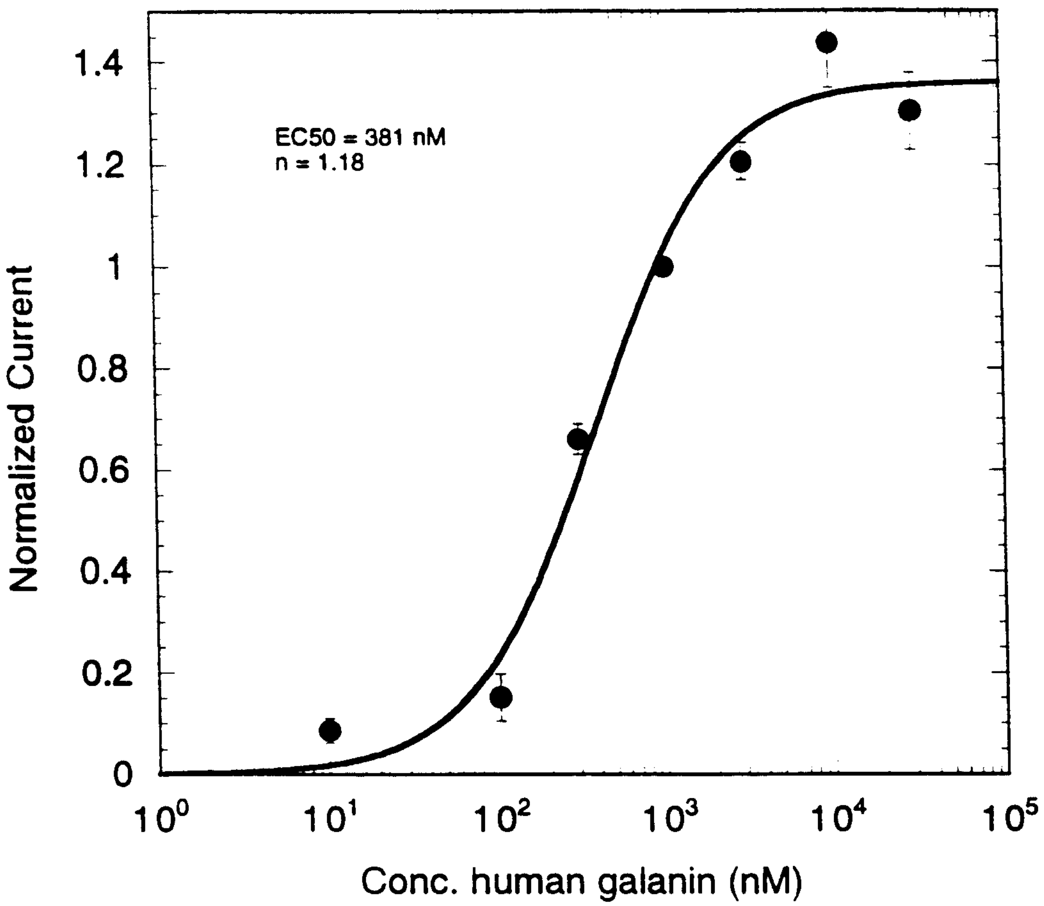
Figure 9A:
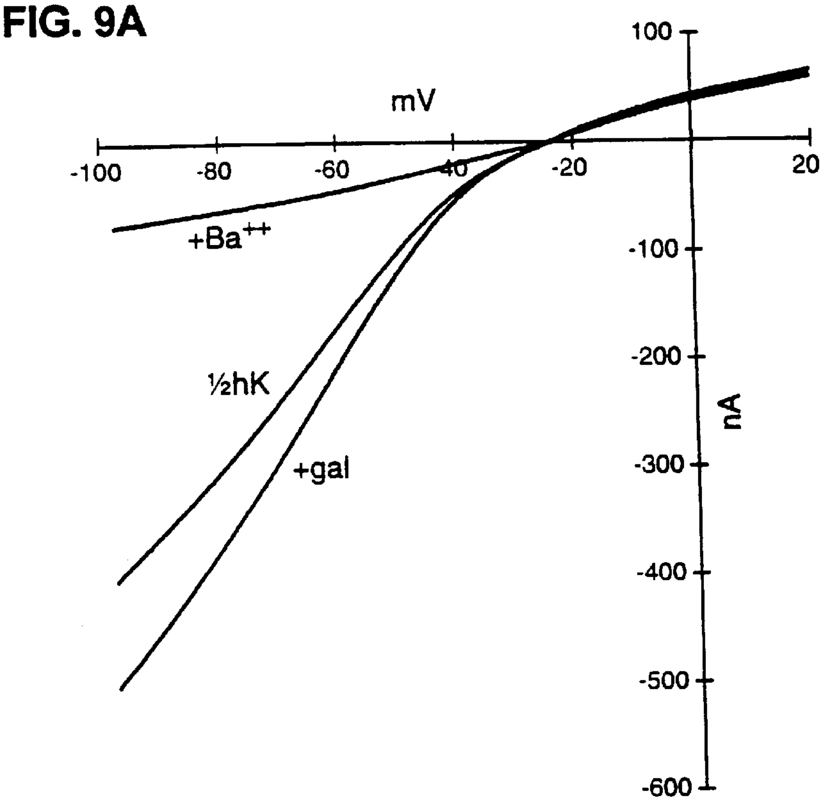
FIGS. 9A–9B FIG. 9A: Current-voltage relation for responses generated by galanin in oocytes expressing hGalR3, GIRK1 and GIRK4. Voltage ramps from −100 to +20 mV were applied at a rate of 50 mV/s. Ramps were generated in ½ hK, ½ hK+1 $\mu$M galanin, and ½ hK+galanin+300 $\mu$M $Ba^{++}$.
Figure 9B:
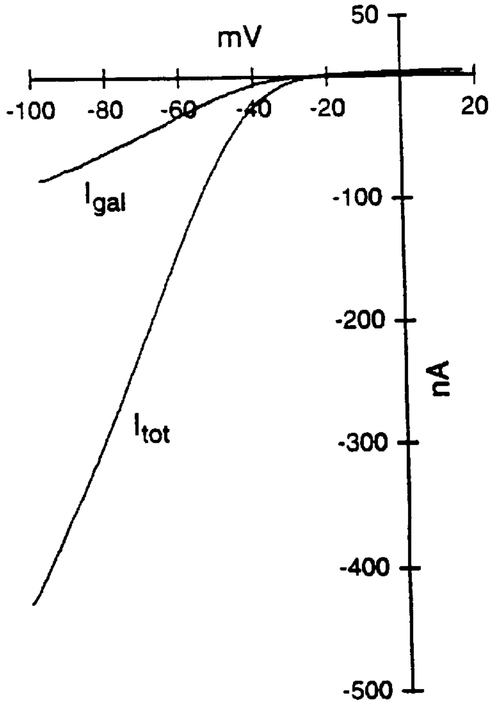
Figure 10:
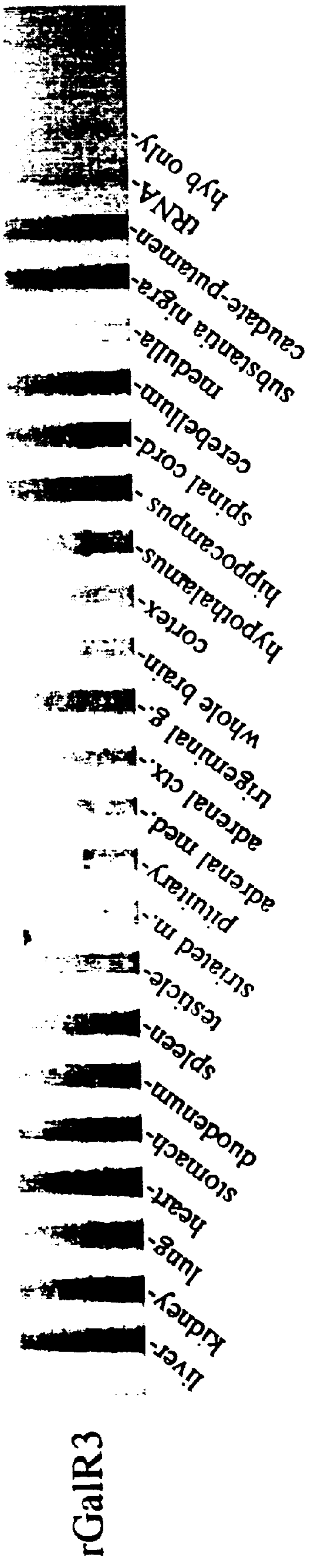
FIG. 10 Autoradiograph demonstrating hybridization of radiolabeled rat GALR3 probe to RNA extracted from rat tissue in a solution hybridization/nuclease protection assay using $^{32}P$ labeled riboprobe. 2 $\mu$g of mRNA was used in each assay. The single band represents mRNA coding for the rat GALR3 receptor extracted from tissue indicated at the bottom of the gel. mRNA coding for the rGalR3 is present in: kidney, stomach, pancreas, pituitary, adrenal medulla, whole brain, hypothalamus, spinal cord, and medulla. Integrity of RNA was assessed using hybridization to mRNA coding to GAPDH. Biomax Film; 18 hr exposure, −70° C.

Other GPCRs, when expressed in Xenopus oocytes, activate a $Ca^{++}$-dependent $Cl^-$ conductance that results from the activation of phospholipase C and the subsequent release of $Ca^{++}$ from intracellular stores. This pathway was not activated in oocytes expressing hGALR3 since $Cl^-$ currents were never observed following application of galanin (n=20). ($Cl^-$ currents were also not observed in oocytes expressing the GALR1 receptor.) In contrast, in oocytes expressing mRNAs encoding GALR2 or $\alpha_{1a}$ receptors, 1 $\mu$M galanin or epinephrine, respectively, stimulates transient $Cl^-$ currents (data not shown). To provide further evidence that hGALR3 couples to the Go/Gi family of G-proteins, batches of oocytes, previously injected with hGALR3 and GIRK mRNAs, were injected with pertussis toxin (2 ng/oocyte) and tested for receptor coupling to $K^+$ currents. In oocytes treated with the toxin, galanin currents were completely abolished (FIG. 7); oocytes injected with buffer alone displayed normal galanin-induced currents. A similar sensitivity to pertussis toxin was observed for oocytes expressing GALR1 receptors. Agonist responses in oocytes expressing GALR2 or $\alpha_{1a}$ adrenergic receptors were unaffected by pertussis toxin (FIG. 7, Table 6). Taken together, these results support the conclusion that GALR1 and GALR3 receptors couple to a Gi/Go pathway, and that GALR2 (like the $\alpha_{1a}$ adrenergic receptor) couples to a $G_q$-type pathway (Table 7).

TABLE 6

Effects of pertussis toxin treatment on currents generated by stimulation of galanin or alpha adrenergic receptors expressed in oocytes. Current is presented in nA (nanoamperes).

| | Receptor | | | |
|---|---|---|---|---|
| | rat GALR1 | rat GALR2 | human GALR3 | Alpha 1a |
| Control | 1775 ± 278 | 229 ± 60 | 24 ± 5 | 5483 ± 1154 |
| PTX | 17 ± 3 | 238 ± 51 | 0 ± 0 | 6350 ± 1318 |

TABLE 7

Comparison of intracellular signaling pathways for three galanin receptors expressed in oocytes.

| | Signaling pathway | | |
|---|---|---|---|
| Receptor | Activates Cl current | Activates GIRKs | PTX sensitive |
| rGALR1 | no | yes | yes |
| rGALR2 | yes | no | no |
| hGALR3 | no | yes | yes |

Pharmacology of hGALR3 in Oocytes

Figure 6B:
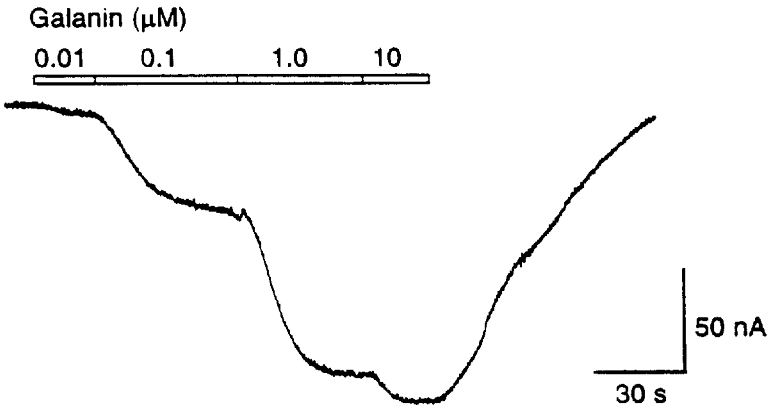

A series of galanin and galanin-related peptides were tested at the human GALR3 receptor for agonist and antagonist activities. Of these peptides, porcine galanin, human galanin, M32, C7, M35, M15 (spantide), galanin −7–29, galanin 1–16, and M40 evoked agonist activity at a fixed dose of 1 $\mu$M. D-Trp2-galanin and galanin 3–29 were inactive. $EC_{50}$s were constructed from cumulative concentration-response measurements performed on a series of oocytes (FIGS. 6B, 8). $EC_{50}$s (in rank order) for M32, porcine galanin, C7, human galanin, galanin −7 to 29, galanin 1–16, and M40 were 45, 222, 343, 381, 1906, 2030, and 2265 nM, respectively (Table 8). This rank order of potency was similar to that observed for $K_i$ values in binding assays using the human GalR3 receptor in LM(tk−) cell.

We have observed that the peptide galanin −7–29, which binds selectively to GALR3 over GALR1 and to GALR2 over GALR1, induces feeding in rats when injected i.c.v. Another peptide, shown in binding and functional studies to selectively bind to the GALR2 receptor over both GALR1 and GALR3, did not stimulate feeding when injected i.c.v. Taken together, these results suggest a role for GALR3 in mediating galanin-induced feeding.

TABLE 8

Comparison of rank orders of $EC_{50}$s for stimulation of GIRKs, apparent binding affinities ($K_i$) and $EC_{50}$s for stimulation of feeding behavior in vivo.

| Peptide | Oocyte $EC_{50}$ (nM) | rat GALR3 Cos-7 $K_i$ (nM) | human GALR3LM (tk-) Ki (nM) |
|---|---|---|---|
| M32 | 45 | 1.9 | 6.0 |
| p-Galanin | 222 | 5.1 | |
| C7 | 343 | 23.0 | 8.1 |
| human galanin | 381 | | |
| gal −7 to 29 | 1,906 | 3.3 | 28.8 |
| gal 1–16 | 2,030 | 51.9 | 319 |
| M40 | 2,265 | 103.0 | 281 |

Further Pharmacologic Characterization Galaninergic Peptides

Peptide ligands were evaluated in binding and functional assays Tables 9–11).

TABLE 9

Binding Data for Rat Galanin Receptors Ki (nM) from porcine

| | 125I-galanin binding assay | | |
|---|---|---|---|
| Peptide | Rat GalR1 CHO | Rat GALR2 LMTK #4 | Rat GALR3 293 #105 |
| (3-iodo-L-Tyr9)-(3-iodo-L-Tyr26)-galanin | | | |
| M32 | 0.70 | 0.69 | 1.32 |
| C7 | 1.44 | 0.56 | 11.75 |
| Rat galanin 1-29 | 0.31 | 1.43 | 2.73 |
| porcine galanin | 0.32 | 1.02 | 2.81 |
| M35 | 0.37 | 4.27 | 3.24 |
| (−7) to (+29) galanin, porcine | 36.31 | 3.16 | 21.38 |
| galantide | 0.67 | 2.14 | 11.48 |
| (−)9 to (+)29 galanin, porcine | 51.29 | 3.47 | 4.17 |
| Human galanin | 0.62 | 2.54 | 53.09 |
| Tyr9-iodo-M35 | | | |
| M40 | 7.76 | 3.76 | 85.11 |
| Porcine galanin 1-12 | | | |
| Porcine galanin 1-15 | | | |
| porcine galanin 1-16 | 2.45 | 2.75 | 138.04 |
| D-Trp2-(d-iodo-L-Tyr9)-(3-iodo-L-Tyr26)-galanin | >1000 | 1.51 | 181.97 |

TABLE 10

Binding Data for Human Receptors

| Peptide | Ki (nM) from porcine 125I-galanin binding assay Hum GALR1 LM(tk-) | Hum GALR2 CHQ | Hum GALR3 LMTK- #8 |
|---|---|---|---|
| (3-iodo-L-Tyr9)-(3-iodo-L-Tyr26)-galanin | 0.21 | 0.40 | 1.43 |
| M32 | 0.26 | 1.45 | 6.03 |
| C7 | 0.26 | 0.63 | 8.13 |
| Rat galanin 1-29 | 0.29 | 1.62 | 8.81 |
| porcine galanin | 0.23 | 0.97 | 8.97 |
| M35 | 0.11 | 1.95 | 14.62 |
| (−7) to (+29) galanin, porcine | 6.84 | 4.95 | 28.84 |
| galantide | 0.25 | 1.08 | 40.18 |
| (−)9 to (+)29 galanin, porcine | 7.85 | 5.43 | 50.12 |
| Human galanin | 0.44 | 2.34 | 69.41 |
| Tyr9-iodo-M35 | 0.83 | 1.45 | 87.10 |
| M40 | 2.38 | 4.04 | 280.54 |
| Porcine galanin 1-12 | 61.66 | 5.17 | 306.67 |
| Porcine galanin 1-15 | 3.98 | 6.13 | 309.03 |
| porcine galanin 1-16 | 1.89 | 5.37 | 319.15 |
| D-Trp2-(d-iodo-L-Tyr9)-(3-iodo-L-Tyr26)-galanin | 169.82 | 21.38 | 933.25 |
| Porcine galanin 3-29 | >1000 | >1000 | >1000 |
| Porcine galanin 1-9 | >1000 | >1000 | >1000 |
| human galanin 3-30 | >1000 | >1000 | >1000 |
| porcine galanin 1-13 | 7.94 | 28.18 | >1000 |
| GMAP 44-59 amide | >1000 | >1000 | >1000 |
| GMAP 25-41 amide | >1000 | >1000 | >1000 |
| GMAP 16-41 amide | >1000 | >1000 | >1000 |
| GMAP 1-41 amide | >1000 | >1000 | >1000 |

TABLE 11

Functional Data at Galanin Receptors

| Peptide | $EC_{50}$ (nM) Rat GALR1 LM(tk-) cAMP | Rat GALR2 CHO #79 AA | Human GALR3 GIRK |
|---|---|---|---|
| p gal 1-16 | 0.34 | 2.63 | 2000 |
| p galanin | 0.06 | 1.25 | 238 |
| human galanin | 0.21 | 0.74 | 7340 |
| C7 | 0.52 | 2.41 | 343 |
| M40 | 0.82 | 2.69 | 5030 |
| M32 | 0.34 | 2.51 | 45 |
| rat gal | 0.06 | 0.71 | |

Experimental Discussion

Using a combination of homology and expression cloning strategies, nucleic acids have been isolated encoding a novel galanin receptor, termed GALR3, that is distinct from the previously cloned GALR1 and GALR2 receptors.

The rat GALR3 gene, whose sequence is derived from cDNA, does not have any other MET upstream of the proposed starting MET, in any of the three possible reading frames.

The human GALR3 gene contains two in-frame METs: the first (as one reads 5' to 3') will be referred to herein as the "upstream MET" and the second (i.e., closer to TM1) will be referred to herein as the "downstream MET." Both the upstream and downstream METs are shown in FIG. 4 (Seq. ID No: 4). Based on data currently available, it is believed that the downstream MET is likely to be the correct initiating methionine. It is theoretically possible that the upstream MET might be the initiating MET. It is to be understood that the present invention includes both the receptor beginning at the downstream MET and the receptor beginning at the upstream MET.

The existence of multiple galanin receptor subtypes suggests the potential for the design and discovery of novel subtype selective compounds. In this regard, the expression of the cDNA encoding the GALR3 receptor in cultured cell lines and other cells provides a unique tool for the discovery of therapeutic agents targeted at galanin receptors.

The localization of GALR1 receptors to multiple brain regions (Gustafson, et al., 1996; Parker, et al., 1995) and the identification of GALR3 in a hypothalamic cDNA library, suggests multiple therapeutic indications for the use of galanin receptor-selective drugs. These include feeding, cognition, analgesia and/or sensory processing, and anxiety and depression.

The observation that galanin is co-released with norepinephrine from sympathetic nerve terminals suggests that galanin could act via galanin receptors in the periphery to modulate nearly every physiological process controlled by sympathetic innervation. Additional therapeutic indications not directly related to localization include diabetes, hypertension, cardiovascular disorders, regulation of growth hormone release, regulation of fertility, gastric ulcers, gastrointestinal motility/transit/absorption/secretion, glaucoma, inflammation, immune disorders, respiratory disorders (e.g., asthma, emphysema).

The physiological and anatomical distribution of galanin-containing neurons suggests potential roles of galanin receptors mediating effects on cognition, analgesia, neuroendocrine regulation, control of insulin release and control of feeding behavior. Of particular relevance to the role of the novel GALR3 receptor, are those functions mediated by galanin receptors in the rat hypothalamus.

Studies in rats indicate that the injection of galanin in the hypothalamus increases food intake (Kyrouli et al, 1990, and Schick et al, 1993) and that this stimulatory effect of galanin is blocked by prior administration of M40 and C7 (Liebowitz and Kim, 1992; and Corwin, 1993) The expression of the mRNA encoding the GALRL receptor in the rat hypothalamus (Parker et al., 1995; Gustafson et al., 1996), and the fact that the novel GALR3 receptor was identified in a cDNA library prepared from rat hypothalamus argues in favor of the involvement of one or more galanin receptor subtypes in the regulation of feeding behavior. However, the original evidence against the involvement of GALR1 in the stimulation of feeding behavior stems from the fact that M40 and C7 are known to be agonists, and not antagonists, in cell lines expressing human and rat GALR1 receptors (Heuillet et al. 1994; Hale et al. 1993; and Bartfai et al. 1993).

Peptide displacement assays indicate that the rat GALR3 receptor has a unique pharmacological profile. The low affinity for M40, in particular, invites further speculation as to the physiological role of the rat GALR3 receptor. It is noted that M40 was reported to be inactive, for example, when tested for antagonism of galaninergic inhibition of glucose-stimulated insulin release in rat pancreas, (Bartfai, 1993). In another example, intrathecal M40 was a weak antagonist of the galanin-facilitated flexor reflex in rat (Xu, 1995). It was observed in feeding assays that M40 was less potent but as effective as galanin in stimulating food intake when injected i.c.v. into rat brain. The data are consistent with a role for the GALR3 receptor in a range of physiologic and pathophysiologic functions including diabetes, pain, obesity and eating disorders, and furthermore suggest that the rat GALR3 receptor may represent a target for the design of therapeutic compounds. The cloning of the rat GALR3 receptor further enables the design and development of in vitro functional assays to determine the agonist or antagonist properties of peptides and drug development candidates.

REFERENCES

Ahrén, B. and S. Lindskog (1992) *Int. J. Pancreatol.* 11:147–160.

Amiranoff, B. A. M. Lorinet, and M. Laburthe (1991) *Eur. J. Biochem.* 195:459–463.

Amiranoff, B. A. L. Servin, C. Rouyer-Fessard, A. Couvineau, K. Tatemoto, and M. Laburthe (1987) *Endocrin.* 121:284–289.

Aruffo, A. and B. Seed (1987) *Proc. Natl. Acad. Sci. USA* 84:8573–8577.

Bhathena, S. J., H. K. Oie, A. F. Gazdar, N. R. Voyles, S. D. Wilkins, and L. Recant (1982) *Diabetes* 31:521–531.

Bartfai, T., K. Bedecs, T. Land, Ü. Langel, R. Bertorelli, P. Girotti, S. Consolo, Y.-J. Yu, Z. Weisenfeld-Hallin, S. Nilsson, V. Pieribone, and T. Hökfelt (1991) *Proc. Natl. Acad. Sci. USA* 88:10961–10965.

Bartfai, T., T. Hokfelt, and U. Langel, *Crit. Rev. Neurobiol.* (1993) 7:229–274.

Bartfai, T., Ü. Langel, K. Bedecs, S. Andell, T. Land, S. Gregersen, B. Ahren, P. Girotti, S. Consolo, R. Corwin, J. Crawley, X. Xu, Z. Weisenfeld-Hallin, and T. Hökfelt (1993) *Proc. Natl. Acad. Sci. USA* 88:11287–11291.

Benriet, W. M., S. F. Hill, M. A. Ghatei, and S. R. Bloom (1991) *J. Endocrin.* 130:463–467.

Boyle, M. R., C. B. Verchere, G. McKnight, S. Mathews, K. Walker, and G. J. Taborsky, Jr. (1994) *Reg. Peptides* 50:1–11.

Bradford, M. M. (1976). A rapid and sensitive method for the quantitation of microgram quantities of protein utilizing the principle of protein-dye binding. *Anal. Biochem.* 72: 248–254.

Burbach, J. P. and O. C. Meijer (1992) *Eur. J. Pharmacol.* 227:1–18.

Burgevin, M.-C., Loquet, I., Quarteronet, D., and Habert-Ortoli, E. (1995) *J. Molec. Neurosci.,* 6:33–41.

Bush, A. W., Borden, L. A., Greene, L. A., and Maxfield, F. R. (1991) *J. Neurochem.* 57:562–574.

Chan-Palay, V. (1988) *J.Comp.Neurol.* 273:543–557.

Chen, Y., A. Fournier, A. Couvineau, M. Laburthe, and B. Amiranoff (1993) *Proc. Natl. Acad. Sci. USA* 90:3845–3849.

Chirgwin, J. M., A. E. Przybyla, R. J. MacDonald, and W. J. Rutter. (1979) *Biochemistry* 18:5294–5299.

Consolo, S., R. Bertorelli, P. Girotti, C. La Porta, T. Bartfai, M. Parenti, and M. Zambelli (1991) *Neurosci. Lett.* 126:29–32.

Crawley, J. N. (1993) *Behav. Brain Res.* 57:133–141.

Crawley, J. N., J. K. Robinson, U. Langel, and T. Bartfai (1993) *Brain. Res.* 600:268–272.

Cullen, B. (1987). Use of eurkaryotic expression technology in the functional analysis of cloned genes. *Methods Enzymol.* 152: 685–704.

D'Andrea, A. D., H. F. Lodish, and G. W. Gordon (1989) *Cell* 57:277–285.

Dascal, N., W. Schreibmayer, N. F. Lim, W. Wang, C. Chavkin, L. DiMagno, C. Labarca, B. L. Kieffer, C. Gaveriaux-Ruff, D. Trollinger, H. A. Lester, and N. Davidson (1993) *Proc. Natl. Acad. Sci. USA* 90:10235–10239.

Fisone, G., C. F. Wu, S. Consolo, Ö. Nördstrom, N. Brynne, T. Bartfai, T. Melander, T. Hökfelt (1987) *Proc. Natl. Acad. Sci USA* 84:7339.

Gearing, D. P., King, J. A., Gough, N. M. and Nicola N. A. (1989) *EMBO J.* 8:3667–3676.

Gerald, C., M. Walker, T. Branchek, and R. Weinshank (1994) DNA Encoding a Human Neuropeptide Y/Peptide YY (Y2) Receptor and Uses Thereof, U.S. Pat. No. 5,545,549, issued Aug. 13, 1996, U.S. Ser. No. 08/192, 288, filed Feb. 3, 1994.

Gillison, S. L., and W. G. Sharp (1994) *Diabetes* 43:24–32.

Gregersen, S., S. Lindskog, T. Lana. U. Langel, T. Bartfai, and B. Ahren (1993) *Eur J. Pharmacol.* 232:35–39.

Gu, Z.-F., W. J. Rossowski, D. H. Coy, T. K. Pradhan, and R. T. Jensen (1993) *J. Phamacol. Exper. Ther.* 266:912–918.

Gu, Z.-F., Pradhan, T. K., Coy, D. H., and Jensen, R. T. (1995) *J. Pharmacol. Exp. Ther.,* 272:371–378.

Gubler, U abd B. J. Hoffman. (1983). A simple and very efficient method for generating cDNA libraries. *Gene* 25: 263–269.

Gundersen, C. B., R. Miledi, and I. Parker (1983) *Proc. R. Soc. London Ser.* B 219:103–109.

Gustafson, E. L., Smith, K. E., Durkin, M. M., Gerald, C., and Branchek, T. A. (1996) *Neuroreport,* 7:953–957.

Habert-Ortoli, E., Amiranoff, B., Loquet, I., Laburthe, M., and J.-F. Mayaux (1994) *Proc. Natl. Acad. Sci. USA* 91:9780–9783.

Hedlund, P. B., N. Yanaihara, and K. Fuxe (1992) *Eur. J. Pharm.* 224:203–205.

Heuillet, E., Bouaiche, Z., Menager, J., Dugay, P., Munoz, N., Dubois, H., Amiranoff, B., Crespo, A., Lavayre, J., Blanchard, J.-C., and Doble, A. (1994) *Eur. J. Pharmacol.,* 269:139–147.

Kaplan, L. M., S. M. Gabriel, J. I. Koenig, M. E. Sunday, E. R. Spindel, J. B. Martin, and W. W. Chin (1988) *Proc. Natl. Acad. Sci. USA* 85:7408–7412.

Kieffer, B., Befort, K., Gaveriaux-Ruff, C. and Hirth, C. G. (1992). The δ-opioid receptor: Isolation of a cDNA by expression cloning and *Proc. Natl. Acad. Sci. USA* 89:12048–12052.

Kluxen, F. W., Bruns, C. and Lubbert H. (1992). Expression cloning of a rat brain somatostatin receptor cDNA. *Proc. Natl. Acad. Sci. USA* 89:4618–4622.

Kofuji P., Davidson N., Lester, H. A. (1995). Evidence that neuronal G-protein-gated inwardly rectifying $K^+$ channels are activated by G beta gamma subunits and function as heteromultimers. *Proc. Natl. Acad. Sci. USA* 92:6542–6546.

Kornfeld, R. and Kornfeld, S. (1985). Assembly of asparagine linked oligosaccharides. *Annu. Rev. Biochem.* 54:631–664.

Kozak, M. (1989). The scanning model for translation: an update. *J. Cell Biol.* 108: 229–241.

Kozak, M. (1991). Structural features in eukaryotic mRNAs that modulate the initiation of translation. *J. Biol. Chem.* 266: 19867–19870.

Krapivinsky, G., E. A. Gordon, K. Wickman, B. Velimirovic, L. Krapivinsky, and D. E. Clapham (1995) *Nature* 374:135–141.

Krapivinsky G., Krapivinsky L., Velimirovic B., Wickman K., Navarro B., Clapham D. E. (1995b). The cardiac inward rectifier K+ channel subunit, CIR, does not comprise the ATP-sensitive K+ channel, ILATP. *J. Biol. Chem.* 270:28777–28779.

Kubo, Y., E. Reuveny, P. A. Slesinger, Y. N. Jan, and L. Y. Jan (1993) *Nature* 364:802–806.

Kyrkouli, S. E., B. G. Stanley, R. D. Seirafi and S. F. Leibowitz (1990) *Peptides* 11:995–1001.

Lagny-Pourmir, I., A. M. Lorinet, N. Yanaihara, and M. Laburthe (1989) *Peptides* 10:757–761.

Landschultz, W. H., Johnson, P. F. and S. L. McKnight. (1988). The leucine zipper: a hypothetical structure common to a new class of DNA binding proteins. *Science* 240: 1759–1764.

Lazareno, S. and N. Birdsall. (1993). Pharmacological characterization of acetylcholine-stimulated [35S]-GTPγS binding mediated by human muscarinic m1–m4 receptors: antagonist studies. *Br. J. Pharmacol.* 109:1120–1127.

Leibowitz, S. F. and T. Kim (1992) *Brain Res.* 599:148–152.

Liman, E. R., Tytgat, J. and P. Hess (1992) Neuron 9:861–871.

Maggio, R., Vogel Z. and J. Wess. (1993). Coexpression studies with mutant muscarinic/adrenergic receptors provide evidence for intermolecular "cross-talk" between G-protein-linked receptors. Proc. *Natl. Acad. Sci. USA* 90: 3103–3107.

McCormick, M. (1987). Sib Selection. *Methods in Enzymology,* 151: 445–449.

Melander, T., C. Kbhler, S. Nilsson, T. Hökfelt, E. Brodin, E. Theodorsson, and T. Bartfai (1988) *J. Chem. Neuroanat.* 1:213–233.

Merchenthaler, I., F. J. López, and A. Negro-Vilar (1993) *Prog. Neurobiol.* 40:711–769.

Miller, J. and Germain, R. N. (1986). Efficient cell surface expression of class II MHC molecules in the absence of associated invariant chain. *J. Exp. Med.* 164: 1478–1489.

North R. A. (1989). Drug receptors and the inhibition of nerve cells. *Br. J.Pharmacol.* 98:13–23.

Nowak M W, Kearney P C, Sampson J R, Saks M E, Labarca C G, Silverman S K, Zhong W, Thorson J, Abelson J N, Davidson N (1995) Nicotinic receptor binding site probed with unnatural amino acid incorporation in intact cells. *Science* 268:439–442.

Ögren, S.-O., T. Hökfelt, K. Kask, Ü. Langel, and T. Bartfai (1992) *Neurosci.* 51:1.

Palazzi, E., G. Fisone, T. Hökfelt, T. Bartfai, and S. Consolo (1988) *Eur. J. Pharmacol.* 148:479.

Parker, E. M., Izzarelli, D. G., Nowak; H. P., Mahle, C. D., Iben, L. G., Wang, J., and Goldstein, M. E. (1995) *Mol. Brain Res.,* 34:179–189.

Post, C., L. Alari, and T. Hökfelt (1988) *Acta Physiol. Scand.* 132:583.

Probst, W. C., Snyder, L. A., Schuster, D. I., Brosius, J and Sealfon, S. C. (1992). Sequence alignment of the G-protein coupled receptor superfamily. *DNA and Cell Bio.* 11: 1–20.

Quick, M W. and H. A. Lester. (1994) *Meth. Neurosci.* 19:261–279.

Sambrook, J., Fritsch, E. F., and T. Maniatis (1989) Molecular Cloning: A Laboratory Manual, 2nd ed. Cold Spring Harbor Laboratory Press, Cold Spring Harbor, N.Y.

Sanger, S. (1977) *Proc. Natl. Acad. Sci. USA* 74:5463–5467.

Servin, A. L., B. Amiranoff, C. Rouyer-Fessard, K. Tatemoto, and M. Laburthe (1987) *Biochem. Biophys. Res. Conm.* 144:298–306.

Shen, Y., Monsma, F. J. Jr., Metcalf, M. A., Jose, P. A., Hamblin, M. W., and Sibley, D. R. (1993) Molecular Cloning and Expression of a 5-Hydroxytryptamine$_7$ Serotonin Receptor Subtype. *J. Biol. Chem.* 268:18200–18204.

Sims, J. E., C. J. March, D. Cosman, M. B. Widmer, H. R. Macdonald, C. J. McMahan, C. E. Grubin, J. M. Wignal, J. L. Jackson, S. M. Call, D. Freind, A. R. Alpert, S. Gillis, D. L. Urdal, and S. K. Dower (1988) *Science* 241:585–588.

Skofitsch, G. and D. M. Jacobowitz (1985) *Peptides* 6:509–546.

Skofitsch, G., M. A. Sills, and D. M. Jacobowitz (1986) *Peptides* 7:1029–1042.

Smith, K. E., L. A. Borden, P. R. Hartig, T. Branchek, and R. L. Weinshank (1992) *Neuron* 8: 927–935.

Smith, K. E., L. A. Borden, C-H. D. Wang, P. R. Hartig, T. A. Branchek, and R. L. Weinshank (1992a) *Mol. Pharmacol.* 42:563–569.

Smith, K. E., S. G. Fried, M. M. Durkin, E. L. Gustafson, L. A. Borden, T. A. Branchek, and R. L. Weinshank (1995) *FEBS Letters,* 357:86–92.

Stühmer, W. (1992) Meth. Enzymology 207:319–339.

Sundström, E., T. Archer, T. Melander, and T. Hökfelt (1988) *Neurosci. Lett.* 88:331.

Takahashi, T., E. Neher, and B. Sakmann (1987) *Proc. Natl. Acad. Sci. USA* 84:5063–6067.

Tempel, D. L., K. J. Leibowitz, and S. F. Leibowitz (1988) *Peptides* 9:300–314.

Tian, W.-N., Duzic, E., Lanier, S. and R. C. Deth. (1994). Determinants of α2-adrenergic receptor activation of G proteins: evidence for a precoupled receptor/G protein state. *Mol. Pharm.* 45:524–531.

Vrontakis, M. E., L. M. Peden, M. L Duckworth, and H. G. Friesen (1987) *J. Biol. Chem.* 262:16755–16760.

Warden, D. and H. V. Thorne. (1968). Infectivity of polyoma virus DNA for mouse embryo cells in presence of diethylaminoethyl-dextran. *J. Gen. Virol.* 3: 371.

Wiesenfeld-Hallin, Z., X. J. Xu, J. X. Hao, and T. Hökfelt (1993) *Acta Physiol.Scand.* 147:457–458.

Wiesenfeld-Hallin, Z., et al. (1992) *Proc. Natl. Acad. Sci. USA* 89:3334–3337.

Wynick D., D. M. Smith, M. Ghatei, K. Akinsanya, R. Bhogal, P. Purkiss, P. Byfield, N. Yanaihara, and S. R. Bloom (1993) *Proc. Natl. Acad. Sci. USA* 90:4231–4245.0.

Xu, X.-J., Wuesebfeld-Hallin, Z., Langel, U., Bedecs, K. and Bartfai, T. (1995). New high affinity peptide antagonists to the spinal galanin receptor. *Br. J. Pharmacol.* 116:2076–2080.

What is claimed is:

1. A process for identifying a chemical compound which specifically binds to a galanin receptor (GALP3) which comprises contacting cells transfected with DNA encoding and expressing on their cell surface the galin receptor (GALR3) with the compound under conditions suitable for binding, and detecting specific binding of the chemical compound to the galanin receptor (GALR3), wherein the cells prior to being transfected with such DNA do not express the galanin receptor (GALR3) and wherein the galanin receptor (GALP3) is a human galanin receptor (GALR3) which has an amino acid sequence identical to the amino acid sequence shown in FIG. 4 (SEQ ID NO: 4) or that encoded by plasmid pEXJ-hGalR3 (ATCC Accession No. 97827) or the galanin receptor (GALR3) is a rat galanin receptor (GALR3) which has an amino acid sequence identical to the amino acid sequence shown in FIG. 2 (SEQ ID NO: 2) or that encoded by plasmid pEXJ-RGal3T (ATCC Accession No. 97826) or plasmid K1086 (ATCC Accession No. 97747).

2. A process for identifying a chemical compound which specifically binds to a galanin receptor (GALR3) which comprises contacting a membrane fraction from cells transfected with DNA encoding and expressing on their cell surface the galanin receptor (GALR3) with the compound under conditions suitable for binding, and detecting specific binding of the chemical compound to the galanin receptor (GALR3), wherein such cells prior to being transfected with such DNA do not express the galanin receptor (GALR3) and wherein the galanin receptor (GALR3) is a human galanin receptor (GALR3) which has an amino acid sequence identical to the amino acid sequence shown in FIG. 4 (SEQ ID NO: 4) or that encoded by plasmid pFXJ-hGalR3 (ATCC Accession No. 97827) or the galanin receptor (GAILR3) is a rat galanin receptor (GALR3) which has an amino acid sequence identical to the amino acid sequence shown in FIG. 2 (SEQ ID NO: 2) or that encoded by plasmid pEXJ-RGalR3T (ATTC Accession No. 97826) or plasmid K1086 (ATCC Accession Nc. 97747).

3. The process of claim 1 or 2, wherein the cells are transfected with plasmid pEXJ-RGalR3T (ATCC Accession No. 97826).

4. The process of claim 1 or 2, wherein the cell is an insect cell.

5. The process of claim 1 or 2, wherein the cell is a mammalian cell.

6. The process of claim 5, wherein the mammalian cell is nonneuronal in origin.

7. The process of claim 6, wherein the nonneuronal cell is a COS-7 cell, a 293 human embryonic kidney cell, a CHO cell, a NIH-3T3 cell or a LM(tk−) cell.

8. The process of claim 6, wherein the nonneuronal cell is the LM(tk−) cell designated L-hGalR3-228 (ATCC Accession No. CRL-12373).

9. The process of claim 6, wherein the nonneuronal cell is the 293 human embryonic kidney cell designated 293-rGalR3-105 (ATCC Accession No. CRL-12287).

10. A process involving competitive binding for identifying a chemical compound which specifically binds to a galanin receptor (GALR3) which comprises separately contacting cells transfected with DNA encoding and expressing on their cell surface the galanin receptor (GALR3), wherein such cells prior to being transfected with such DNA do not express the galanin receptor (GALR3), with both the chemical compound and a second chemical compound known to bind to the receptor, and with only the second chemical compound, under conditions suitable for binding of both compounds, and detecting specific binding of the chemical compound to the galanin receptor (GALP3), a decrease in the binding of the second chemical compound to the galanin receptor (GALR3) in the presence of the chemical compound indicating that the chemical compound specifically hinds to the galanin receptor (GALR3), wherein the galanin receptor (GALR3) is a human galanin receptor (GALR3) which has an amino acid sequence identical to the amino acid sequence shown in FIG. 4 (SEQ ID NO: 4) or that encoded by plasmid pEXJ-hGalR3 (ATCC Accession No. 97827) (or the galanin receptor (GALR3) is a rat galanin receptor (GALR3) which has an amino acid sequence identical to the amino acid sequence shown in FIG. 2 (SEQ ID NO: 2) or that encoded by plasmid pEXJ-RGalR3T (ATCC Accession No. 97826) or plasmid K1086 (ATCC Accession No. 97747).

11. A process involving competitive binding for identifying a chemical compound which specifically binds to a human galanin receptor (GALR3) which comprises contacting a membrane traction from cells transfected with DNA encoding and expressing on their cell surface the galanin receptor (GALR3), wherein such cells prior to being transfected with such DNA do not express the galanin receptor (CALR3), with both the chemical compound and a second chemical compound known to bind to the receptor, and separately with only the second chemical compound, under conditions suitable for binding of both compounds, and detecting specific binding of the chemical compound to the galanin receptor (GALR3), a decrease in the binding of the second chemical compound to the galanin receptor (GALR3) in the presence of the chemical compound indicating that the chemical compound birds to the galanin receptor (GALR3), wherein the galanin receptor (GALR3) is a human galanin receptor (GALR3) which has an amino acid sequence identical to the amino acid sequence shown in FIG. 4 (SEQ ID NO: 4) or that encoded by plasmid pEXJ-hGalR3 (ATCC Accession No. 97827) or the galanin receptor (GALR3) is a rat galanin receptor (GALR3) which has an amino acid sequence identical to the amino acid sequence shown in FIG. 2 (SEQ ID NO: 2) or that encoded by plasmid pEXJ-RGalR3T (ATCC Accession No. 97826) or plasmid K1086 (ATCC Accession No. 97747).

12. A method of screening a plurality of chemical compounds not known to bind to a galanin receptor (GALR3) to identify a compound which specifically binds to the galanin receptor (GALR3) which comprises:

(a) contacting cells transfected with and expressing DNA encoding, and expressing on their cell surface, the galanin receptor (GALR3) with a compound known to bind specifically to the galanin receptor (GALR3), wherein such cells prior to being transfected with such DNA do not express the galanin receptor (GALR3);

(b) contacting the cells from step (a) with the plurality of compounds not known to bind specifically to the galanin receptor (GALR3), under conditions permitting binding of compounds known to bind the galanin receptor (GALR3);

(c) determining whether the binding of the compound known to bind to the galanin receptor (GALR3) is reduced in the presence of one or more of the compounds, relative to the binding of the compound in the absence of the plurality of compounds; and if so (d) separately determining the binding to the galanin receptor (GALR3) of each such compound included in the plurality of compounds so as to thereby identify such compound as one which specifically binds to the galanin receptor (GALR3), wherein the galanin receptor (GALR3) is a human galanin receptor (GALR3) which has an amino acid sequence identical to the amino acid sequence shown in FIG. 4 (SEQ ID NO: 4) or that encoded by plasmid pEXJ-hGalR3 (ATCC Accession No. 97827) or the galanin receptor (GALR3) is a rat galanin receptor (GALR3) which has an amino acid sequence identical to the amino acid sequence shown in FIG. 2 (SEQ ID No: 2) or that encoded by plasmid pEXJ-RGalR3T (ATCC Accession No. 97826) or plasmid K1086 (ATCC Accession No. 97747).

13. A method of screening a plurality of chemical compounds not known to bind to a galanin receptor (GALR3) to identify a compound which specifically binds to the galanin receptor (GALR3), which comprises:

(a) contacting a membrane fraction from cells transfected with DNA encoding, and expressing on their surface, the galanin receptor (GALR3) with a compound known to bind specifically to the galanin receptor (GALR3), wherein such cells prior to being transfected with such DNA do not express the galanin receptor (GALR3);

(b) contacting the cells from step (a) with the plurality of compounds not known to bind specifically to the galanin receptor (GALR3), under conditions permitting binding of compounds known to bind the galanin receptor (GALR3);

(c) determining whether the binding of the compound known to bind to the galanin receptor (GALR3) is reduced in the presence of one or more of the compounds, relative to the binding of the compound in the absence of the plurality of compounds; and if so (d) separately determining the binding to the galanin receptor (GALR3) of each such compound included in the plurality of compounds, so as to thereby identity such compound as one which specifically binds to the galanin receptor (GALR3), wherein the galanin receptor (GALR3) is a human galanin receptor (GALR3) which has an amino acid sequence identical to the amino acid sequence shown FIG. 4 (SEQ ID NO: 4) or that encoded by plasmid pEXJ-hGalR3 (ATCC Accession No. 97827) or the galanin receptor (GALR3) is a rat galanin receptor (GALR3) which has an amino acid sequence identical to the amino acid sequence shown in FIG. 2 (SEQ ID NO: 2) or that encoded by plasmid pFXJ-RGaIR3T (ATCC Accession No. 97826) or plasmid K1086 (ATCC Accession No. 97747).

14. The process of claim 10, 11, 12 or 13, wherein the cell is a mammalian cell.

15. The process of claim 14, wherein the mammalian cell is nonneuronal in origin.

16. The process of claim 15, wherein the nonneuronal cell is a COS-7 cell, a 293 human embryonic kidney cell, a CHO cell, a NIH-3T3 cell or a LM(tk−) cell.

* * * * *

SEQUENCE LISTING

<160> NUMBER OF SEQ ID NOS: 59

<210> SEQ ID NO 1
<211> LENGTH: 1280
<212> TYPE: DNA
<213> ORGANISM: Rat

<400> SEQUENCE: 1

```
agctccagcc taggcgttct acctggaaga atgcaggggc ccagtaccta ggactgagga     60

agatggctga catccagaac atttcgctgg acagcccagg gagcgtaggg gctgtggcag    120

tgcctgtgat ctttgccctc atcttcctgt tgggcatggt gggcaatggg ctggtgttgg    180

ctgtgctact gcagcctggc ccaagtgcct ggcaggagcc aagcagtacc acagatctct    240

tcatcctcaa cttggccgtg gccgaccttt gcttcatcct gtgctgcgtg cccttccagg    300

cagccatcta cacactggat gcctggctct ttggggcttt cgtgtgcaag acggtacatc    360

tgctcatcta cctcaccatg tatgccagca gcttcaccct ggcggccgtc tccctggaca    420

ggtacctggc tgtgcggcac ccactgcgct ccagagccct gcgcaccccg cgcaacgcgc    480

gcgccgccgt ggggctcgtg tggctgctgg cggctctctt ttccgcgccc tacctaagct    540

attacggcac ggtgcgctac ggcgcgctcg agctctgcgt gcccgcttgg gaggacgcgc    600

ggcggcgcgc gctggacgtg gccaccttcg ccgcgggcta cctgctgccg gtggccgtgg    660

tgagcctggc ctacggacgc acgctatgtt tcctatgggc cgccgtgggt cccgcgggcg    720

cggcggcagc agaggcgcgc agacgggcga ccggccgggc gggacgcgcc atgctggcag    780

tggccgcgct ctacgcgctt tgctggggcc cgcaccacgc gctcatcctc tgcttctggt    840

acggccgctt cgccttcagc ccggccacct acgcctgtcg cctggcctcg cactgcctcg    900

cctacgccaa ctcctgcctt aacccgctcg tctactcgct cgcctcgcgc cacttccgcg    960

cgcgcttccg ccgcctgtgg ccctgcggcc gtcgccgcca ccgccaccac caccgcgctc   1020

atcgagccct ccgtcgtgtc cagccggcgt cttcgggccc cgccggttat cccggcgacg   1080

ccaggcctcg tggttggagt atggagccca gaggggatgc tctgcgtggt ggtggagaga   1140

ctagactaac cctgtccccc aggggacctc aataaccctg cccgcttgga ctctgacgtc   1200

tgtcagaatg ccaccaagga acatctaggg aacggcagtc tcgccaggct ccaccaaaaa   1260

gcagaagcaa agttgcaggg                                                1280
```

<210> SEQ ID NO 2
<211> LENGTH: 370
<212> TYPE: PRT
<213> ORGANISM: Rat

<400> SEQUENCE: 2

```
Met Ala Asp Ile Gln Asn Ile Ser Leu Asp Ser Pro Gly Ser Val Gly
  1               5                  10                  15

Ala Val Ala Val Pro Val Ile Phe Ala Leu Ile Phe Leu Leu Gly Met
             20                  25                  30

Val Gly Asn Gly Leu Val Leu Ala Val Leu Leu Gln Pro Gly Pro Ser
         35                  40                  45

Ala Trp Gln Glu Pro Ser Ser Thr Thr Asp Leu Phe Ile Leu Asn Leu
     50                  55                  60

Ala Val Ala Asp Leu Cys Phe Ile Leu Cys Cys Val Pro Phe Gln Ala
 65                  70                  75                  80
```

-continued

```
Ala Ile Tyr Thr Leu Asp Ala Trp Leu Phe Gly Ala Phe Val Cys Lys
                 85                  90                  95

Thr Cys His Leu Leu Ile Tyr Leu Thr Met Tyr Ala Ser Ser Phe Thr
            100                 105                 110

Leu Ala Ala Val Ser Leu Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190

Tyr Leu Leu Pro Val Ala Val Val Ser Leu Ala Tyr Gly Arg Thr Leu
        195                 200                 205

Cys Phe Leu Trp Ala Ala Val Gly Pro Ala Gly Ala Ala Ala Ala Glu
    210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ser Leu Ala Ser Arg His Phe Arg Ala Arg Phe Arg Arg
    290                 295                 300

Leu Trp Pro Cys Gly Arg Arg Arg His Arg His His His Arg Ala His
305                 310                 315                 320

Arg Ala Leu Arg Arg Val Gln Pro Ala Ser Ser Gly Pro Ala Gly Tyr
                325                 330                 335

Pro Gly Asp Ala Arg Pro Arg Gly Trp Ser Met Glu Pro Arg Gly Asp
            340                 345                 350

Ala Leu Arg Gly Gly Gly Glu Thr Arg Leu Thr Leu Ser Pro Arg Gly
        355                 360                 365

Pro Gln
    370


<210> SEQ ID NO 3
<211> LENGTH: 1417
<212> TYPE: DNA
<213> ORGANISM: Homo sapiens

<400> SEQUENCE: 3

cactcagcga tgactttggc tctgctctcc cctcctccat ctcccacgag cttccagccc      60

agaacacctg gccagaccca ggtcggggga gttagatccc ggggtcaagc aaccagaact     120

gggggctctt gcctgaggat tccagcttct cttcccaggt gcccgtctga tggggagatg     180

gctgatgccc agaacatttc actggacagc ccagggagtg tgggggccgt ggcagtgcct     240

gtggtctttg ccctaatctt cctgctgggc acagtgggca atgggctggt gctggcagtg     300

ctcctgcagc ctggcccgag tgcctggcag gagcctggca gcaccacgga cctgttcatc     360

ctcaacctgg cggtggctga cctctgcttc atcctgtgct gcgtgccctt ccaggccacc     420
```

-continued

```
atctacacgc tggatgcctg gctctttggg gccctcgtct gcaaggccgt gcacctgctc    480

atctacctca ccatgtacgc cagcagcttt acgctggctg ctgtctccgt ggacaggtac    540

ctggccgtgc ggcacccgct gcgctcgcgc gccctgcgca cgccgcgtaa cgcccgcgcc    600

gcagtggggc tggtgtggct gctggcggcg ctcttctcgg cgccctacct cagctactac    660

ggcaccgtgc gctacggcgc gctggagctc tgcgtgcccg cctgggagga cgcgcgccgc    720

cgcgccctgg acgtggccac cttcgctgcc ggctacctgc tgcccgtggc tgtggtgagc    780

ctggcctacg ggcgcacgct gcgcttcctg tgggccgccg tgggtcccgc gggcgcggcg    840

gcggccgagg cgcggcggag ggcgacgggc cgcgcggggc gcgccatgct ggcggtggcc    900

gcgctctacg cgctctgctg ggtccgcac cacgcgctca tcctgtgctt ctggtacggc    960

cgcttcgcct tcagcccggc cacctacgcc tgccgcctgg cctcacactg cctggcctac   1020

gccaactcct gcctcaaccc gctcgtctac gcgctcgcct cgcgccactt ccgcgcgcgc   1080

ttccgccgcc tgtggccgtg cggccgccga cgccgccacc gtgcccgccg cgccttgcgt   1140

cgcgtccgcc ccgcgtcctc gggcccaccc ggctgccccg gagacgcccg gcctagcggg   1200

aggctgctgg ctggtggcgg ccagggcccg gagcccaggg agggacccgt ccacggcgga   1260

gaggctgccc gaggaccgga ataaaccctg ccgcctggac tccgcctgtg tccgtctgtc   1320

tcactcccgt tctccgaagg cgggacgcca ccgggccagg gatggggcaa tgccacgagc   1380

tctctgaggg gcgttgagtg gagcgacttg tccccgc                             1417


<210> SEQ ID NO 4
<211> LENGTH: 427
<212> TYPE: PRT
<213> ORGANISM: Homo sapiens

<400> SEQUENCE: 4

His Ser Ala Met Thr Leu Ala Leu Leu Ser Pro Pro Pro Ser Pro Thr
  1               5                  10                  15

Ser Phe Gln Pro Arg Thr Pro Gly Gln Thr Gln Val Gly Gly Val Arg
             20                  25                  30

Ser Arg Gly Gln Ala Thr Arg Thr Gly Gly Ser Cys Leu Arg Ile Pro
         35                  40                  45

Ala Ser Leu Pro Arg Cys Pro Ser Asp Gly Glu Met Ala Asp Ala Gln
     50                  55                  60

Asn Ile Ser Leu Asp Ser Pro Gly Ser Val Gly Ala Val Ala Val Pro
 65                  70                  75                  80

Val Val Phe Ala Leu Ile Phe Leu Leu Gly Thr Val Gly Asn Gly Leu
                 85                  90                  95

Val Leu Ala Val Leu Leu Gln Pro Gly Pro Ser Ala Trp Gln Glu Pro
            100                 105                 110

Gly Ser Thr Thr Asp Leu Phe Ile Leu Asn Leu Ala Val Ala Asp Leu
        115                 120                 125

Cys Phe Ile Leu Cys Cys Val Pro Phe Gln Ala Thr Ile Tyr Thr Leu
    130                 135                 140

Asp Ala Trp Leu Phe Gly Ala Leu Val Cys Lys Ala Val His Leu Leu
145                 150                 155                 160

Ile Tyr Leu Thr Met Tyr Ala Ser Ser Phe Thr Leu Ala Ala Val Ser
                165                 170                 175

Val Asp Arg Tyr Leu Ala Val Arg His Pro Leu Arg Ser Arg Ala Leu
            180                 185                 190
```

-continued

Arg Thr Pro Arg Asn Ala Arg Ala Ala Val Gly Leu Val Trp Leu Leu
195 200 205

Ala Ala Leu Phe Ser Ala Pro Tyr Leu Ser Tyr Tyr Gly Thr Val Arg
210 215 220

Tyr Gly Ala Leu Glu Leu Cys Val Pro Ala Trp Glu Asp Ala Arg Arg
225 230 235 240

Arg Ala Leu Asp Val Ala Thr Phe Ala Ala Gly Tyr Leu Leu Pro Val
245 250 255

Ala Val Val Ser Leu Ala Tyr Gly Arg Thr Leu Arg Phe Leu Trp Ala
260 265 270

Ala Val Gly Pro Ala Gly Ala Ala Ala Ala Glu Ala Arg Arg Arg Ala
275 280 285

Thr Gly Arg Ala Gly Arg Ala Met Leu Ala Val Ala Ala Leu Tyr Ala
290 295 300

Leu Cys Trp Gly Pro His His Ala Leu Ile Leu Cys Phe Trp Tyr Gly
305 310 315 320

Arg Phe Ala Phe Ser Pro Ala Thr Tyr Ala Cys Arg Leu Ala Ser His
325 330 335

Cys Leu Ala Tyr Ala Asn Ser Cys Leu Asn Pro Leu Val Tyr Ala Leu
340 345 350

Ala Ser Arg His Phe Arg Ala Arg Phe Arg Arg Leu Trp Pro Cys Gly
355 360 365

Arg Arg Arg Arg His Arg Ala Arg Arg Ala Leu Arg Arg Val Arg Pro
370 375 380

Ala Ser Ser Gly Pro Pro Gly Cys Pro Gly Asp Ala Arg Pro Ser Gly
385 390 395 400

Arg Arg Leu Ala Gly Gly Gly Gln Gly Pro Glu Pro Arg Glu Gly Pro
405 410 415

Val His Gly Gly Glu Ala Ala Arg Gly Pro Glu
420 425

<210> SEQ ID NO 5
<211> LENGTH: 346
<212> TYPE: PRT
<213> ORGANISM: Rat

<400> SEQUENCE: 5

Met Glu Leu Ala Pro Val Asn Leu Ser Glu Gly Asn Gly Ser Asp Pro
1 5 10 15

Glu Pro Pro Ala Glu Pro Arg Pro Leu Phe Gly Ile Gly Val Glu Asn
20 25 30

Phe Ile Thr Leu Val Val Phe Gly Leu Ile Phe Ala Met Gly Val Leu
35 40 45

Gly Asn Ser Leu Val Ile Thr Val Leu Ala Arg Ser Lys Pro Gly Lys
50 55 60

Pro Arg Ser Thr Thr Asn Leu Phe Ile Leu Asn Leu Ser Ile Ala Asp
65 70 75 80

Leu Ala Tyr Leu Leu Phe Cys Ile Pro Phe Gln Ala Thr Val Tyr Ala
85 90 95

Leu Pro Thr Trp Val Leu Gly Ala Phe Ile Cys Lys Phe Ile His Tyr
100 105 110

Phe Phe Thr Val Ser Met Leu Val Ser Ile Phe Thr Leu Ala Ala Met
115 120 125

Ser Val Asp Arg Tyr Val Ala Ile Val His Ser Arg Arg Ser Ser Ser
130 135 140

-continued

```
Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220

Leu His Lys Lys Leu Lys Asn Met Ser Lys Lys Ser Glu Ala Ser Lys
225                 230                 235                 240

Lys Lys Thr Ala Gln Thr Val Leu Val Val Val Val Val Phe Gly Ile
                245                 250                 255

Ser Trp Leu Pro His His Val Ile His Leu Trp Ala Glu Phe Gly Ala
            260                 265                 270

Phe Pro Leu Thr Pro Ala Ser Phe Phe Phe Arg Ile Thr Ala His Cys
        275                 280                 285

Leu Ala Tyr Ser Asn Ser Ser Val Asn Pro Ile Ile Tyr Ala Phe Leu
    290                 295                 300

Ser Glu Asn Phe Arg Lys Ala Tyr Lys Gln Val Phe Lys Cys Arg Val
305                 310                 315                 320

Cys Asn Glu Ser Pro His Gly Asp Ala Lys Glu Lys Asn Arg Ile Asp
                325                 330                 335

Thr Pro Pro Ser Thr Asn Cys Thr His Val
            340                 345


<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 6

ttgtacccct atttttcgcg ctcatcttcc tcgtgggcac cgtgg                 45


<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 7

agcaccgcca gcaccagcgc gttgcccacg gtgcccacga ggaag                 45


<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 8

tcagcaccac caacctgttc atcctcaacc tgggcgtggc cgacctgtgt            50
```

-continued

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 9
ggcctggaaa ggcacgcagc acaggatgaa acacaggtcg gccacgccca 50

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 10
ctgcaaggct gttcatttcc tcatctttct cactatgcac gccag 45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 11
ggagacggcg gccagcgtga agctgctggc gtgcatagtg agaaa 45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 12
aacgcgctgg ccgccatcgg gctcatctgg gggctagcac tgctc 45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 13
agtagctcag gtagggcccg gagaagagca gtgctagccc ccaga 45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 14
agccatggac ctctgcacct tcgtctttag ctacctgctg ccagt 45

-continued

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 15
cgcataggtc agactgagga ctagcactgg cagcaggtag ctaaa 45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 16
gatcatcatc gtggcggtgc ttttctgcct ctgttggatg cccca 45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 17
ccacacgcag aggataagcg cgtggtgggg catccaacag aggca 45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 18
gttgcgcatc ctttcacacc tagtttccta tgccaactcc tgtgt 45

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 19
agaccagagc gtaaacgatg gggttgacac aggagttggc atagga 46

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 20
cctcagtgaa gggaatggga gcga 24

<210> SEQ ID NO 21
<211> LENGTH: 27

-continued

<212> TYPE: DNA
<213> ORGANISM: Artificial Sequence
<220> FEATURE:
<223> OTHER INFORMATION: Description of Artificial Sequence:PCR primer

<400> SEQUENCE: 21
gtagtgtata aacttgcaga tgaaggc 27

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 22
atgaatggct ccggcagcca ggg 23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 23
ttgcagagca gcgagccgaa cac 23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 24
ggctgacatc cagaacattt cgct 24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 25
cagatgtacc gtcttgcaca cgaa 24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 26
catctgctca tctacctcac catg 24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:PCR primer -continued

<400> SEQUENCE: 27
cataggaaac atagcgtgcg tccg 24

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 28
aagcttctag agatccctcg acctc 25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 29
aggcgcagaa ctggtaggta tggaa 25

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 30
gctcatcctc tgcttctggt acg 23

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 31
cagatgtacc gtcttgcaca cgaa 24

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence:PCR primer

<400> SEQUENCE: 32
cgaggatccc aactttgcct ctgctttttg gtgg 34

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 33
cctcagtgaa gggaatggga gcga 24

<210> SEQ ID NO 34
<211> LENGTH: 24

-continued

<212> TYPE: DNA
<213> ORGANISM: Artificial Sequence
<220> FEATURE:
<223> OTHER INFORMATION: Description of Artificial Sequence:PCR primer

<400> SEQUENCE: 34
cttgcttgta cgccttccgg aagt 24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 35
tgggcaacag cctagtgatc accg 24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 36
ctgctcccag cagaaggtct ggtt 24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 37
atgaatggct ccggcagcca ggg 23

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 38
ttggagacca gagcgtaaac gatgg 25

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence:
oligonucleotide probe

<400> SEQUENCE: 39
agatggctga catccagaac atttcgctgg acagcccagg gagcg 45

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence:
oligonucleotide probe -continued

<400> SEQUENCE: 40
atcacaggca ctgccacagc ccctacgctc cctgggctgt ccagcg 46

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 41
atggctgatg cccagaacat ttcac 25

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 42
agccaggcat ccagcgtgta gat 23

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence:probe

<400> SEQUENCE: 43
acggtcgctt cgccttcagc ccggccacct acgcctgtcg cctgg 45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence:probe

<400> SEQUENCE: 44
acggtcgctt cgccttcagc ccggccacct acgcctgtcg cctgg 45

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence:probe

<400> SEQUENCE: 45
gcgcaacgcg cgcgccgccg tggggctcgt gtggctgctg gcggc 45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence:probe

<400> SEQUENCE: 46
atctacacgc tggatgcctg gctctttggg gccctcgtct gcaag 45

-continued

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 47
atctacacgc tggatgccct ggct 24

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 48
cgtagcgcac ggtgccgtag ta 22

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 49
gatggatccg ccaccatggc tgatgcccag aacatttcac 40

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 50
gcaggtacct gtccacggag acagcagc 28

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence:probe

<400> SEQUENCE: 51
gatggctgat gcccagaaca tttcactgga cagcccaggg agtgt 45

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence:probe

<400> SEQUENCE: 52
gaccacaggc actgccacgg cccccacact ccctgggctg tccag 45

<210> SEQ ID NO 53
<211> LENGTH: 45
<212> TYPE: DNA

-continued

<213> ORGANISM: Artificial Sequence
<220> FEATURE:
<223> OTHER INFORMATION: Description of Artificial Sequence:probe

<400> SEQUENCE: 53
tgcagcctgg cccaagtgcc tggcaggagc caagcagtac cacag 45

<210> SEQ ID NO 54
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 54
cgcggatcca ttatgtctgc actccgaagg aaatttg 37

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 55
cgcgaattct tatgtgaagc gatcagagtt catttttc 38

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 56
gcgggatccg ctatggctgg tgattctagg aatg 34

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 57
ccggaattcc cctcacaccg agcccctgg 29

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence:primer

<400> SEQUENCE: 58
ccaagcttct aatacgactc actatagggc caccatggct gatgcccaga 50

<210> SEQ ID NO 59
<211> LENGTH: 57
<212> TYPE: DNA
<213> ORGANISM: Artificial Sequence
<220> FEATURE:
<223> OTHER INFORMATION: Description of Artificial Sequence:primer -continued

```
<400> SEQUENCE: 59

tttttttttt tttttttttt tttttttttt tttttgcagg gtttattccg gtcctcg        57
```